US008992424B2

(12) United States Patent
Orbay et al.

(10) Patent No.: US 8,992,424 B2
(45) Date of Patent: Mar. 31, 2015

(54) ENDO-SURGICAL DEVICE AND METHOD

(75) Inventors: Jorge L. Orbay, Miami, FL (US); Jorge A. Machado, Miami, FL (US); Thomas H. Norman, Miami, FL (US); Alejandro Espinosa, Miami, FL (US); Randall Chinock, Southbridge, MA (US); Ronald G. Litke, Jr., Shelton, CT (US); Carlos Valencia, Miami, FL (US)

(73) Assignee: Skeletal Dynamics LLC, Miami, FL (US)

( * ) Notice: Subject to any disclaimer, the term of this patent is extended or adjusted under 35 U.S.C. 154(b) by 1374 days.

(21) Appl. No.: 12/029,232

(22) Filed: Feb. 11, 2008

(65) Prior Publication Data
US 2008/0195128 A1    Aug. 14, 2008

Related U.S. Application Data

(60) Provisional application No. 60/889,064, filed on Feb. 9, 2007, provisional application No. 60/969,484, filed on Aug. 31, 2007, provisional application No. 60/981,656, filed on Oct. 22, 2007, provisional application No. 60/983,436, filed on Oct. 29, 2007, provisional application No. 60/992,930, filed on Dec. 6, 2007.

(51) Int. Cl.
*A61B 1/06* (2006.01)
*A61B 17/32* (2006.01)
(Continued)

(52) U.S. Cl.
CPC ..... *A61B 17/320016* (2013.01); *A61B 1/00048* (2013.01); *A61B 1/00052* (2013.01); *A61B 1/313* (2013.01); *A61B 17/0218* (2013.01);
(Continued)

(58) Field of Classification Search
CPC .............. A61B 17/320036; A61B 2017/32004
USPC ................. 600/104, 106, 109, 112, 129, 183; 606/170
See application file for complete search history.

(56) References Cited

U.S. PATENT DOCUMENTS 769,829 A    9/1904    Mott
4,962,770 A *  10/1990    Agee et al. ..................... 128/898
(Continued)

FOREIGN PATENT DOCUMENTS

JP    9122133 A    5/1997
WO    9312725 A1    7/1993
(Continued)

OTHER PUBLICATIONS

Endogo, palmable endoscopic camera, Redifining the Image of Endoscopy, Envisionier Medical Technologies, LLC, Rockville, MD 20850, www.endogo.com, www.envisionier.com.
(Continued)

*Primary Examiner* — Anhtuan T Nguyen
*Assistant Examiner* — Rynae Boler
(74) *Attorney, Agent, or Firm* — Laurence A. Greenberg; Werner H. Stemer; Ralph E. Locher

(57) ABSTRACT

An endo-surgical device, system and method are provided. The endo-surgical device includes a flared prow that limits the displacement and rotation of the cannula to keep the knife away from tissues that are not intended to be cut. The endo-surgical tool can be utilized as part of a system for performing an endo-surgical procedure.

47 Claims, 45 Drawing Sheets

(51) Int. Cl.
 *A61B 1/00* (2006.01)
 *A61B 1/313* (2006.01)
 *A61B 17/02* (2006.01)
 *A61B 17/3201* (2006.01)
 *A61B 17/34* (2006.01)
 *A61B 19/00* (2006.01)
 *A61B 17/00* (2006.01)
 *A61B 17/3211* (2006.01)
 *A61B 17/29* (2006.01)

(52) U.S. Cl.
 CPC ..... *A61B 17/320036* (2013.01); *A61B 17/3201* (2013.01); *A61B 1/00108* (2013.01); *A61B 17/3421* (2013.01); *A61B 19/5225* (2013.01); *A61B 2017/00464* (2013.01); *A61B 2017/32113* (2013.01); *A61B 2019/5206* (2013.01); *A61B 2019/521* (2013.01); *A61B 2017/00455* (2013.01); *A61B 2017/2927* (2013.01); *A61B 2019/468* (2013.01)
 USPC .......................................... 600/183; 606/170

(56) References Cited

U.S. PATENT DOCUMENTS

| | | | |
|---|---|---|---|
| 4,963,147 A | 10/1990 | Agee et al. | |
| 5,029,573 A | 7/1991 | Chow | |
| 5,089,000 A | 2/1992 | Agee et al. | |
| 5,273,024 A | 12/1993 | Menon et al. | |
| 5,282,816 A * | 2/1994 | Miller et al. | 606/167 |
| 5,306,284 A * | 4/1994 | Agee et al. | 606/170 |
| 5,323,765 A | 6/1994 | Brown | |
| 5,334,214 A | 8/1994 | Putnam | |
| 5,366,465 A | 11/1994 | Mirza | |
| 5,368,014 A | 11/1994 | Anapliotis et al. | |
| 5,387,222 A | 2/1995 | Strickland | |
| 5,423,804 A * | 6/1995 | Kulick | 606/14 |
| 5,507,800 A | 4/1996 | Strickland | |
| 5,569,283 A | 10/1996 | Green et al. | |
| 5,578,051 A | 11/1996 | Mirza | |
| 5,613,976 A | 3/1997 | Agee et al. | |
| 5,722,934 A | 3/1998 | Knight et al. | |
| 5,908,431 A | 6/1999 | Battenfield | |
| 5,928,137 A | 7/1999 | Green | |
| 5,968,061 A | 10/1999 | Mirza | |
| 6,139,489 A * | 10/2000 | Wampler et al. | 600/109 |
| 6,179,852 B1 | 1/2001 | Strickland et al. | |
| 6,387,043 B1 | 5/2002 | Yoon | |
| 6,413,208 B1 | 7/2002 | Schöllhorn et al. | |
| 6,419,626 B1 | 7/2002 | Yoon | |
| 6,432,046 B1 | 8/2002 | Yarush et al. | |
| 6,554,765 B1 | 4/2003 | Yarush et al. | |
| 6,638,289 B1 | 10/2003 | Johnson et al. | |
| 6,692,432 B1 | 2/2004 | Yarush et al. | |
| 7,041,115 B2 | 5/2006 | Mirza et al. | |
| 2003/0065323 A1 | 4/2003 | Hess et al. | |
| 2004/0102804 A1 | 5/2004 | Chin | |
| 2005/0096645 A1 | 5/2005 | Wellman et al. | |
| 2005/0096677 A1* | 5/2005 | Wellman et al. | 606/159 |
| 2008/0255600 A1 | 10/2008 | Braam et al. | |

FOREIGN PATENT DOCUMENTS

| | | |
|---|---|---|
| WO | 9741767 A2 | 11/1997 |
| WO | 2006085090 A2 | 8/2006 |

OTHER PUBLICATIONS

Endogo, palmable endoscopic camera, Redifining the Image of Endoscopy, "The endogo puts capabilities of the traditional video tower system in the palm of your hand" Envisionier Medical Technologies, LLC, Rockville, MD 20850, www.endogo.com, www.envisionier.com.

McGrath, Video Laryngoscope, Series 5, Operator's Manual, Aircraft Medical, Revision 4.1, Nov. 10, 2006.

International Search Report dated Jun. 25, 2008.

International Search Report dated Aug. 7, 2008.

* cited by examiner

FIG. 3A
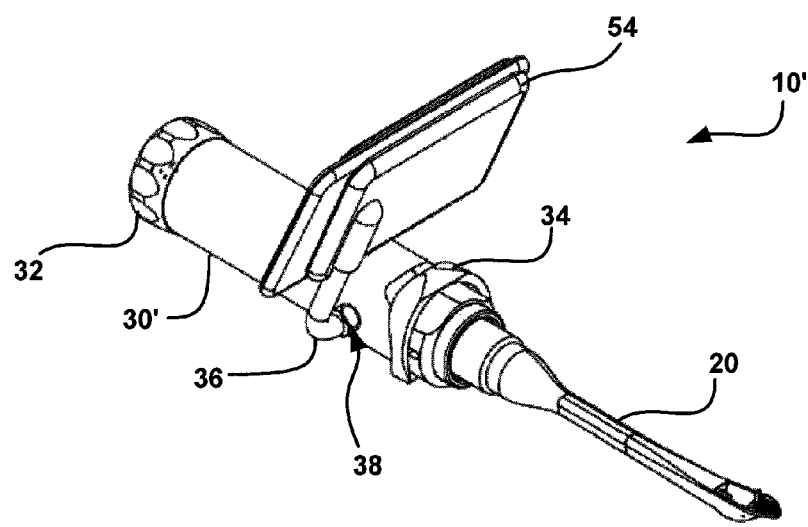
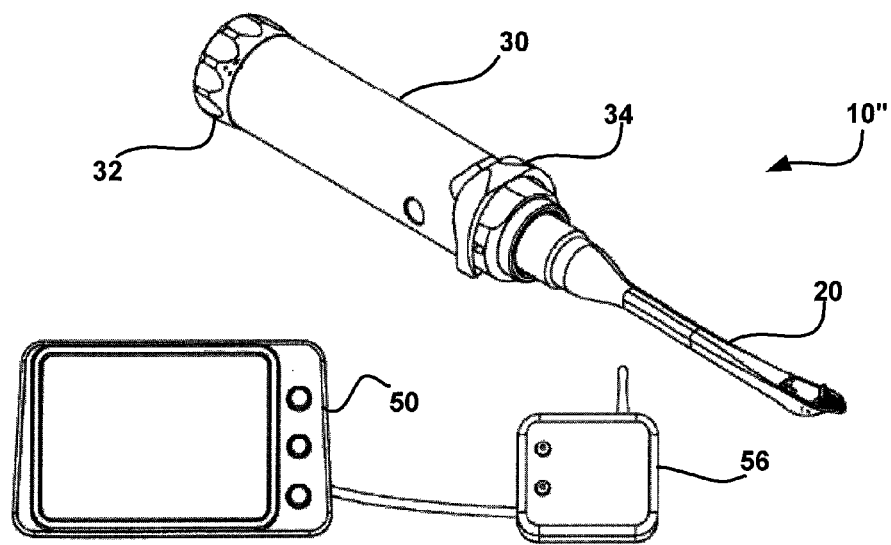
FIG. 3B

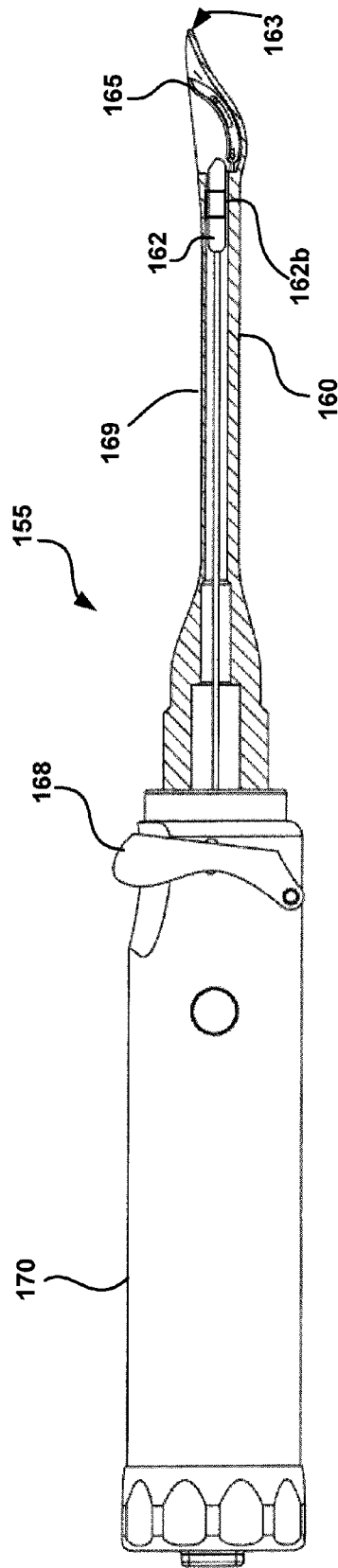
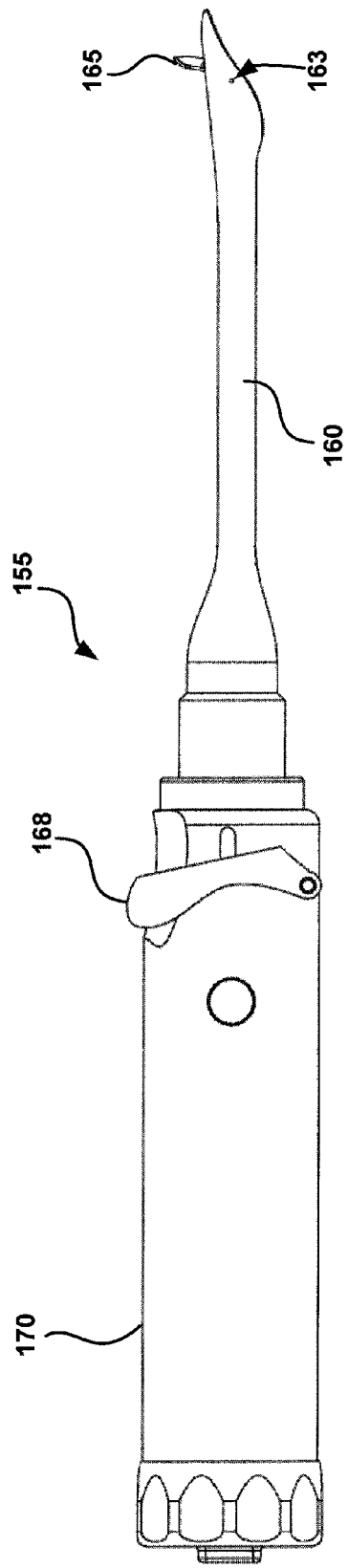
FIG. 7A
FIG. 7B

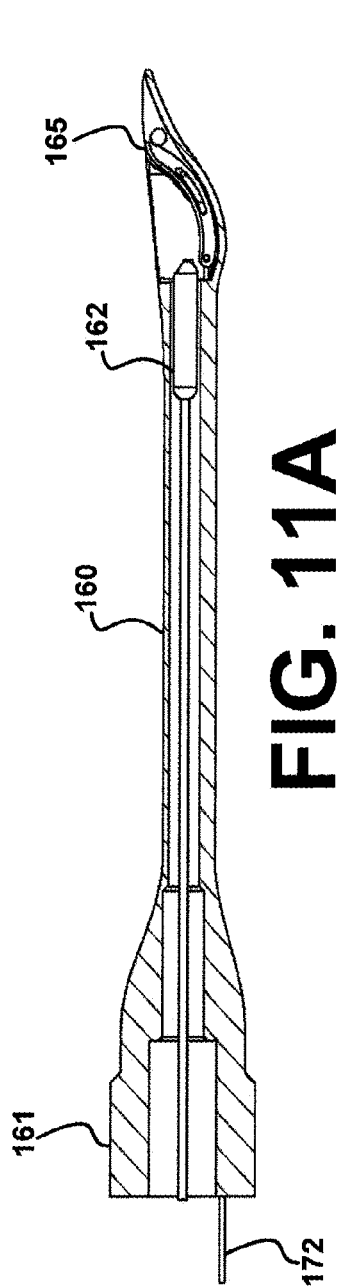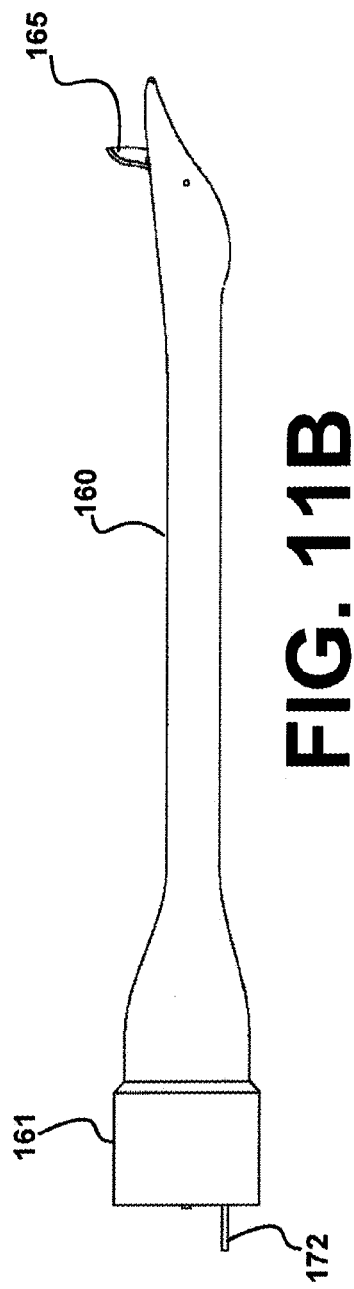

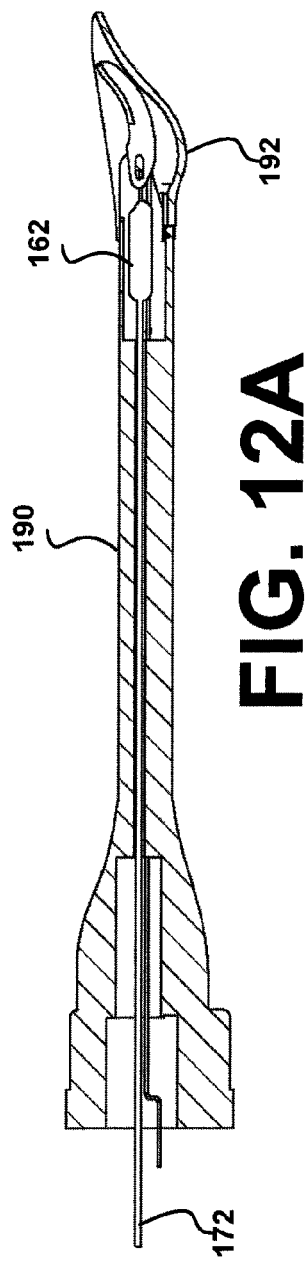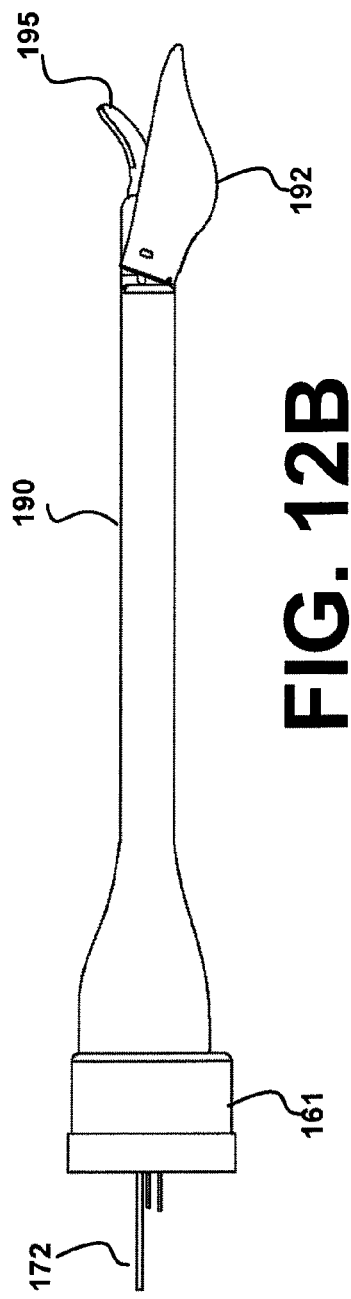

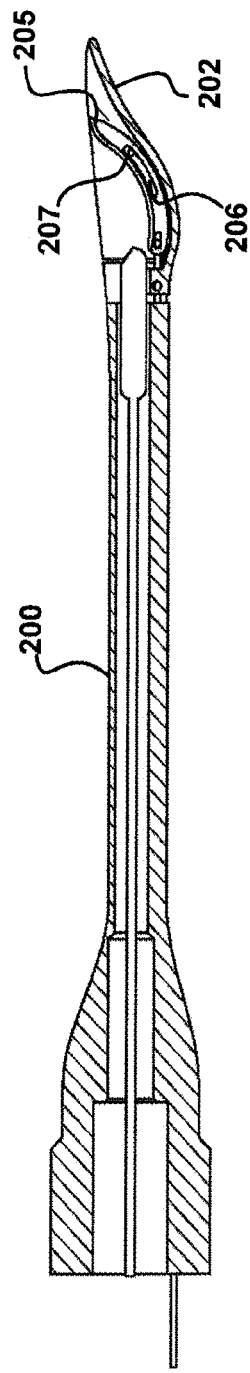
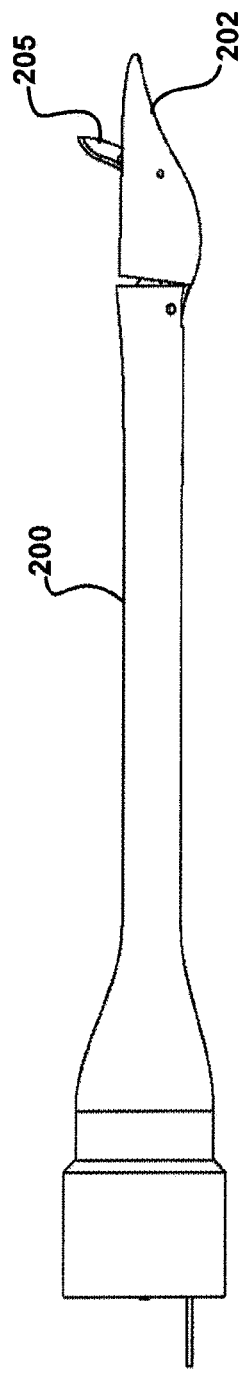
FIG. 13A
FIG. 13B

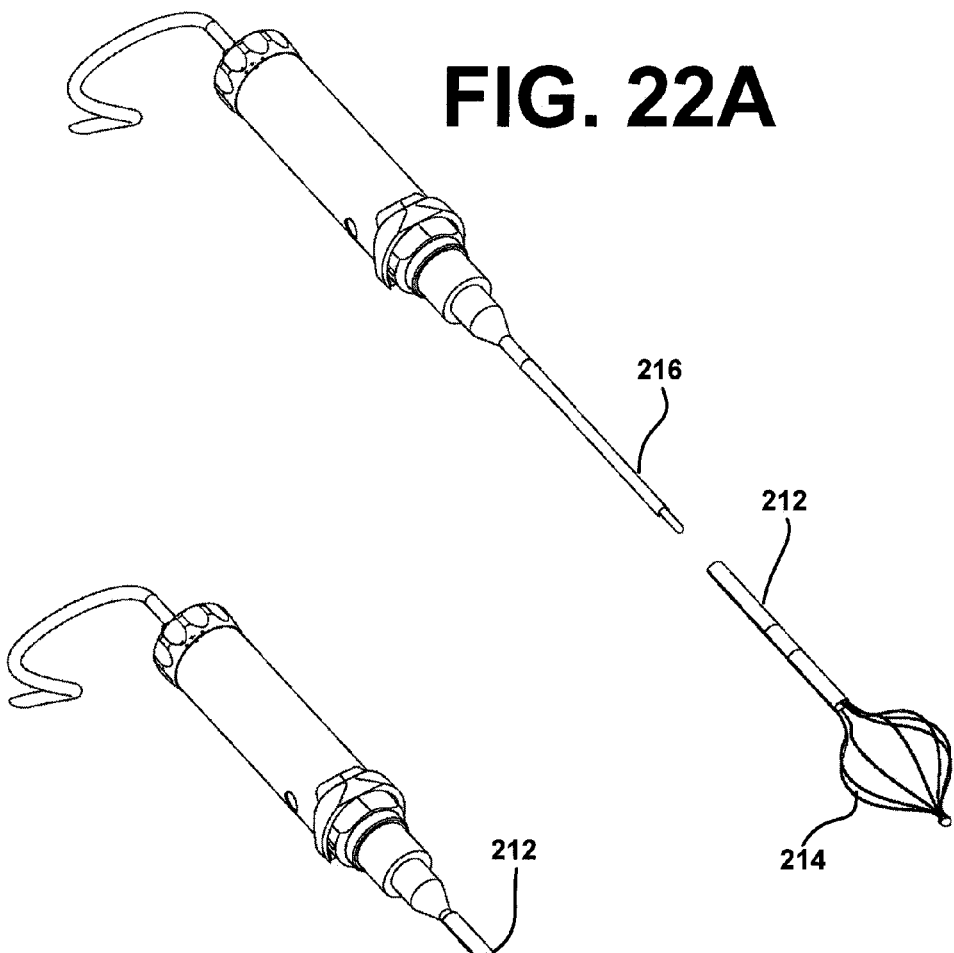

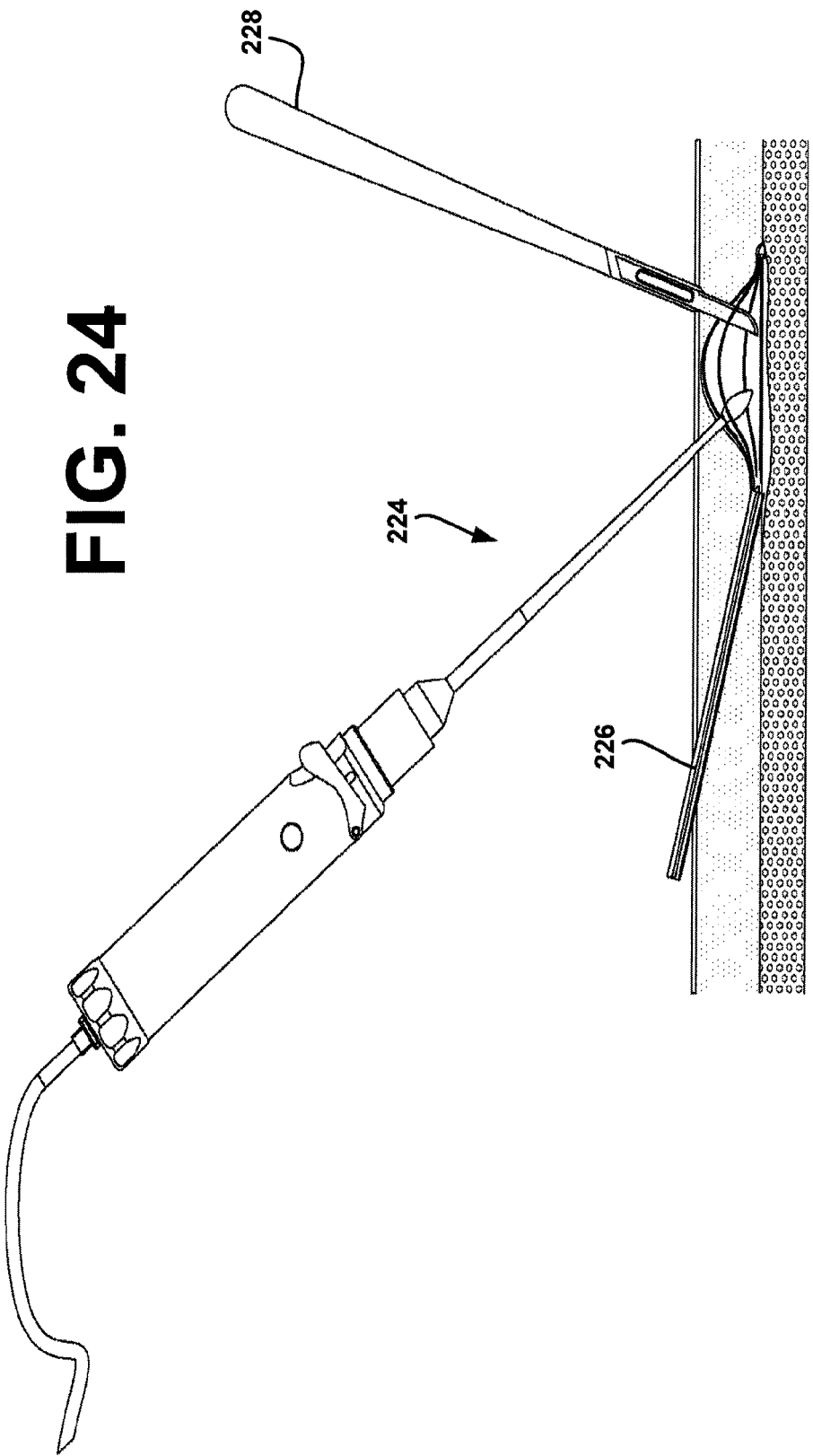

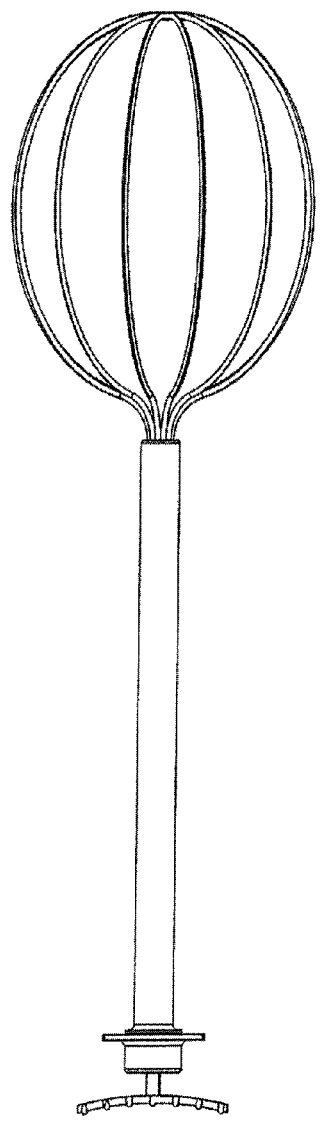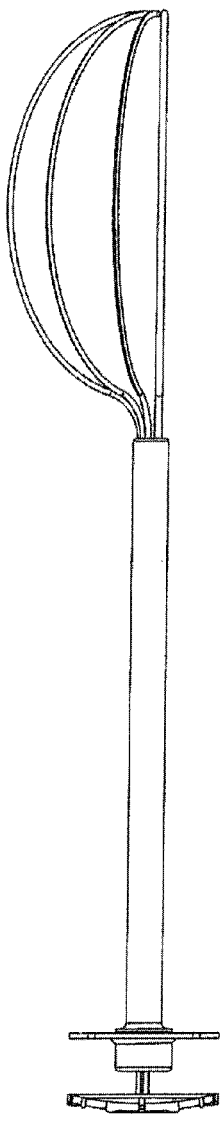
FIG. 29

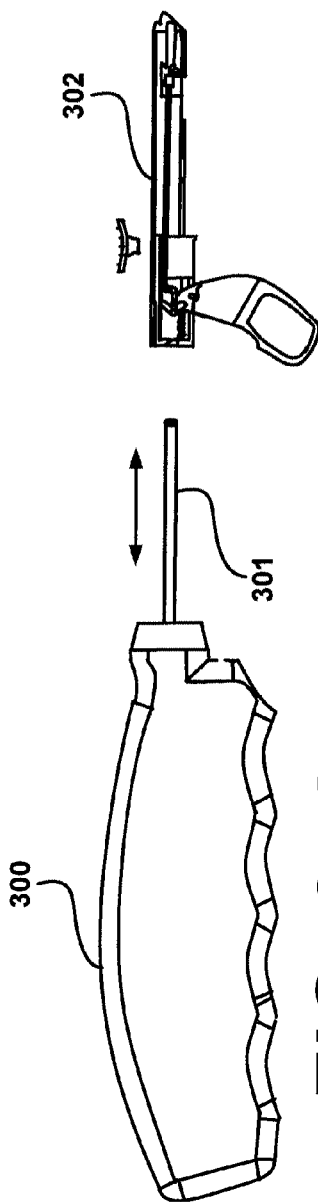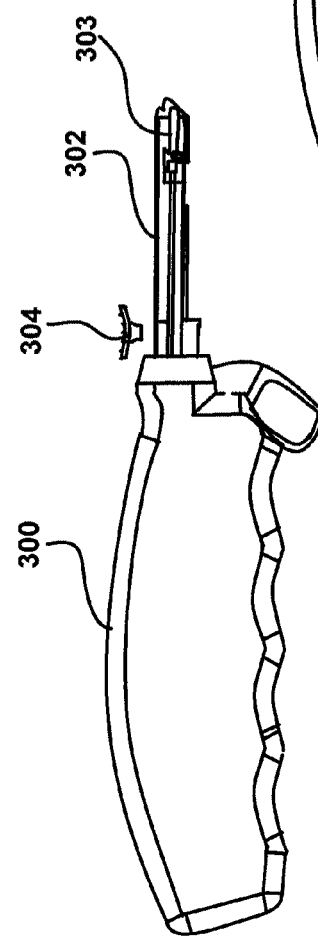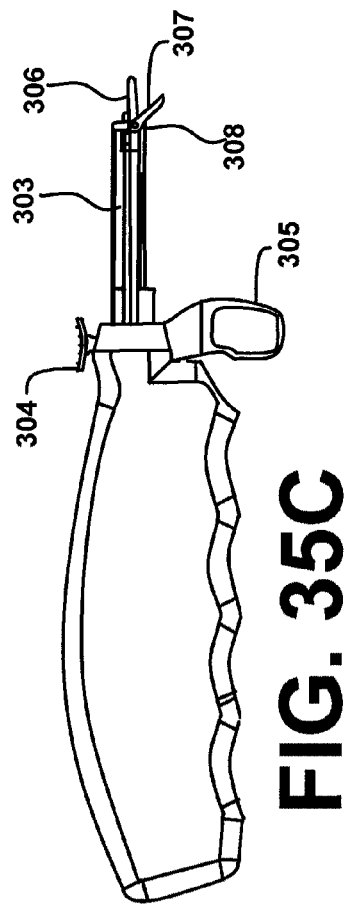
FIG. 35A
FIG. 35B
FIG. 35C

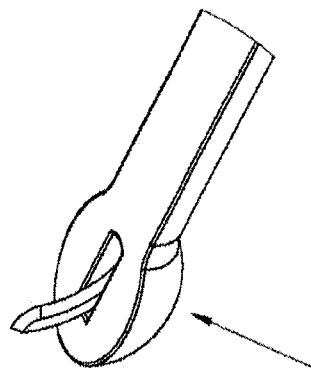
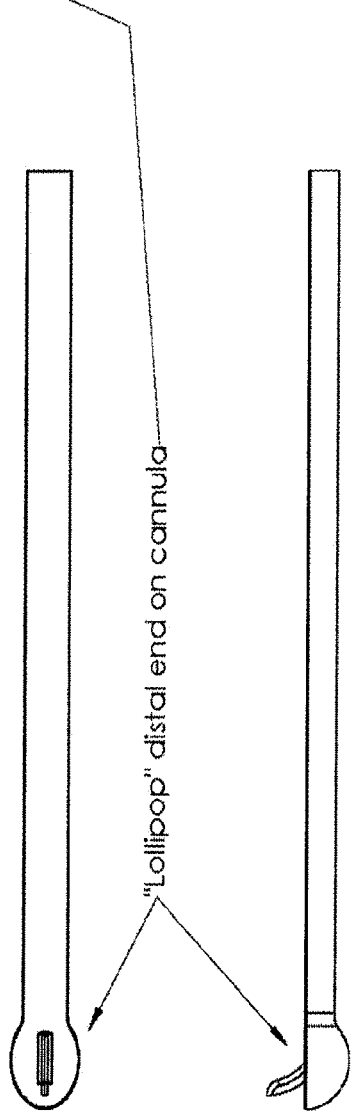
FIG. 41A
FIG. 41B
FIG. 41C
"Lollipop" distal end on cannula

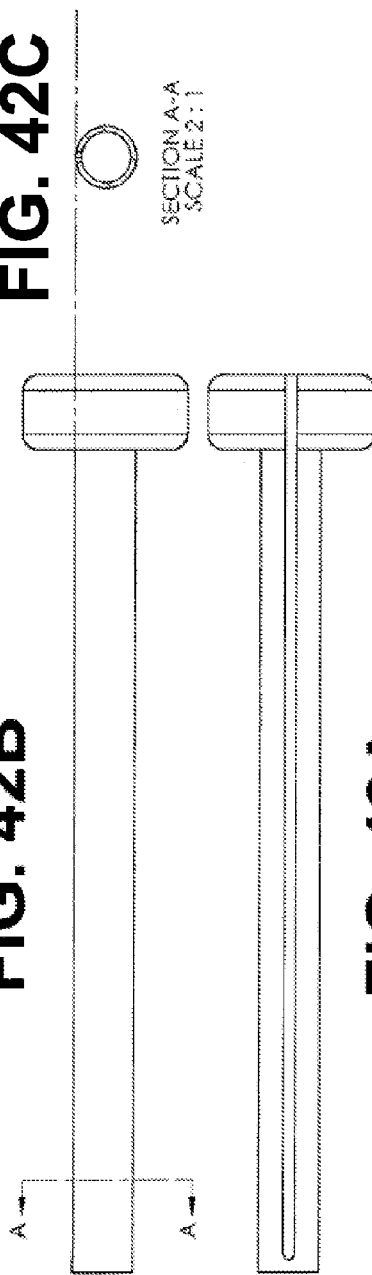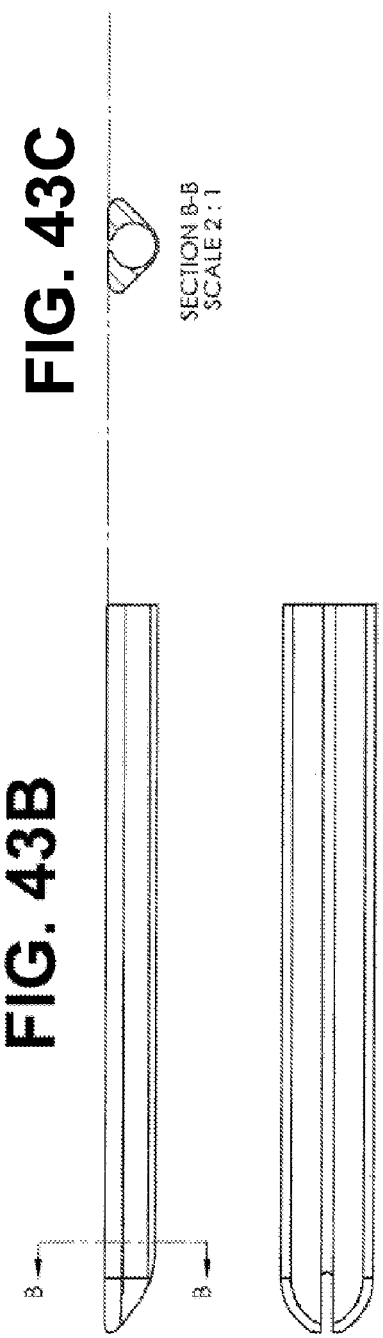

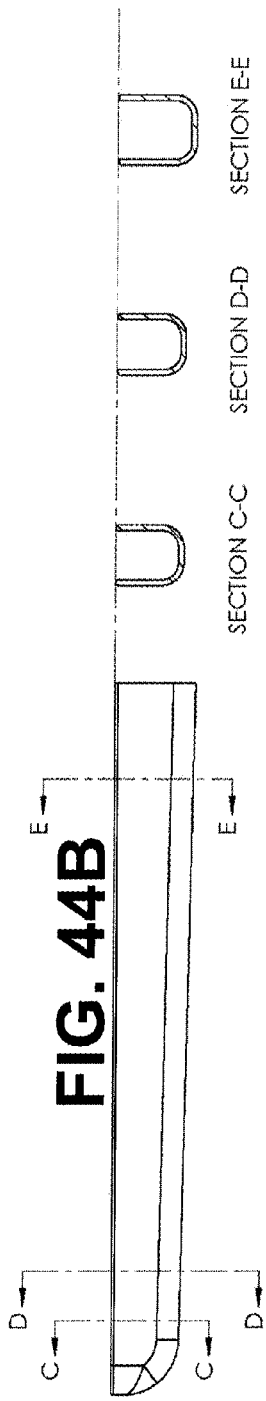
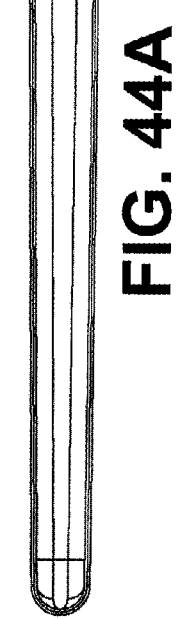
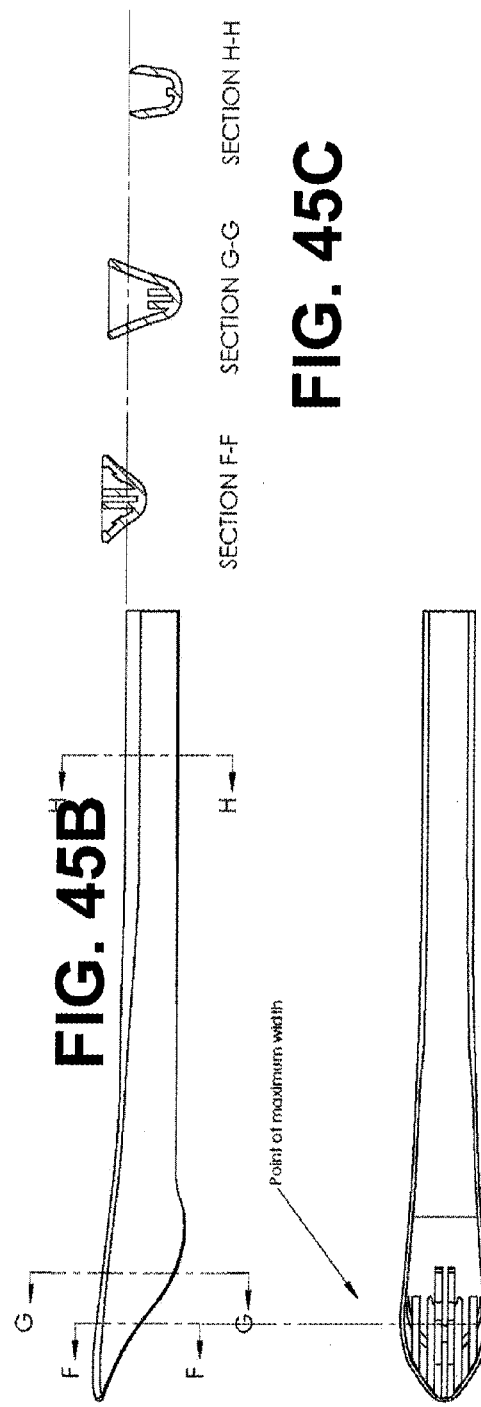
FIG. 44A  FIG. 44B  FIG. 44C
FIG. 45A  FIG. 45B  FIG. 45C

ENDO-SURGICAL DEVICE AND METHOD

CROSS-REFERENCE TO RELATED APPLICATION

The present application claims priority from the following provisional patent applications:

U.S. Patent Application Ser. No. 60/889,064, filed on Feb. 9, 2007, entitled METHOD AND APPARATUS FOR THE TREATMENT OF CARPAL TUNNEL SYNDROME;

U.S. Patent Application Ser. No. 60/969,484, filed on Aug. 31, 2007, entitled CANNULA APPARATUS AND METHODS FOR USE;

U.S. Patent Application Ser. No. 60/981,656, filed on Oct. 22, 2007, entitled ENDO-SURGICAL DEVICE AND METHOD;

U.S. Patent Application Ser. No. 60/983,436, filed on Oct. 29, 2007, entitled ENDO-SURGICAL DEVICE AND METHOD; and U.S. Patent Application Ser. No. 60/992,930, filed on Dec. 6, 2007, entitled CANNULA APPARATUS AND METHODS OF USE. The above-listed applications are being incorporated herein, by reference, in their entireties.

FIELD OF THE INVENTION

The invention relates to an endo-surgical device of the type including components such as tools, electronics and visualization components, and more particularly, to endo-surgical instruments for use in a system and method for minimally invasive endo-surgery.

BACKGROUND OF THE INVENTION

Systems and devices useful for performing endo-surgery are known. A number of devices have been developed for use in minimally invasive surgical procedures, including orthopedic and podiatric soft tissue surgeries such as nerve and tendon release procedures. In particular, certain devices have been developed for performing "carpal tunnel" surgery to relieve the symptoms of "carpal tunnel syndrome", in which the flexor retinaculum or "transverse carpal ligament" (TCL) is severed.

Carpal tunnel syndrome refers to numerous clinical signs and symptoms resulting from pressure on the median nerve inside the carpal tunnel. Splints that immobilize the wrist in a neutral position are the most commonly used nonsurgical treatment for carpal tunnel syndrome because an unbent wrist maximizes the size of the carpal tunnel, which reduces pressure on the median nerve. Physical therapy and special hand exercises are also used to relieve mild to moderate symptoms of carpal tunnel syndrome. However, when the symptoms persist or become intolerable, surgical decompression of the nerve by release of the transverse carpal ligament, or flexor retinaculum, is performed.

In early techniques, open carpal tunnel release surgery (OCTR) was performed to relieve carpal tunnel syndrome.

OCTR is typically performed under local anesthesia, where a longitudinal incision is made in the base of the palm and sometimes extending into the wrist. This incision opens the skin, subcutaneous fat, palmar fascia and palmaris brevis muscle to expose the transverse carpal ligament, which is cut with a surgical blade. The cut ligament springs open and immediately provides more space for the median nerve to pass through the carpal tunnel. The incision is then closed with sutures.

Although OCTR is currently the most commonly performed surgical carpal tunnel release procedure, it can lead to postoperative pain and morbidity lasting up to six months.

Recent advances involve endoscopic carpal tunnel release surgery (ECTR), which is performed as a single-portal technique or a double-portal technique. For a single-portal technique, one incision is made either in the palm or in the forearm proximal to the wrist. For a double-portal technique, two incisions are made, one in the palm and one in the forearm proximal to the wrist.

In 1987, the first reports of endoscope use in carpal tunnel release surgery were provided by Okutsu, a Japanese orthopedist. In Okutsu's technique, an incision is made 3 cm proximal to the distal wrist crease. Then, a clear plastic cannula is inserted into the carpal tunnel with an endoscope inside; under direct visualization, the transverse carpal ligament (TCL) is divided distally to proximally, with a hook knife.

The next development occurred in the early 1990's with John Agee and Francis King, who created a single-portal endoscopic carpal tunnel release system having a probe with a trigger-activated mechanism for engaging a blade to cut the TCL. The Agee technique involves activating the trigger mechanism to engage the blade and elevating it perpendicularly above the upper surface of the probe. The instrument is then withdrawn, and under direct visualization, the TCL is divided in a distal to proximal direction. The Agee systems and techniques are disclosed in Agee, et al. U.S. Pat. No. 4,962,770; U.S. Pat. No. 4,963,147; U.S. Pat. No. 5,089,000; U.S. Pat. No. 5,306,284; and U.S. Pat. No. 5,613,976.

Jay Menon created another single-portal technique involving a cannula with a D-shaped cross-section and an obturator. In Menon's technique, dilators are inserted through the antebrachial fascia into the carpal tunnel. Then, a cannula is passed under the TCL and a forward knife is used to cut the ligament proximally to distally while visualizing the TCL with an endoscope immediately following the knife.

Ather Mirza created yet another single-portal technique involving a cannula, a scope mounted cutting blade and a tapered obturator. The Mirza technique involves inserting an elongate insertion member through the cannula and introducing the combined cannula and insertion member under the TCL. Then, after advancing the obturator beneath the TCL, the scope mounted cutting blade is inserted through the cannula to operatively engage the tissue. Mirza's systems and techniques are disclosed in Mirza U.S. Pat. No. 5,366,465; U.S. Pat. No. 5,578,051; U.S. Pat. No. 5,968,061; and U.S. Pat. No. 7,041,115.

The first reports of double-portal ECTR were provided by James Chow in 1989, who developed a slotted cannula and obturator, synovial elevator, probes, and a series of knives for use in his technique. The Chow system is disclosed in U.S. Pat. No. 5,029,573. Then, in 1992, Michael Brown introduced an improved double-portal technique, where a slotted cannula is inserted in the carpal tunnel under the TCL and a surgeon's dominant hand is used to cut the ligament distally to proximally. The Brown system is disclosed in U.S. Pat. No. 5,323,765.

The ECTR procedures described above significantly reduced the postoperative pain, morbidity and recovery time associated with OCTR procedures.

However, there is a continuing need to improve ECTR and provide simple, workable systems and techniques that better protect the nerves and other portions of the hand during surgery. What is further needed is an improved, less cumbersome endo-surgical system that can be adapted for use with many other types of delicate endo-surgery, and not just for ECTR.

In the past, the performance of a minimally invasive surgical procedure, such as ECTR, has often required the use of a plurality of instruments for performing the procedure. For example, prior art surgical procedures often required the use of one or more dissectors, dilators, obturators, elevators or rasps to separate tissue and create a space for the visualization/cutting cannula, prior to its insertion and advancement in the body. Additionally, the visualization/cutting cannulas used in such prior art procedures, do not have any way to adequately inhibit nerves, tendons and other tissue from invading the surgical space defined by the cannula, as the same is advanced. As a result, these devices have an increased risk of severing unintended tissue The particular shape of the prior art cannulas can have an impact on the particular procedure being performed. For example, certain prior art cannulas having a uniform cross-section or a taper (i.e., a reducing width) towards the distal end, do not provide the surgeon with tactile feedback indicating when the carpal tunnel has been traversed and the distal edge of the TCL has been reached. Additionally, some prior art cannulas tend to be somewhat narrow relative to the width of the carpal tunnel. This narrowness allows significant displacement of the cannula relative to the center line of the TCL, thus increasing the risk of coming into contact with, or even severing, tissues which the surgeon does not intend to cut. For example, FIG. 15 shows a narrow, prior art cannula that has displaced within the carpal tunnel, such that its knife is potentially endangering the ulnar nerve and/or artery.

Further, cannulas exist having a circular, "D" or "U" shaped cross section, that permit rotation of the cannula around its longitudinal axis. However, when a blade or knife is deployed in connection with such a cannula, any inadvertent rotation of the cannula further increases the risk of severing tissues which the surgeon does not intend to cut. For example, FIG. 16 shows a prior art cannula that has inadvertently rotated such that its knife is potentially endangering the ulnar nerve and/or artery.

Additionally, certain cannulas used for endo-surgical procedures, such as a carpal tunnel release procedure, have been provided with a flat upper surface at the distal end, continuous with the upper surface of the cannula shaft. This flat upper surface does not adequately displace the fat pad that lies beyond the distal edge of the TCL, thus making it difficult for the surgeon to visualize the location where division of the TCL should begin.

Further, prior-art devices possess blades that are deployed by articulating into an inclined position and that decline to a closed position. This trajectory can cause loose tissue to be pinched between the blade and certain other features of the cannula. The pinched tissue may then prevent the blade from being fully closed, leaving it partially exposed in an unsafe position.

What is needed is a cannula for an endo-surgical procedure wherein the shape of the cannula has been optimized to aid the surgeon in cutting only those tissues that the surgeon intends to cut. What is additionally needed is a cannula, the shape of which provides the surgeon with useful tactile feedback while performing a minimally invasive endo-surgical procedure. What is further needed is a cannula that encompasses various surgical steps, and thereby eliminates the need for a plurality of tools, be it for separating tissue, clearing a surgical space prior to insertion of the cannula, or otherwise.

SUMMARY OF THE INVENTION

It is accordingly an object of the invention to provide an endo-surgical device, system and method that overcomes the above-mentioned disadvantages of the heretofore-known devices, systems and methods of this general type.

What is provided is a tool for performing an endo-surgical procedure. One particular embodiment includes a flared prow that provides the surgeon with tactile feedback and limits the displacement and rotation of the cannula and keeps the surgical instrument away from tissues that are not intended to be affected. The endo-surgical tool can be utilized as part of a system for performing different endo-surgical procedures.

Other features which are considered as characteristic for the invention are set forth in the appended claims.

Although the invention is illustrated and described herein as embodied in a particular type of endo-surgical device and method, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

Like reference numerals refer to like items throughout the drawings.

FIG. 3A is a perspective view of an endo-surgical system in accordance with another particular embodiment of the instant invention.

FIG. 3B is a perspective view of an endo-surgical system in accordance with a further particular embodiment of the instant invention.

FIG. 7A is a side, partial cross-sectional view of an endo-surgical device with the blade at rest, in accordance with one particular embodiment of the present invention.

FIG. 7B is a side view of an endo-surgical device with the blade deployed, in accordance with one particular embodiment of the present invention.

FIG. 11A is a cross-sectional view, taken from the side, of a fixed prow, single-action cannula, in accordance with one particular embodiment of the present invention, having its blade at rest.

FIG. 11B is a side view of a fixed prow, single-action cannula of FIG. 11A, having its blade deployed.

FIG. 12A is a cross-sectional view, taken from the side, of a drop-prow, single-action cannula, in accordance with one particular embodiment of the present invention.

FIG. 12B is a side view of the single action cannula of FIG. 12A, having its prow dropped.

FIG. 13A is a cross-sectional view, taken from the side, of a double-action cannula, in accordance with one particular embodiment of the present invention.

FIG. 13B is a side view of the double-action cannula of FIG. 13A, having its prow dropped and its blade deployed.

FIGS. 17A-17C show a technique for performing an ECTR using a cannula according to an embodiment of the subject invention, wherein FIG. 17A shows insertion, FIG. 17B shows retraction, and FIG. 17C shows ligament division.

FIGS. 19A-19C show a technique for performing an ECTR using a cannula according to another embodiment of the subject invention, wherein FIG. 19A shows insertion, FIG. 19B shows deployment, and FIG. 19C shows ligament division.

FIGS. 22A-22B show another particular embodiment of an endo-surgical device including a tool for use in accordance with the present invention.

FIG. 24 show the use of another particular endo-surgical instrument in accordance with another embodiment of the present invention.

FIGS. 25-34 show particular embodiments of an inventive spreader device and assembly that can be used in connection with different embodiments of the present invention.

FIGS. 35A-35C show another particular embodiment of an endo-surgical device including a tool for use in accordance with the present invention.

FIG. 41A is a partial, isometric view of a cannula of one particular embodiment of the present invention.

FIG. 41B is a plan view taken from the top of a cannula in accordance with one particular embodiment of the present invention.

FIG. 41C is a plan view taken from a side of the cannula of FIG. 41B.

FIGS. 42A, 42B and 42C show, respectively, a top, front and cross-sectional view of a first prior art.

FIGS. 43A, 43B and 43C show, respectively, a top, front and cross-sectional view of a second prior art.

FIGS. 44A, 44B and 44C show, respectively, a top, front and cross-sectional view of a third prior art.

FIGS. 45A, 45B and 45C show, respectively, a top, front and cross-sectional view of a particular embodiment of the current invention.

DESCRIPTION OF THE PREFERRED EMBODIMENTS

Figure 1:
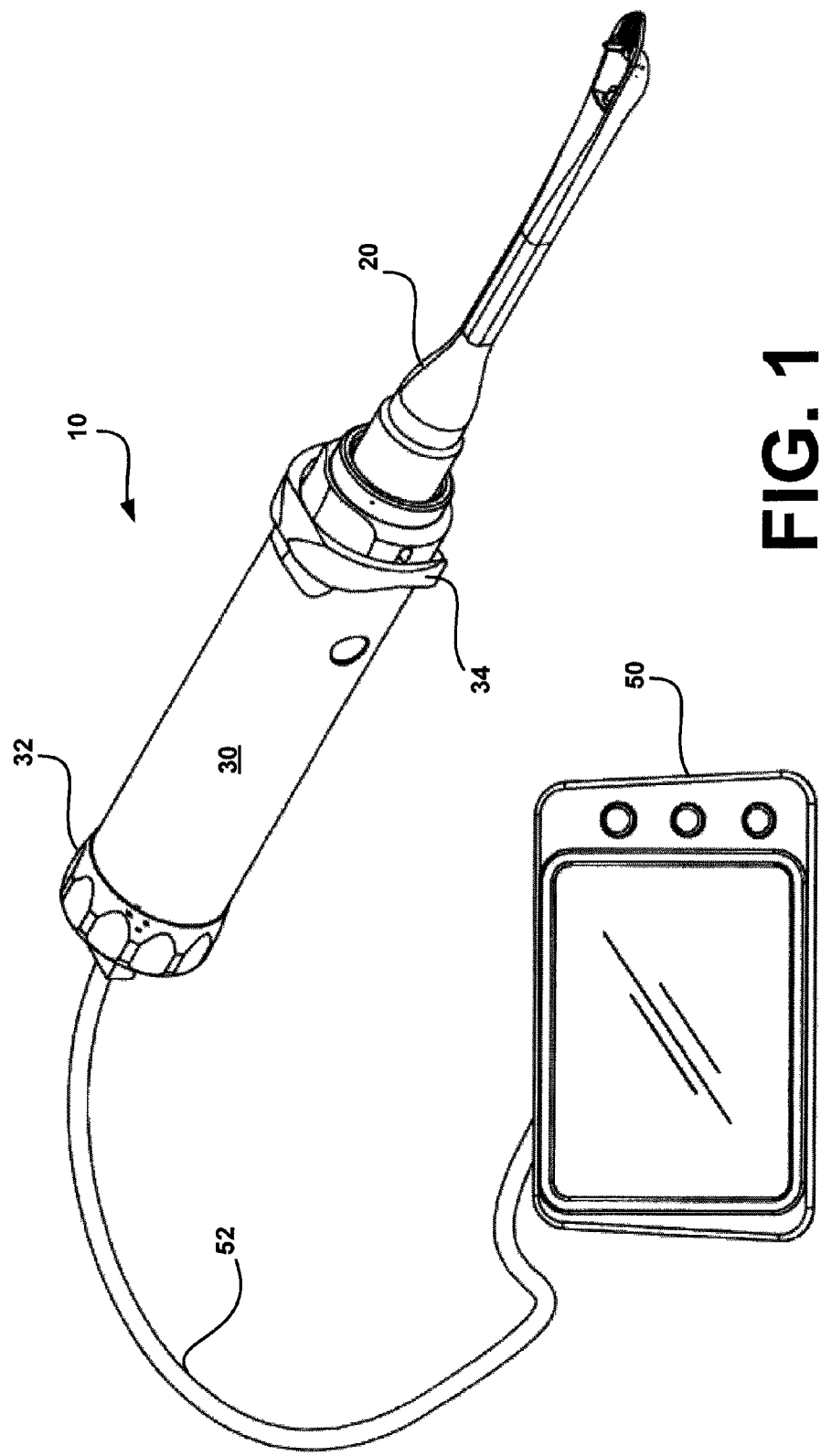
FIG. 1 is a perspective view of an endo-surgical system in accordance with one particular embodiment of the instant invention.

Referring now to FIGS. 1-4D, there is shown a surgical system 10 for minimally invasive, minimally encumbered endo-surgery in accordance with particular embodiments of the instant invention. As will be discussed more particularly below, the endo-surgical system 10 includes a cannula 20, a handle or handpiece 30, an electronics module (EM) 40 and a display 50.

The cannula 20 of system 10 includes a straight, angled or curved, rigid shaft that is designed for a specific surgical, therapeutic and/or diagnostic purpose. In some embodiments, the cannula 20 can be disposable and, in others, it may be sterilized for reuse. In the present system, the cannulas are designed to be procedure-specific (i.e., each is individually designed for a specific visualization and/or surgical procedure). For example, in one particular embodiment for the endoscopic carpal tunnel release procedure, a cannula 20 is provided that has a curved (or angled) distal end that protrudes from its main body. This curved distal end facilitates tactile identification of the distal edge of the transverse carpal ligament (TCL) and is capable of displacing a fat pad located distally of the TCL to allow clear visualization of the distal edge of the TCL before dividing the TCL.

In the system 10, a desired cannula 20 can be attached to and/or detached from a sterile or sterilizable light-weight handle 30. As with the cannula 20, the handle 30 can be disposable or, if desired, can be capable of being re-sterilized for re-use. The ability to detach the cannula 20 from the handle 30 also permits different cannulas 20, (i.e., each adapted for different surgical procedure) to be used on a single, universal handle 30. When attached, the cannula 20 is mechanically coupled to the handle 30.

In order to permit visualization of the surgical procedure at the surgical site, the cannula 20 includes at least a portion of an optical or electronic imaging device, as defined further below. In one preferred embodiment, another portion of the imaging device is incorporated into an electronics module 40. The electronics module 40 is located within the handle 30. For example, in one particular embodiment, the handle may be hollow and adapted to receive the electronics module 40. Because the electronics module 40 is accepted into the sterile/sterlizable handle 30, the electronics module 40 may be non-sterile and reusable.

Upon insertion of the electronics module 40 into the handle 30, the handle is sealed with the sterile cap 32, isolating the non-sterile electronics module 40 from the sterile surgical field. Once the system 10 is assembled (i.e., the electronics module 40 is inserted into the handle 30, sealed with the cap 32, and the cannula 20 attached at the distal end), the electronics module 40 becomes connected to the cannula 20.

The images obtained by the imaging device of system 10 are processed and displayed on a display 50, which will be discussed more particularly below. The display 50 may be attached to the handle 30, or detached, but located within or close to the sterile surgical field. Additionally the display 50 can be tethered to the electronics module 40 to receive image information obtained by the imaging device in the cannula. Alternately, the display 50 can receive image information wirelessly from the electronics module 40. Images obtained by the imaging device in the cannula and processed by the electronics module can be displayed on the display 50, so that the surgeon can visualize an image of the surgical procedure substantially in-line with, and without having to significantly shift his/her gaze from, the surgical field.

As discussed above, the handle 30 can accept a variety of different cannulas 20 used for different surgical procedures, while being serviced by essentially the same electronics module 40 and display 50.

In an alternate embodiment (FIG. 4D), the cannula 20 and the handle 30 are built into one single disposable unit and the electronics module EM 40 is located outside of the handle and connected to it by means of a cable connection. Furthermore, the electronics module 40 and display 50 may be linked together and sealed within an sterile enclosure 60 suitable for location within the sterile surgical field. Alternatively, the display, with or without the electronics module may be sterilizable.

Each of the parts of the system 10 will be described in more detail, herebelow.

The Cannula:

A. Cannulas for Endo-Surgical Procedures.

As discussed above, the present invention relates to a surgical system and instruments for minimally invasive endo-surgery, which can be used within the sterile surgical field. This field encompasses orthopedic and podiatric soft tissue surgeries such as nerve and tendon release procedures. Also, the field of endo-surgery, and for use of the present inventive device, includes plastic surgery procedures such as endoscopic face lifts and general or vascular surgery procedures, such as saphenous vein harvesting as well as others. As such, the cannula of the present invention can be adapted to the specific endo-surgical procedure it is designed to perform, so as to facilitate initial soft tissue separation or dissection by imparting to it a specific geometry at its shaft and at its distal end. Each cannula useful with the instant invention may also be designed to perform surgical manipulation of the tissues and other therapeutic purposes using procedure-specific tools.

Figure 9C:
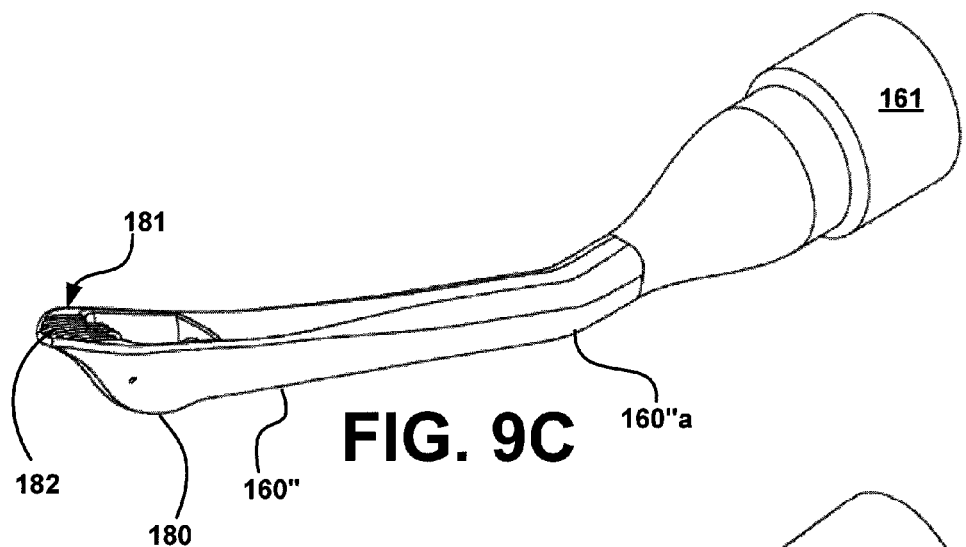
FIGS. 9A-9C show straight, curved and angled cannulas with prow shaped distal end geometry that are particular embodiments useful with the present invention.
Figure 9B:
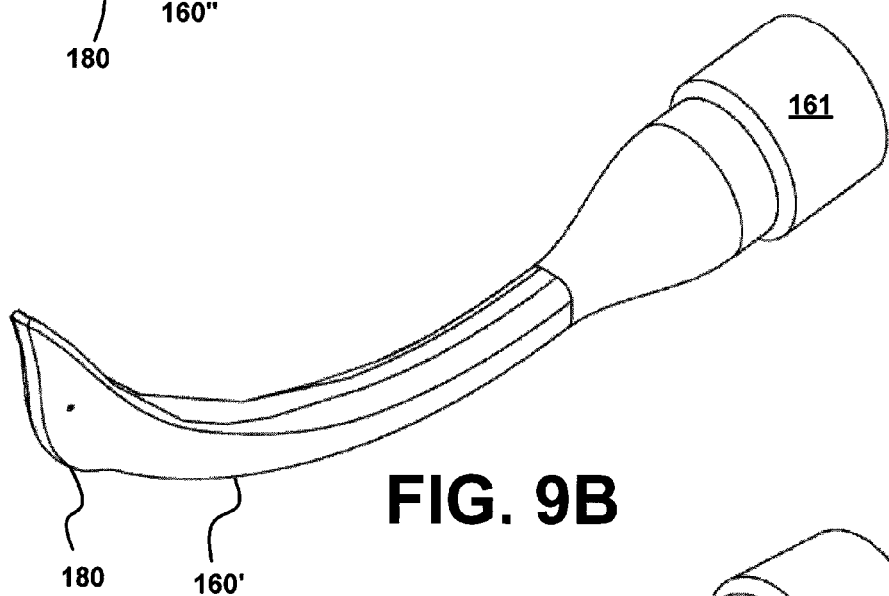
Figure 9A:
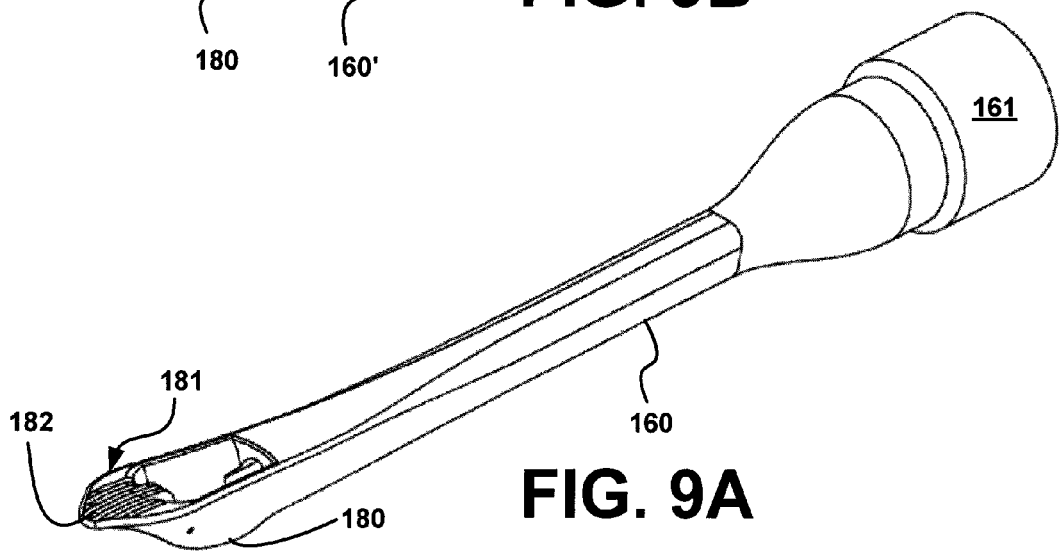

For example, as shown in FIGS. 9A-9C, the cannula 20 is rigid but can have a straight, angled or curved shaft; it is introduced into the human body through either a small incision or through percutaneous means to allow visualization and/or diagnosis and/or surgical and/or therapeutic manipulation of the tissues.

Visualization can be provided by an "imaging device", which can include an image sensor (CMOS, CCD, FOVEON, or similar device) and lens, at least a portion of which is located close to the distal end of the cannula. Additionally, a transparent housing may encapsulate the lens and sensor or the lens can be molded into the transparent housing. Alternately, the imaging device can be an optical endoscope originating in the handle and passing through a lumen in the cannula.

The imaging device can also include illumination, which may be provided by either LED's located close to or at the distal end of the cannula (preferred embodiment), or by fiberoptic or light pipe transmission from a light source in the handle. If desired, the fiberoptic may be integral to an endoscope or the cannula, itself, may serve as the light pipe.

The cannula may also house and allow the deployment of one or more surgical tools or instruments such as a knife, scissor, tissue spreader or other device to allow the surgeon to perform manipulation of the tissues or other diagnostic or therapeutic procedures.

In one embodiment disclosed below, the entire procedure can be performed with a single cannula without the need for other instruments. In an alternate embodiment a separate surgical instrument may be used in conjunction with a cannula that is intended solely for visualization (i.e., without tools that allow separation, dissection or surgical manipulation of tissues).

Further, in a preferred embodiment discussed herein, the cannula is designed to be detachably connected to the handle. Upon attachment, the cannula becomes mechanically coupled to the handle and optically or electrically connected to the electronics module contained within the handle.

As such, a tool kit can be provided that includes a single handle, electronic module and display, but also a plurality of different cannulas adapted for different surgical, therapeutic or diagnostic procedures.

The cannula may be reusable or disposable. If disposable, the cannula comes sterile within a pack and is intended to be used only once and discarded.

The cannula may include one or more actionable triggers, levers or buttons to operate the tools that may have been provided.

Alternatively, some or all triggers, levers or buttons may be included in the handle.

Additionally, the cannula and/or the handle can be provided with one or more mechanisms, such as levels, bubbles or transverse wings or pegs, to aid in indicating rotational position of the cannula.

B. Exemplary Cannulas Adapted Specifically for an Endoscopic Carpal Tunnel Release (ECTR) Procedure.

In one particular example of the system of the present invention, the system will be described in connection with a cannula designed specifically to perform an endoscopic carpal tunnel release surgical procedure. The ECTR cannula of the present invention is intended to be used as a single instrument expressly designed to perform all of the following functions: (i) separate the synovium and/or other tissue from the TCL; (ii) inhibit tendons, nerves or other tissue from invading the surgical space defined by the cannula as the cannula is advanced; (iii) encourage the cannula to self-center within the carpal tunnel as the cannula is advanced; (iv) inhibit the rotation of the cannula within the carpal tunnel; (v) provide tactile feedback to the surgeon at the moment when the carpal tunnel has been fully traversed and the distal edge of the TCL has been reached; (vi) displace the fat pad found beyond the distal edge of the TCL to permit good visualization of the location where division of the TCL should begin, and (vii) execute the division of the TCL, without damaging other tissue.

Figure 5A:
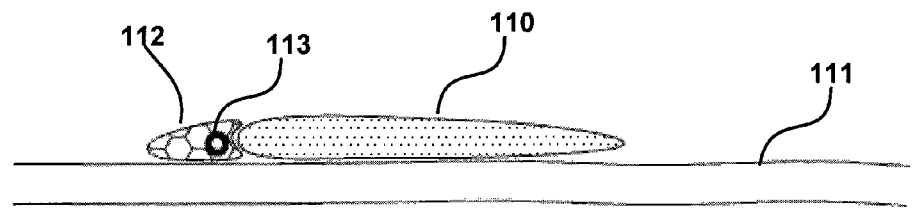
FIG. 5A shows the typical anatomy of a portion of a hand.
Figure 5B:
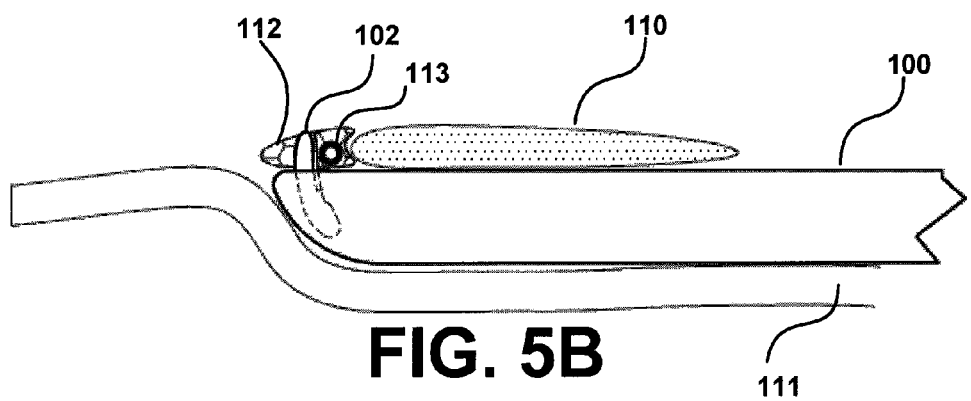
FIG. 5B shows a prior art cannula and the anatomy of the portion of the hand.
Figure 5C:
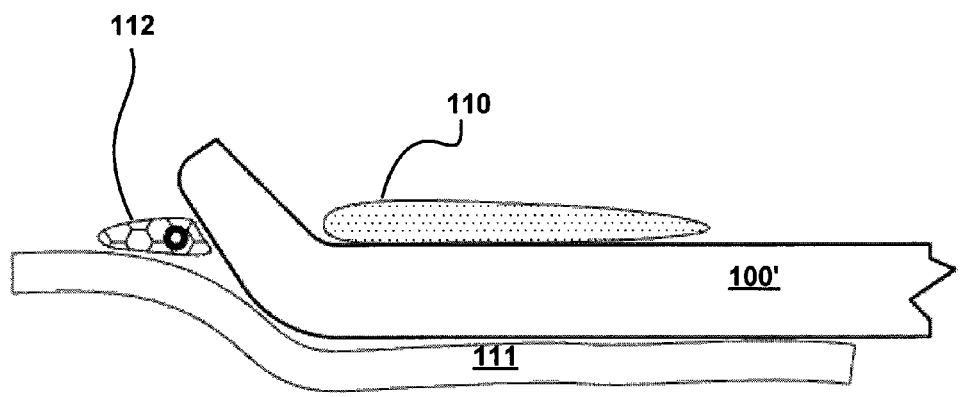
FIG. 5C shows a cannula with a curved prow in accordance with one particular embodiment of the subject invention and the anatomy of the portion of the hand.

Traditional endoscopic carpal tunnel release methods use a straight cannula. However, a straight cannula has certain limitations with respect to the anatomy of the hand being operated. FIGS. 5A-5C show a comparison of the effects of using a curved cannula, in accordance with one particular embodiment of the invention, and with a straight cannula, as per the prior art. In particular, referring to FIG. 5A, the typical anatomy of a hand in the region of the transverse carpal ligament 110 is shown to include a synovial or fat pad 112 within which important arteries and nerves 113 can be found. The ligament 110 tends to be airfoil shaped. When a prior art straight cannula 100 (i.e., the tip being in the same plane as the shaft) is inserted into the patient's hand between the tendon/nerve 111 and the ligament 110, the cannula 100 may travel under the fat pad 112. The straight cannula 100 does not allow for good visualization of the distal edge of the ligament 110 because of the interposition of the fat pad 112. This may cause an incision of the fat pad 112 when the knife 102 is deployed, as shown in FIG. 5B possibly severing the arteries and/or nerves within.

In contrast, as shown in FIG. 5C, a cannula 100' with a curved-tip 104 according to embodiments of the subject invention is capable of displacing fat pad 112. By displacing fat pad 112, a cannula 100' incorporating a curved-tip 104 can provide a clear view of the edge of the ligament 110. An angled-tip can be used in place of the curved-tip 104. This angled or curved tip will hereafter be referred to as the "prow". Note that, as used herein, references in the specification and the claims to the "curved-tip" and "angled-tip", or "curved end" and "angled end", of the cannula are interchangeable and are not intended to be exclusive of any embodiments that might fall under one term or the other. Rather, as will be readily understood by the skilled artisan, whether the distal end of the cannula protrudes upward as a result of a relatively abrupt angle or a more gradual curve, it will facilitate displacement of the fat pad, and is thus within the scope of the subject invention.

Additionally, certain embodiments of the subject invention will be described as having a curved tip, which, for purposes of the present application means that the distal tip of the prow is above the top surface of the cannula (i.e., in a different plane that lies above the plane of the top surface of the cannula's shaft) when the prow is in its resting position. In addition, the configuration of the prow facilitates identification of the far edge of the TCL by providing tactile feedback that the TCL has been crossed, a characteristic not seen in the prior art.

Figure 6:
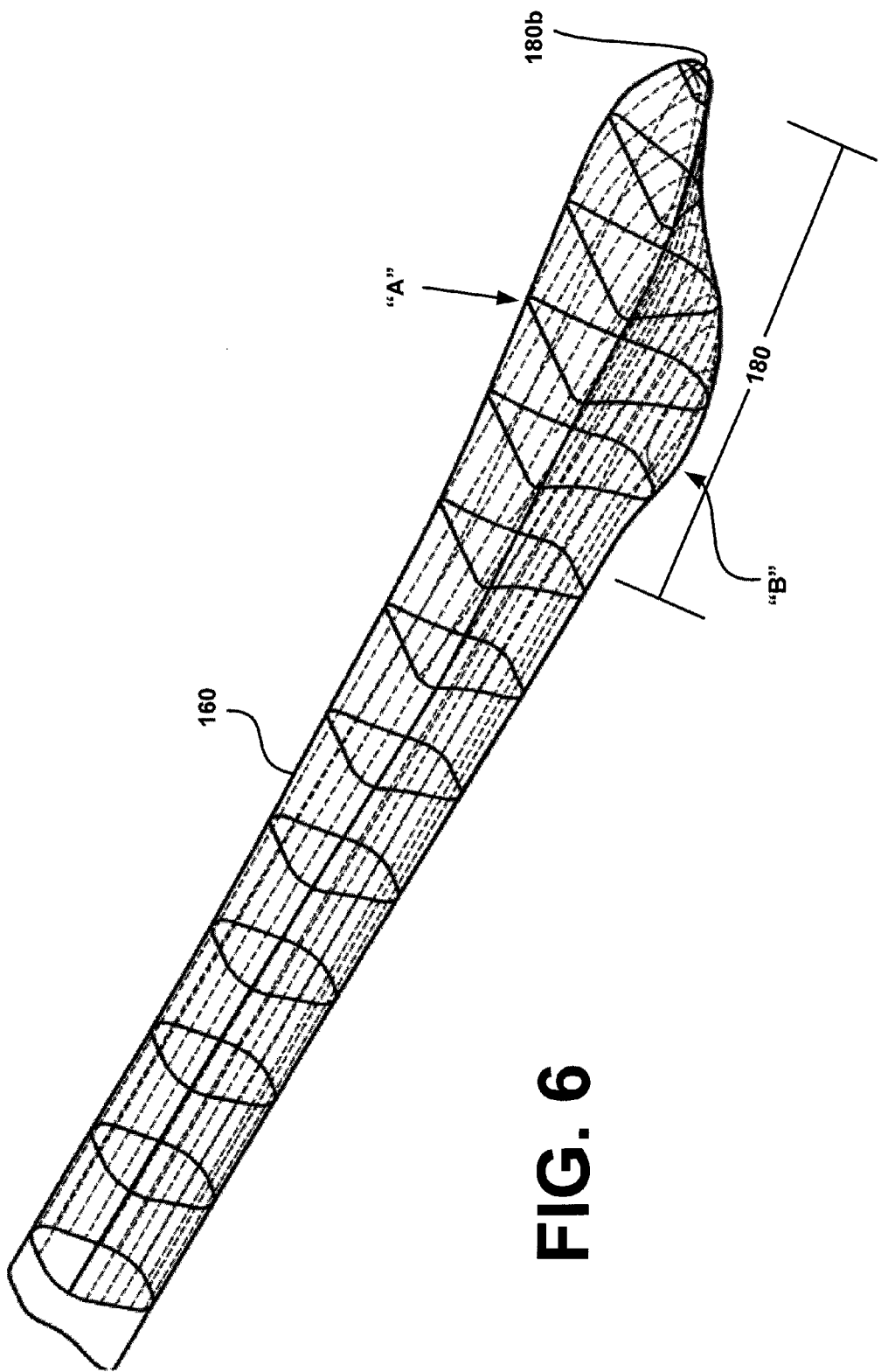
FIG. 6 shows a perspective drawing of a cannula with a prow shaped geometry at the distal end in accordance with another preferred embodiment of the present invention.

More particularly, referring now to FIG. 6 of the instant application, there is shown one particular preferred embodiment of a cannula including a flared prow, not unlike that of an ocean going ship with a high freeboard. As can be seen from FIG. 6, the upper edges of the prow 180 of the cannula 160 gradually diverge, reaching a maximum width at point "A", and then, gradually converge towards the distal end 180b. The maximum width of the prow 180 at the point "A" is greater than the width of the shaft of the cannula 160. The width of the prow is also greater than the height of the prow at point "A". Additionally, the flared prow 180 of the cannula is open at the top, between a portion of the upper edges, such that the walls and bottom of said prow define a bowl or cavity, therebetween.

As the cannula is advanced, it is this flared prow 180 that cleanly and clearly separates synovium and/or other tissue from the TCL and inhibits the invasion of nerves, tendons and other tissues into the surgical space defined by the cannula. As can be seen from the drawings, and more particularly, from FIG. 6, the cross-section of the flared prow 180 is shaped like an inverted bell and, being relatively wide, occupies more space within the carpal tunnel than prior art devices. Since the greater width inhibits the lateral displacement of the prow in the confined space of the carpal tunnel, there is a greater assurance that the center line of the cannula 160 will tend to coincide with the center line of the carpal tunnel, minimizing the risk of a displacement that could lead to injuring the ulnar nerve and/or artery which lie on the hamate side of the tunnel. Upon reaching the distal edge of the TCL, the flared prow 180 also displaces the fat pad exposing the distal edge of the TCL to visualization by the surgeon.

Additionally, as shown in FIG. 6, the upper edges of the cannula 160 become more flared as distal end 180b is approached. The top surface of the prow 180 curves upward, whereas the bottom surface of the prow 180 projects downward. Seen on a longitudinal section, the top surface of the prow 180 is curved or angled upwards so that it mostly lies above the projected upper surface of the shaft of the cannula while the lower surface of the prow projects downwards so that its bottom lies below the bottom surface of the shaft, as shown at point "B". This geometry, in combination with the geometry described in the previous section, makes the prow bulbous, not unlike a lollipop. In other words the short, distal-most portion of the cannula has a greater cross-sectional area than the longer, more proximal part, which has a smaller cross-section. Since carpal tunnel syndrome is a form of compartment syndrome, or disorder caused by increased tissue pressure, this design feature provides the surgeon with a propioceptive or tactile feedback effect that informs him that he has traversed through the area of increased pressure or disease condition, and helps the surgeon determine the proper depth of insertion of the instrument before initiating the division of the TCL. FIGS. 41A-41C show one particular embodiment of a cannula of the present invention having a geometry suitable for creating the above-described "lollipop" effect during use. Note that in the device in accordance with the present invention shown in FIG. 45, contrary to the prior art cannulas shown in FIGS. 42-44, the short, distal-most portion of the cannula has a greater cross-sectional area than the longer, more proximal part, which has a smaller cross-section.

The above-mentioned feature of the invention is useful in either distal to proximal surgical divisions, as well as proximal to distal surgical divisions.

Further, in particular embodiments of the invention, as shown more particularly in FIGS. 7A, 7B, 9A and 9C, the upper surface 181 of the prow 180 of the cannula has an increased flat contact area, which, optionally, includes the ribs 182, extending between the prow 180 and the TCL of the patient. The ribs 182, which are closely spaced in the present preferred embodiment, also prevent the resting (i.e., not yet deployed) knife from unintentionally cutting tissue that may project into the cavity. This flat or ribbed surface also inhibits the rotation of the cannula around its longitudinal axis in such a way that the knife, when later deployed, will do so on a plane perpendicular to the surface of the TCL to be divided. The flat contact area also prevents the prow 180 from snagging with the multiple fibers of the TCL upon insertion and advancement by the surgeon.

Referring now to FIGS. 7A-13B, there are shown a plurality of preferred embodiments of an endo-surgical device for use in ECTR wherein the prow is curved or angled relative to the shaft of the cannula (i.e., the tip of the prow being above the plane defined by the upper surface of the cannula shaft) and incorporates a flared prow. As described herein, each cannula can be specifically adapted to a particular application, which, in the present embodiment, is ECTR.

More particularly, FIGS. 7A and 7B are side views of an endo-surgical device 155 in accordance with one particular embodiment of the present invention. The device 155 includes a handle 170 with a detachable cannula 160 connected thereto. The cannula 160 is a curved-tip cannula (i.e., the distal surface 163 being above the upper surface of the shaft 169), wherein the blade 165 is deployed by pulling a mechanical actuator 168 which causes the knife to project above the cavity. Note that the cannula 160 can include an imaging assembly (162 of FIGS. 7A-7B) in communication with an EM module, all or portions of which may be located in the handle 170, as discussed in connection with FIGS. 1 and 2, above, or can include an optical endoscope (167 of FIG. 4B or 8D), of a type known in the art.

In the instant example, the prow 180 of the cannula 160 is fixed (i.e., does not drop) and the actuator 168 is connected by a linkage and rod (172 of FIGS. 8B-8D) to the proximal end of the blade 165. The blade 165 is fixed at a pivot point 166 to the distal end of the cannula 160. Thus, the blade 165 can be deployed in an arcuate (i.e. curvilinear) path from the cavity in the prow of the cannula by moving the actuator 168 to push the proximal end of the blade 165 with the rod, as shown in FIG. 7B. By reversing the direction of the actuation mechanism 168, and resultantly pulling the rod 172, the blade 165 is retracted in a reverse arcuate trajectory to its resting position in the prow of the cannula 160, as shown in FIG. 7A. It can be seen by one skilled in the art that such a trajectory will reduce the incidence of loose tissue which may be lying above the prow, from becoming pinched during retraction of the blade.

Figure 8A:
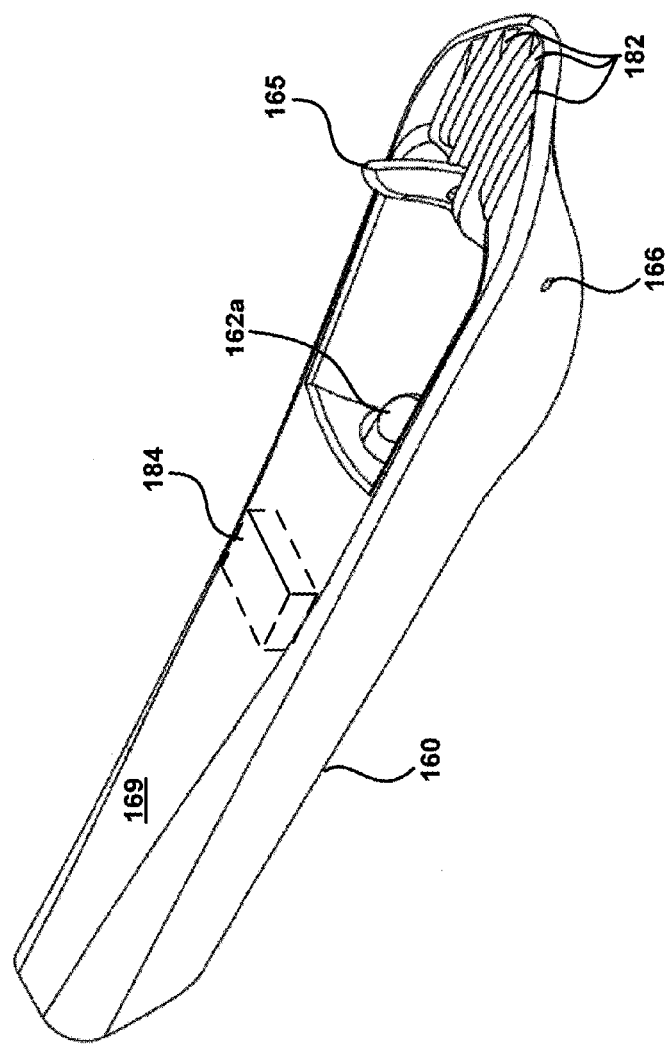
FIGS. 8A and 8B are partial perspective views of the cannula shown in FIGS. 7A and 7B.
Figure 8B:
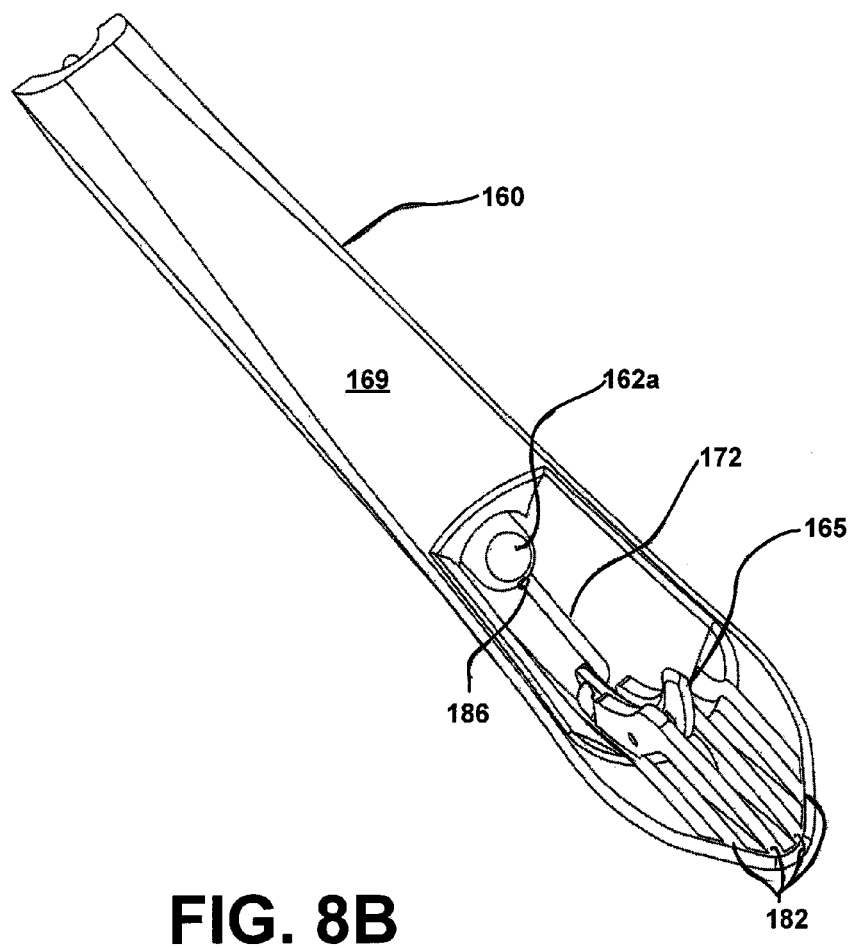
Figure 8C:
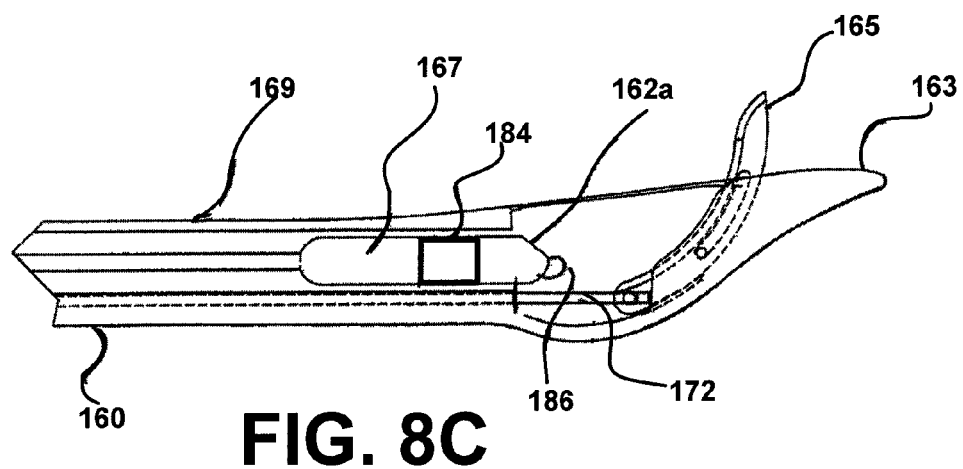
FIG. 8C is a partial, cross-sectional view taken from the side of the cannula shown in FIGS. 7A and 7B.

Referring more particularly to FIGS. 8A-8C, enclosed within the distal portion of the shaft of the cannula 160, close to the proximal end of the flared prow is, at least, part of an imaging device 162. In the present preferred embodiment, the imaging device 162 preferably includes an image sensor 184 (such as a CMOS, CCD or FOVEON) fitted with a lens 162*a* or, alternatively, an optical scope (167 of FIG. 8D). If desired, the image sensor 184 and lens 162*a* may be encapsulated within a separate transparent housing. Also, close to location of the lens 162*a* is a light source 186 such as one or more LEDs or, alternatively, the output end of a light tunnel or light transmitting fibers channeling light from a source outside of the cannula. Additionally, if desired, the flared prow of the cannula may be made of transparent material such as acrylic and may be fixed or movable.

Figure 8D:
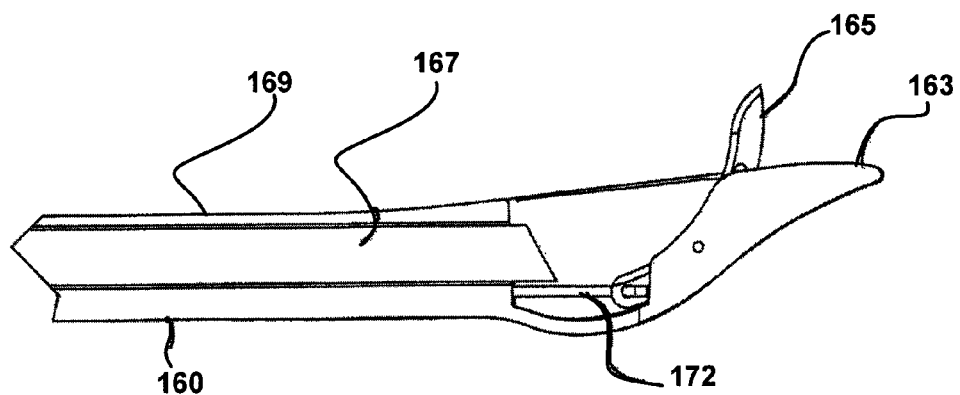
FIG. 8D is a partial, cross-sectional view taken from the side of a cannula for an endo-surgical device with the blade deployed, in accordance with one particular embodiment of the present invention
Figure 39B:
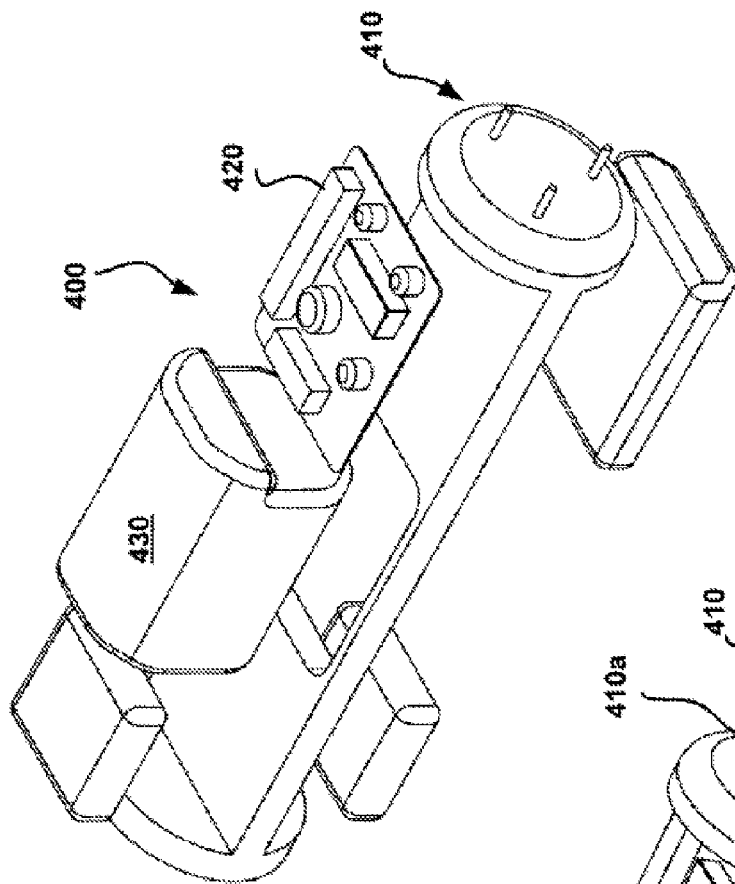
FIG. 39B is an exploded view of the electronics module of FIG. 39A.

Referring now to FIG. 9A, there is shown a perspective view of the fixed prow detachable cannula of one particular embodiment of the present invention, as described above in connection with FIGS. 7A-8C. In this embodiment, the shaft of the cannula 160 is straight. Cannula 160 can be detachably connected to a handle, such as the handle 170 of FIGS. 7A and 7B, via the connector 161. The connector 161 provides both a mechanical connection with the actuation mechanism of the device, as well as an electrical connection with the electronics in the handle 170. For example, the connector 161 includes female connections that mate with pins on the electrical module (410 of FIGS. 39A-39B), if used. Alternately, as shown in FIGS. 4B and 8D, an endoscope 167 can be passed through the connector 161. Note that, the endoscope 167 includes a connector that engages the EM module, such that images obtained by the endoscope 167 are provided to electronics on the EM 40.

FIGS. 9B and 9C show alternate embodiments of a fixed prow cannula including a deployable knife, in accordance with the present invention. More particularly, the cannula 160' includes a flared fixed prow located at the distal end of the cannula 160', the shaft of which is curvilinear. This curvilinear disposition of the shaft of the cannula 160' permits the prow to be elevated even more than in the embodiment of FIG. 9A, which is useful in pushing the fat pad out of the way during ECTR.

Similarly, the shaft of cannula 160" of FIG. 9C includes an angle bend at point 160"*a*.

This curvilinear and angled shaft permits easy access to surgical sites that may be less accessible when using a straight shaft cannula (i.e. access from the palm of the hand towards the wrist in the case of ECTR).

Figure 10A:
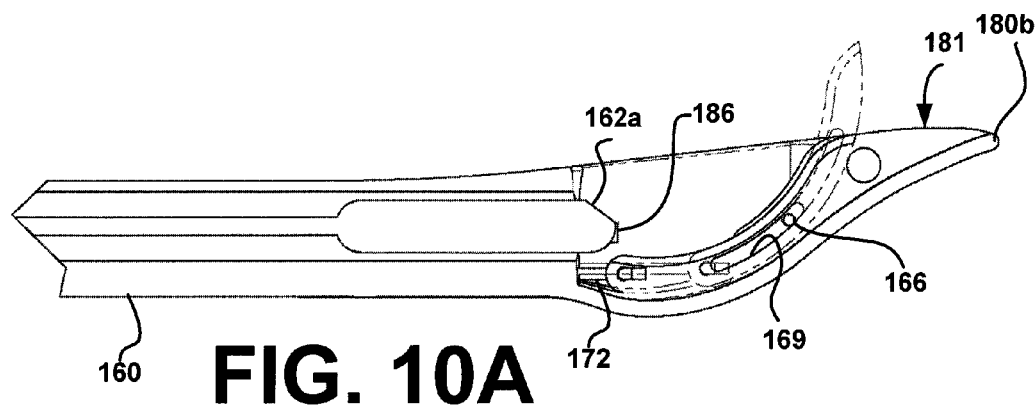
FIG. 10A is a partial, cross-sectional view, taken from the side of the cannula showing in dotted line the arcuate deployment of the blade in accordance with one particular embodiment of the present invention.
Figure 10B:
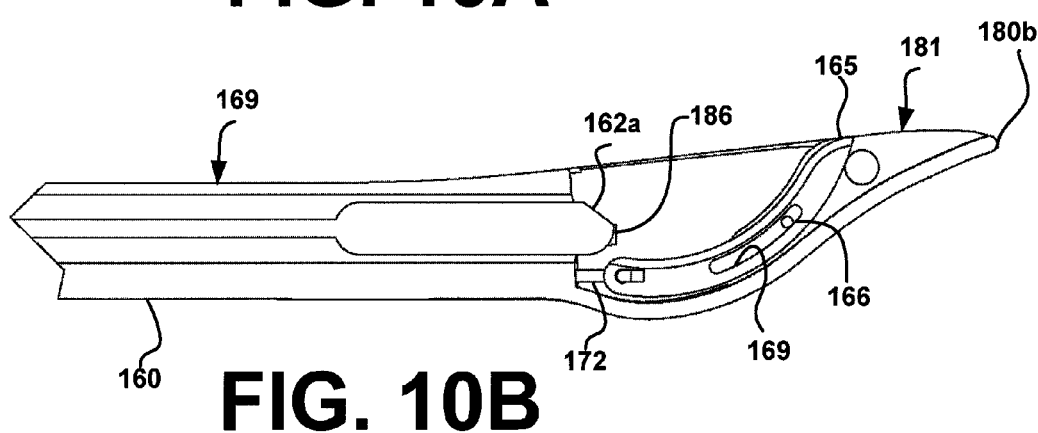
FIG. 10B is a partial, cross-sectional view, taken from the side of a cannula, in accordance with one particular embodiment of the present invention, having its blade at rest.
Figure 10C:
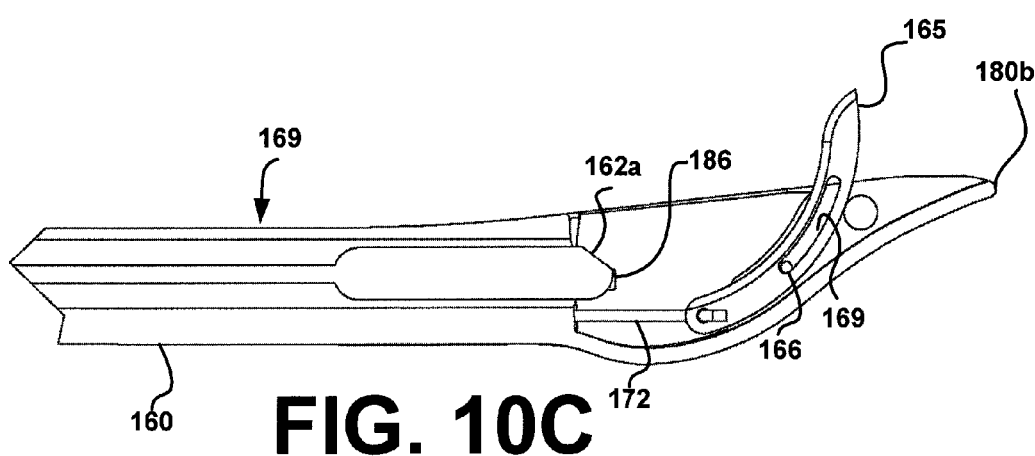
FIG. 10C is a partial, cross-sectional view, taken from the side of a cannula, in accordance with one particular embodiment of the present invention, having its blade deployed.

Referring now to FIGS. 10A-10C, there is shown in greater detail an illustration of the deployment of the blade from the prow portion of the cannula 160 of FIG. 9A. More particularly, FIG. 10B shows the cannula 160 having the blade 165 at rest. To deploy the blade 165, an actuation mechanism at the handle is deployed, which in the present embodiment, pushes the rod 172, resultantly moving the blade 165 along an arcuate path defined by the pin 166 and the blade slot 169. FIG. 10A illustrates (in dotted line) the arcuate path followed by the blade 165 during deployment. Additionally, FIG. 10C shows the fully deployed blade 165, having the pin 166 resting at the deployed end of the blade slot 169.

Referring now to FIGS. 11A, 11B, 12A, 12B, 13A and 13B, there are shown three particular embodiments of a cannula that can be used in connection with the system of the present invention to perform ECTR. More particularly, the cannula shown in FIGS. 11A and 11B is a fixed prow cannula with a movable blade 165, as discussed above in connection with FIGS. 7A-10C. In the cannula 160 of FIGS. 11A and 11B, the prow is fixedly attached to the shaft of the cannula 160 and does not move separately therefrom, while the blade 165 can be selectively actuated, as described above.

In contrast to the cannula 160 of FIGS. 11A and 11B, the cannula 190 shown in FIGS. 12A and 12B has a movable prow 192 and a fixed blade 195. In the cannula 190 of FIGS. 12A and 12B, it is the blade 195 that is fixedly attached to the shaft of the cannula 160 and does not move separately therefrom, while the prow 192 can be actuated selectively to drop, thereby exposing the TCL to the blade 195.

Both of the above-described cannulas are "single-action" cannulas, because only a single action is performed to deploy the blade (i.e., the prow is dropped or the blade is raised). The cannula 200 shown in FIGS. 13A and 13B is a "double-action" cannula, wherein the blade is exposed by both dropping the prow 202 and raising the blade 205. More particularly, in one particular embodiment, an actuation mechanism is incorporated into the cannula 200, that communicates with an actuation mechanism or lever on the handle of the device to simultaneously drop the prow 202 and deploy the blade 205, pivoting it along an arcuate path defined by a pivot pin 207 and the blade slot 206.

In operation, the purpose of the blade 165, 195, 205 stored within the prow of the cannula 160, 190, 200 is to divide the TCL. During insertion and advancement of the cannula 160, 190, 200, the flared prow and, if included, the ribs 182 shield the blade 165, 195, 205 from any contact with tissue. When the prow reaches a desired position at the distal edge of the TCL, the surgeon can deploy the blade 165, 195, 205 to initiate the division of the TCL. If the flared prow is movable, as in the embodiment of FIGS. 12A-12B, the deployment of the blade 195 is accomplished by a mechanism that drops the flared prow downwards while the blade 195 remains fixed. If the flared prow is fixed, the knife can be deployed by a mechanism that projects it upwards, following an arcuate path, until it protrudes above the upper edge of the flared prow, as described in connection with FIGS. 10A-10C and 11A-11B. Alternatively, a mechanism can both drop the movable flared prow while, simultaneously, projecting the knife upwards along an arcuate path, as described in connection with the particular embodiment of FIGS. 13A-13B.

Note that, although one particular mechanism for dropping the prow/raising the blade is described herein, this is not meant to be limiting, as other actuation mechanisms can be employed while still being within the spirit of the present invention. For example, the blade and/or prow of cannula of the present invention can be deployed using an electronic solution, such as electromagnets and/or solenoids and/or other mechanisms, electrically actuated by a button on the handle of the device. Additionally, the cannula may include one or more actionable triggers, levers or buttons to operate the movable flared prow, movable blade or both. Alternatively, some or all triggers, levers or buttons may be included in the handle.

Figure 15:
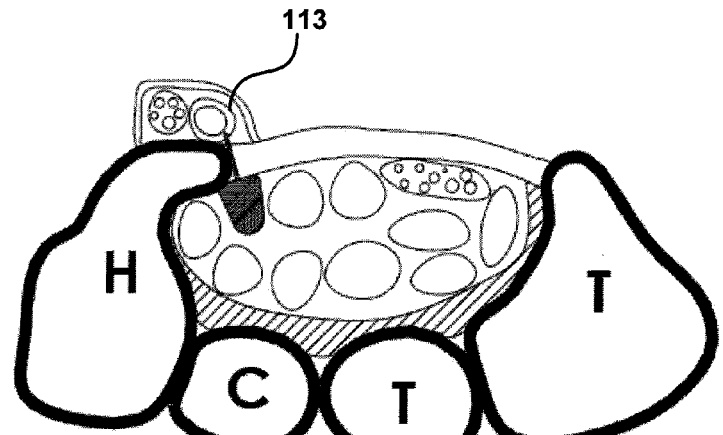
FIG. 15 is a cross-sectional view of prior art device performing a transverse carpal ligament release procedure.
Figure 16:
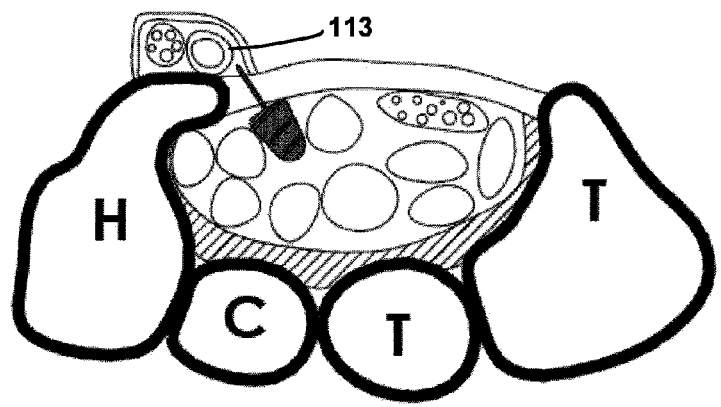
FIG. 16 is a cross-sectional view of prior art device performing a transverse carpal ligament release procedure.
Figure 14:
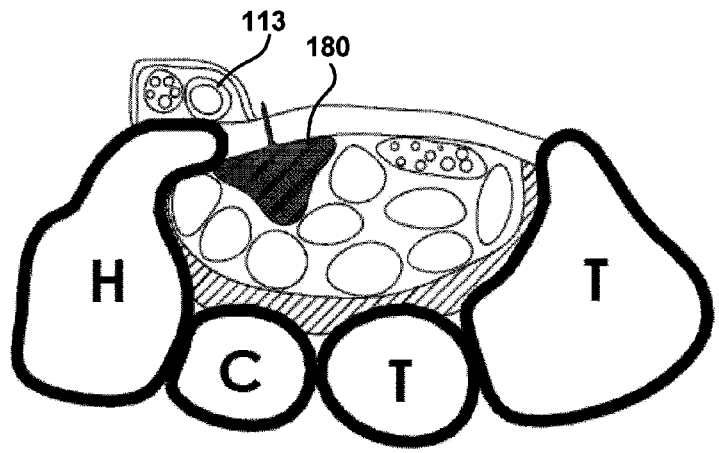
FIG. 14 is a cross-sectional view of the prow of a cannula in accordance with one particular embodiment of the present invention, performing the transverse carpal ligament release procedure.

Referring now to FIG. 14, there is shown a cross-sectional view of the prow 180 of a cannula 170, in accordance with one particular embodiment of the present invention, performing the carpal tunnel ligament release procedure. As shown in FIG. 14, and in contrast to the prior art of FIGS. 15 and 16, the flared prow 180 of the instant invention limits the displacement (FIG. 15) and rotation (FIG. 16) of the cannula, reducing the potential of the knife approaching the ulnar nerve and/or artery. Note that the flare of the prow 180 collides with the hook of the hamate (H), which limits displacement of the cannula, while the flat and wide upper surface of prow is tight against the TCL, which inhibits rotation of the cannula.

In connection with the present invention, the flared edge can be formed along the whole length of the cannula. Alternately, the flared edge can extend only through the prow, or even on a limited portion of the prow. Advantageously, this flared edge serves to create space between the TCL and the carpal bursa (or other tissues) by dissecting or separating tissue layers as it is advanced. Additionally, the flared edge can provide a greater field of view and, further, inhibit tendons and nerves from interfering with the surgical space created by the cannula.

Further, in one particular embodiment of the present invention, the ribs provide a narrow protective slit to insure isolation of tissue from the blade, reducing the potential of injury as the cannula is advanced.

If desired, the distal most portion of the cannula prow can incorporate a dissector tip embodied in a flared edge of the distal prow. In such an embodiment, the tip of the distal prow having the flared edge should be somewhat rounded and can serve to separate pre-existing tissue planes such as to create space between the ligament and the carpel bursa by dissecting as it is introduced and advanced. Accordingly, the flared edge can create its own space as the cannula is advanced.

Figure 17A:
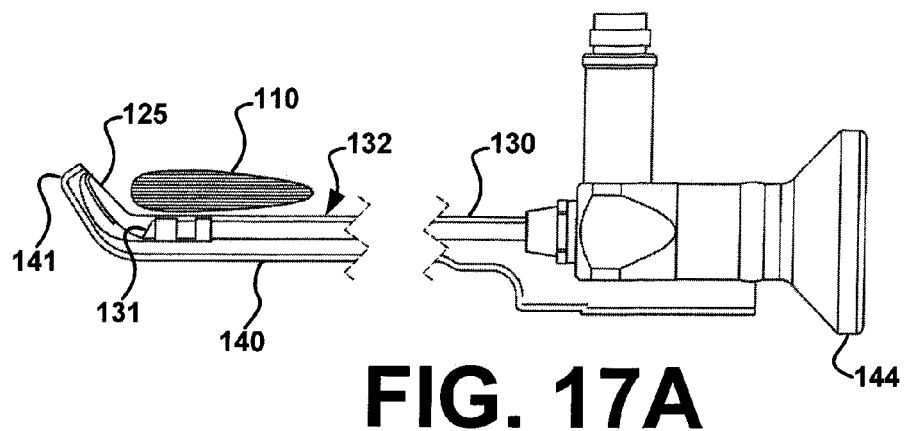
Figure 17B:
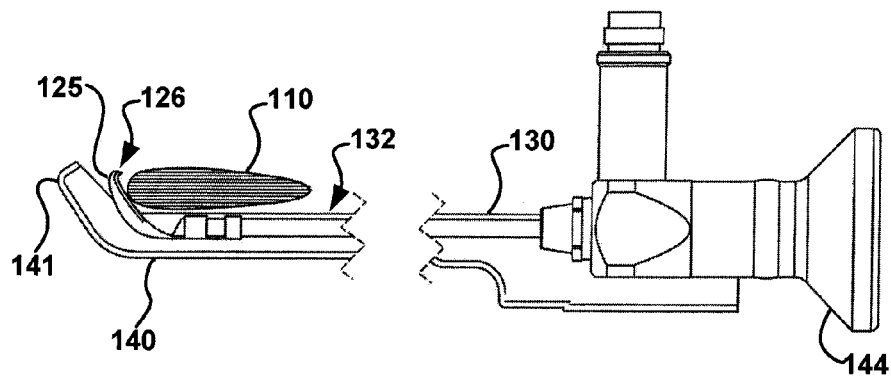
Figure 17C:
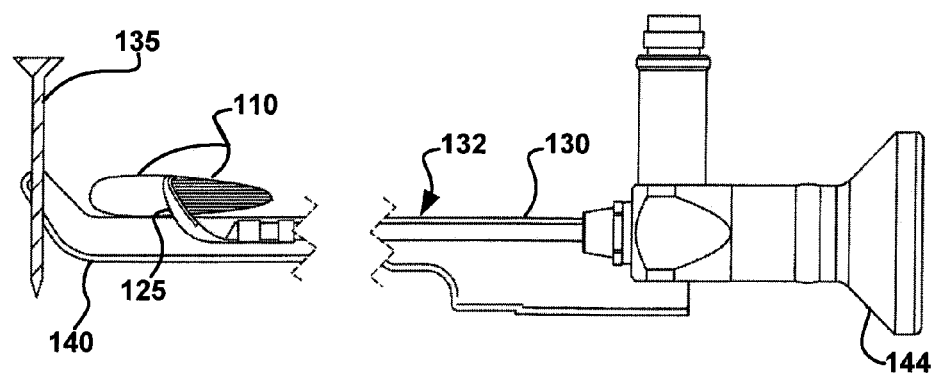

Note that, the above-described embodiments of cannulas are not meant to be limiting, as other cannula designs can be used for ECTR, while remaining within the spirit of the invention. For example, FIGS. 17A-17C illustrate another particular embodiment of a curved-tip cannula 140 having a distal prow, in accordance with the present invention. As with the previously described embodiments, the cannula 140 includes a knife 125 and an optical device 130. Note that, in the particular embodiment shown, the optical device 130 is an endoscope in optical communication with the eyepiece 144. Additionally, the curved-tip cannula 140 can expose the knife 125 and the optical device 130 along the length of the cannula 140 (i.e., the cannula 140 being a channel open at its top surface). In one embodiment, the knife 125 and optical device 130 can be exposed along the top surface of the cannula 140 from distal to proximal ends such that the knife 125 and optical device 130 can be moved together along the longitudinal axis of the cannula after the knife 125 is released. In another particular embodiment, the cannula 140 can have a substantially "U" shaped cross-section such that the knife 125 and optical device 130 can be pocketed within the cannula 140. In an embodiment where the curved-tip cannula 140 is independent from the knife/optical device assembly, the ligament 110 can be cut after separating the knife 125 from the cannula 140 by pulling the knife/optical device assembly proximally. In another embodiment, the cutting edge of the knife 125 can be deployed using a deployment mechanism before using the knife to cut the ligament 110.

Referring more particularly to FIG. 17A, in one particular embodiment of the invention, the curved-tip cannula 140 conceals the knife's edge such that the knife edge is protected during insertion of the cannula 140. In the particular embodiment shown in FIGS. 17A-17C, a unitary knife/optical device assembly 132 is used. The knife/optical device assembly 132 can incorporate an optical device 130 fixedly attached to a knife 125 having a knife edge.

Referring now to FIG. 17B, after insertion of the cannula 140, the knife/optical device assembly 132 can be retracted while the cannula 140 remains in place. In one embodiment, the knife 125 can have a tip engagement nipple 126 that can engage the distal end of the cannula 140 for securing the knife 125 within the cannula 140. In an embodiment, the knife 125 can be retracted from within the cannula 140 by depressing a release mechanism (see, for example 168 of FIG. 7A) that disengages the tip engagement nipple 126 from the distal end of the cannula 140. In this embodiment, rotation between the cannula 140 and the knife/optical device assembly 132 can be limited by matching cross sections that inhibit rotation.

Referring to FIG. 17C, the ligament 110 can then be divided as the knife/optical device 125, 130 is pulled proximally through the ligament 110. In one particular embodiment, the cannula 140 can be kept in place by a securing means. In a specific embodiment, the securing means can be a tack 135 inserted through a patient's skin into a tack opening at the tip of the cannula 140. The tack 135 can be inserted through the skin and the tack opening of the cannula 140 once the distal prow of the cannula is in place permitting a view of the distal edge of the ligament 110 through the optical device 130. In other embodiments, the securing means can be nonpercutaneous device, such as a strong magnet attracting the prow of the cannula through the patient's skin.

The optical device 130 of FIGS. 17A-17C can be cylindrical in shape and can have a distal end cut at an angle 131, as shown. In a specific embodiment, the distal end of the optical device 30 can be at an angle close to or equal to 45°. In another embodiment, the distal end of the optical device 130 can be at an angle close to or equal to 30°. In one particular embodiment, at least a portion of the curved-tip 141 of the cannula 140 can be formed of a clear material. For example, acrylic can be used to form at least a portion of the curved-tip cannula 140.

Figure 18A:
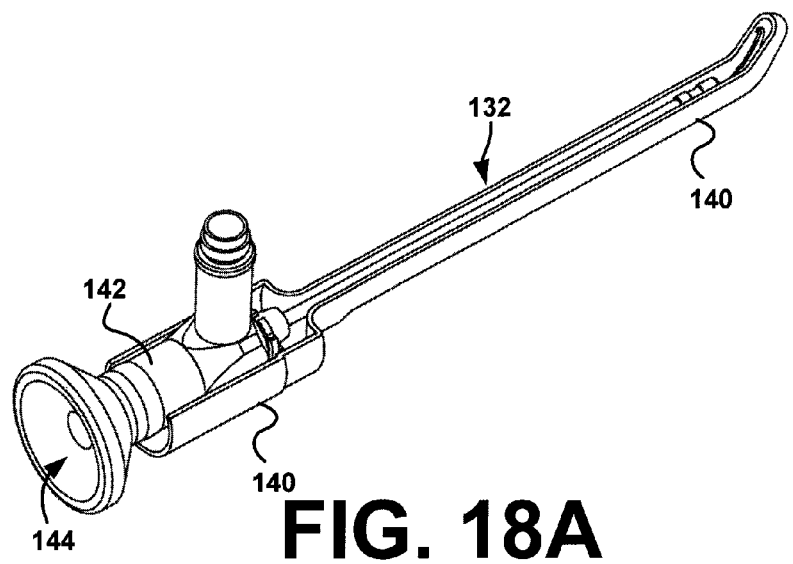
FIGS. 18A-18B show one particular embodiment of the subject cannula in connection with an ECTR system.
Figure 18B:
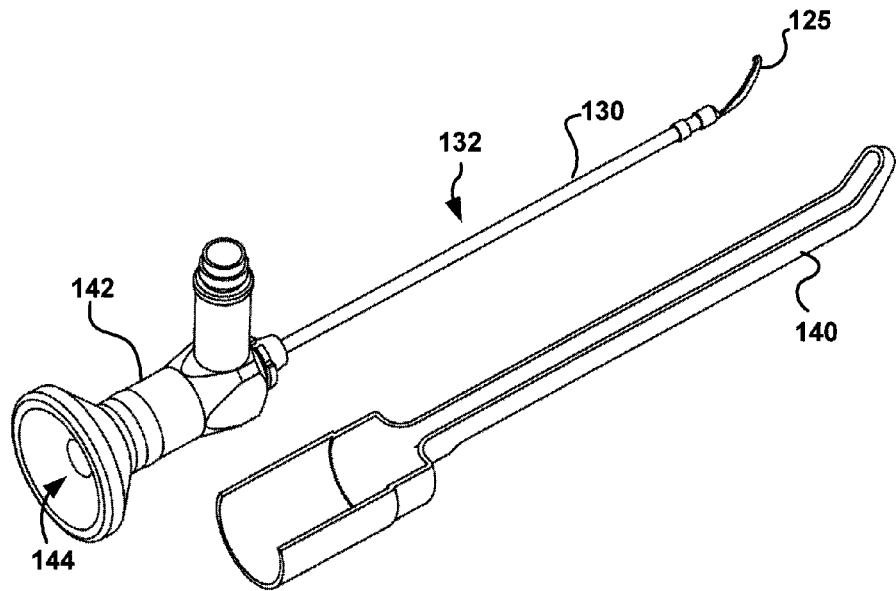

Referring to FIGS. 18A and 18B, the curved-tip cannula 140 and knife/optical device assembly 132 can incorporate an eyepiece 144 or otherwise be connected to an electronics module (see, for example, FIG. 4B). In one embodiment, the curved-tip cannula 140 can be part of a disposable blade assembly. As shown in FIG. 18B, the cannula 140 can be independent from the knife/optical device assembly 132. In use, a surgeon can insert the cannula 140 with knife/optical device assembly 132 into a patient's hand under endoscopic visualization and can then deploy the knife/optical device assembly 132 to cut the ligament. Note that the presently described endo-surgical system of FIGS. 18A-18B may or may not use an electronics module, as described elsewhere herein. This is not meant to be limiting, as the knife/optical device assembly 132 of the instant embodiment can additionally be adapted to use an optical system and electronics module, as will be described more particularly in connection with FIGS. 1-4D, among others.

Note that, the cannula of the present invention is not meant to be limited to that shown in FIGS. 18A and 18B. For example, if desired, the cannula and knife/optical device assembly can be combined into a single non-independent assembly. Additionally, if desired, the cannula need not be open along the top surface and need not expose the length of the knife and optical device. Rather, in such embodiments, the cannula will have a small opening at the tip, sufficient to permit cutting and, optionally, optical viewing when the knife is exposed.

Figure 19A:
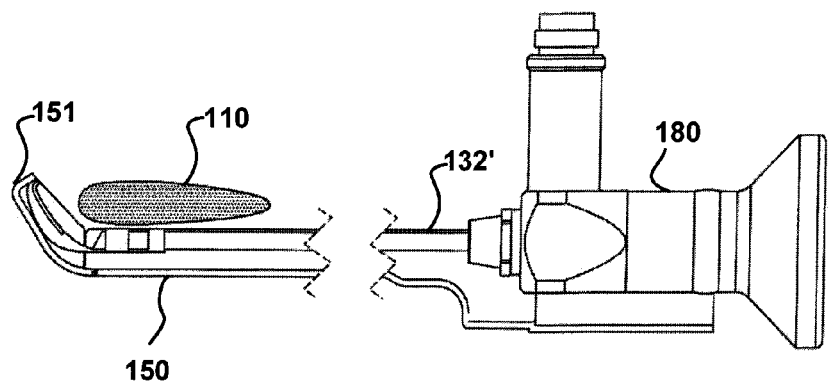
Figure 19B:
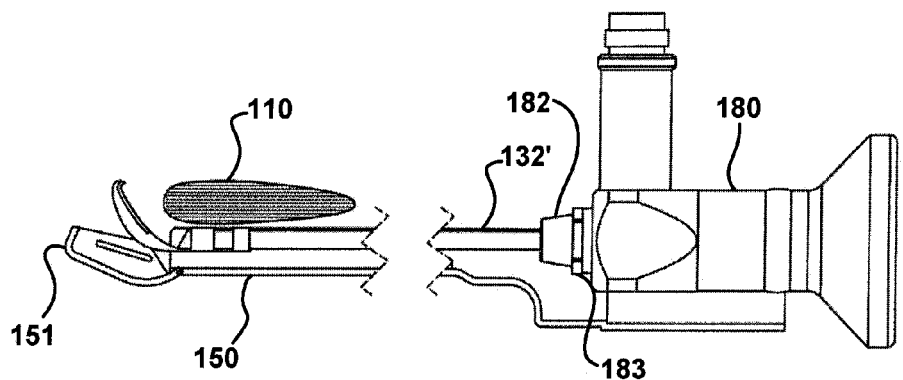
Figure 19C:
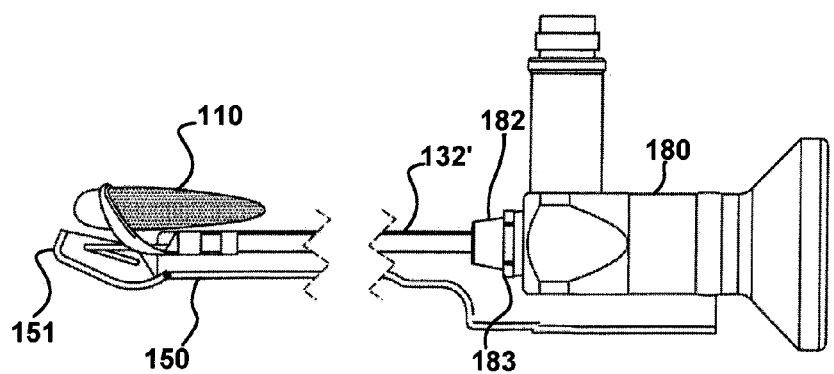

Referring now to FIGS. 19A-19C, there is shown one particular embodiment of a curved-tip cannula 150 that covers or conceals the edge of the knife 125 such that the knife edge can be protected during insertion of the cannula 150. In this embodiment, the blade edge of the knife 125 can be in a protected position during insertion of the cannula. As with the embodiment of FIGS. 17A-17C, the knife/optical device assembly 132' can incorporate an optical device 130 fixedly attached to a knife 125 having a knife edge.

Referring to FIG. 19B, after insertion of the cannula 150, the knife 125 can be deployed. In the embodiment shown, the knife 125 can be exposed by straightening the distal prow 150b of cannula 150 (i.e., dropping the tip such that the plane of the tip approaches the plane of the top surface of the cannula prow).

Figure 20A:
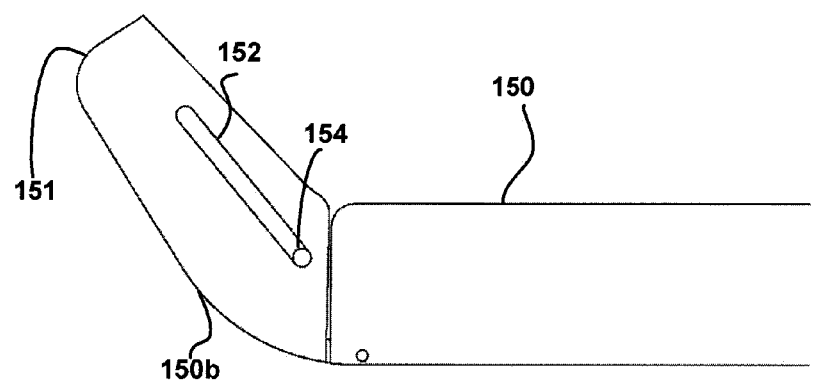
FIGS. 20A-20B show one embodiment of a cannula including a slot and pin release mechanism of the curved prow, for use with the system of FIGS. 19A-19C.
Figure 20B:
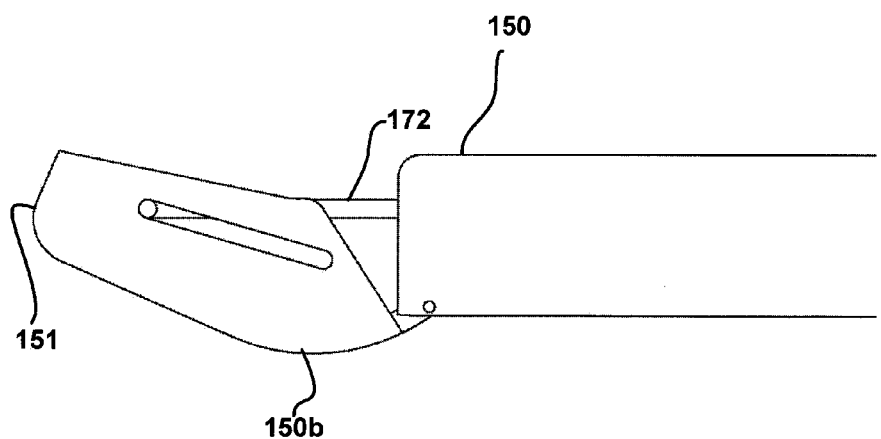

As shown more particularly in FIGS. 20A and 20B, live hinges, pins and/or traditional hinges can be used to facilitate activation of the distal prow 150b, and thus opening and closing of the distal prow 150b. Other embodiments are additionally possible. For example, one particular embodiment wherein the blade edge of the knife 125 begins in a retracted position, the blade edge can be deployed into an extended position to cut the ligament 110 using a deployment mechanism. In the embodiment illustrated in FIGS. 20A and 20B, a release mechanism 160 can be used to straighten the distal prow 150b of the cannula. The release mechanism 160 can incorporate a transverse pin 154 and slot 152, as shown in FIGS. 20A and 20B. In one particular preferred embodiment, the slot 152 can be placed in the distal prow 150b at the tip 151 of the cannula 150.

In another embodiment of the instant invention, the knife 125 can be retracted proximally or distally a short distance, preferably less than 10 mm and, more preferably, less than 2-3 mm. By retracting the knife 125, a transverse pin can be moved on a slot formed in the distal prow 150b. If desired, an engagement mechanism (not shown) can be incorporated on the cannula to engage the release mechanism. The engagement mechanism can be depressed to expose the knife 125 (see, for example, the engagement mechanism 168 of FIG. 7B). For example, an engagement/actuation mechanism can be provided, depression of which moves the transverse pin 154 along the slot 152. Referring to FIG. 19C, the ligament 110 can then be divided as the cannula 150 and knife/optical device assembly 132' are pulled proximally as a unit through the ligament 110. It is possible that more than one pass of the blade 125 will be required to sever the ligament.

Referring more particularly to FIGS. 20A-20B, the slot 152 can be formed at different angles and can also be shaped as an arc segment concentric to the center of rotation of the curved tip. FIGS. 20A and 20B illustrate only one possible embodiment for the slot and pin combination. As shown, the distal prow 150b can be straightened by pushing the release mechanism. As the release mechanism is pushed, the pin 154 can be moved up the slot 152 in the cannula causing the distal prow 150b of the cannula to straighten. As the distal prow straightens out, it exposes the knife 125 (FIG. 19B) to allow cutting of the ligament 110. From the foregoing, it is understood that other slot orientations are possible while still keeping with the spirit of the present invention As with the previous embodiment, the distal prow 150b of the cannula 150 can be formed of clear material. In a specific embodiment, the distal prow 150b of the cannula 150 can be formed of acrylic.

Cannula with Spreader Device

In the preferred embodiment of the invention, the endo-surgical system can be used with various surgical, diagnostic or therapeutic tools, and can incorporate one or more actuators. Examples of tools that can be utilized can include scissors, a blade, grasping claw, spreader, and pushing tool. Accordingly the subject cannula can be adapted to include and operate the various tools. Thus, actuators for operating the various tools can be integrated with the cannula and/or with the handle. Additionally, if an actuator is integrated on the cannula, the handle can have a cut-out near the attachment site to provide trigger/actuator space for different cannula attachments.

More particularly, referring now to FIGS. 21A-24, there is shown a spreader device 210 for creating or maintaining a soft tissue surgical cavity in endo-surgical procedures. For example, in contrast to the carpal tunnel cannulas shown in FIGS. 7-13, the spreader device shown in FIGS. 21A-24 is specially adapted for use in surgeries where it is necessary to create a relatively large temporary tissue cavity in order to access the specific anatomical structures that are to be surgically manipulated. These procedures include, but are not limited to, tendon sheath release surgeries such as trigger finger release, Dequervain's release and posterior tibial tendon release. The spreader device of FIGS. 21A-24 can also be used for connective tissue transection surgeries such as tennis elbow release, plantar fasciotomy and fasciotomies in general. Furthermore, the spreader device of FIGS. 21A-24 is particularly adapted to perform nerve release operations such as cubital tunnel release, pronator tunnel release, Morton's neuroma release and tarsal tunnel release. Common to all these surgical procedures, the anatomical structure to be operated upon is covered by a substantial amount of subcutaneous tissue that must be displaced.

Figure 21A:
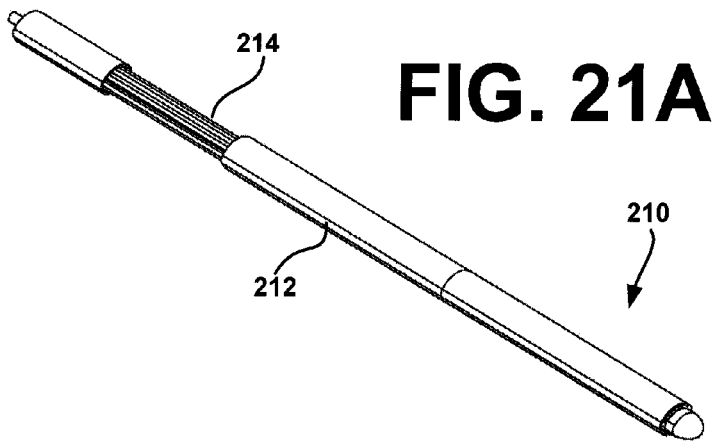
FIGS. 21A-21B show another particular embodiment of a cannula including a tool for use in accordance with the present invention.
Figure 21B:
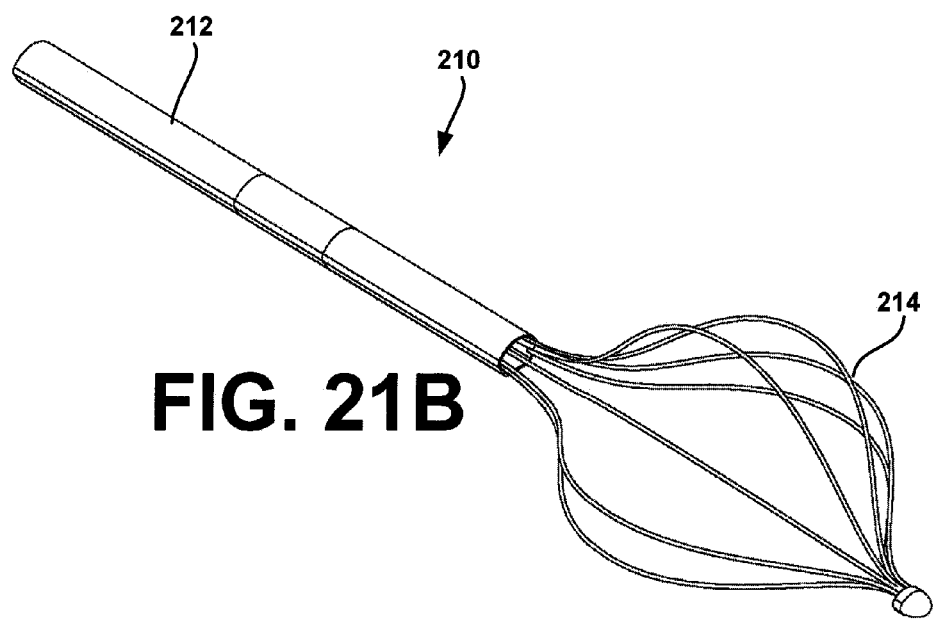

As shown in FIGS. 21A-21B, the spreader device includes a spreader cannula 212 component that is introduced into the body and an expansible mesh or scaffold component 214 that is deployed through this cannula. This scaffold, after deployment, tents or supports adjacent tissue away from the anatomical structure of interest in order to allow its endoscopic visualization and surgical manipulation.

In one particular embodiment of the present invention, as shown in FIGS. 22A and 22B, the spreader device 210 is a separate unit and can matingly engage with the endo-surgical imaging cannula portion of a device similar to the one shown in FIGS. 1 to 4D. The spreader cannula 212 would be introduced into the body first. This would be followed by insertion and deployment of the spreader mesh and expansion of the surgical cavity. Afterwards, the cannula 216 on the endo-surgical device would be introduced into the surgical cavity through the already introduced spreader cannula, as shown, more particularly, in FIGS. 22A and 22B. In other words, a first cannula that allows introduction of a spreader device is inserted into the surgical area. The surgical cavity is maintained by inserting the spreader device. Finally, a second cannula 216 containing an imaging device and a surgical, diagnostic or therapeutic tool connected to a handle and an electronics module EM, as described above in connection with FIGS. 1-4D, is inserted through the first cannula 212 and into the surgical cavity in order to perform the surgical procedure under visualization in a display desirably located within the sterile surgical field.

Figure 23A:
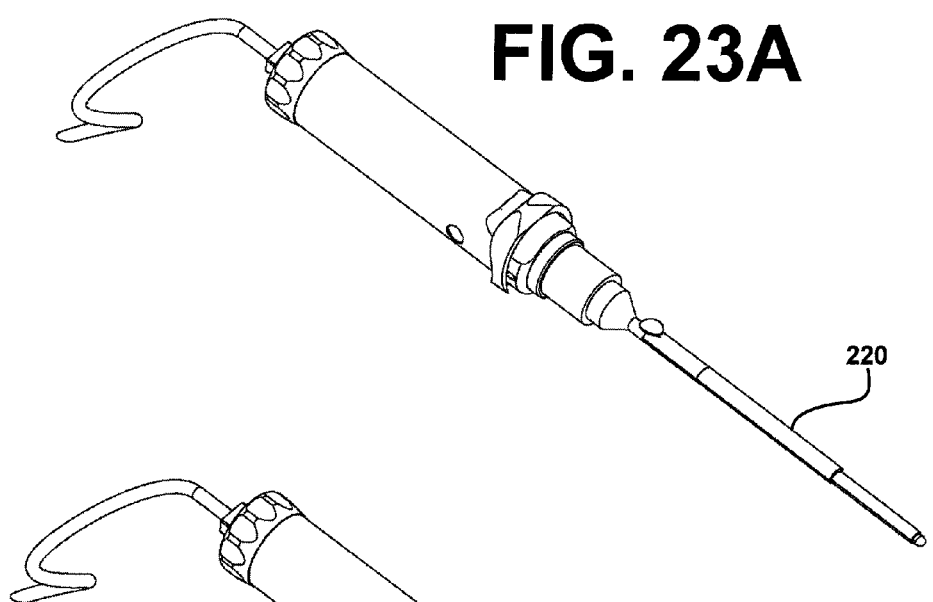
FIGS. 23A-23B show another particular embodiment of an endo-surgical device including a tool for use in accordance with the present invention.
Figure 23B:
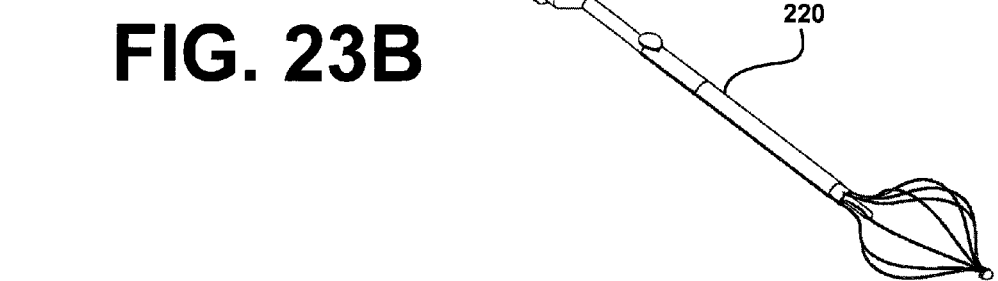

In another embodiment shown in FIGS. 23A and 23B, a spreader device 220 can be incorporated into an endo-surgical instrument, such as the device shown in FIGS. 1 to 4D. Through an actuator mechanism, the spreader can be expanded inside the body to produce the surgical cavity. This embodiment would allow the endoscopic instrument to simultaneously create the working space, illuminate the area, deliver a tool (as shown, for example, in FIGS. 23B and 24) and provide imaging for surgical procedures. In other words, a cannula containing an imaging device, a medical tool and fitted with the spreader device of FIG. 21 (i.e., which is deployed by an actuator), can be connected to a handle and an electronics module as described above in connection with FIGS. 1-4D, which communicates to a display within the sterile surgical field where the surgeon can visualize the procedure in real-time.

Figure 4A:
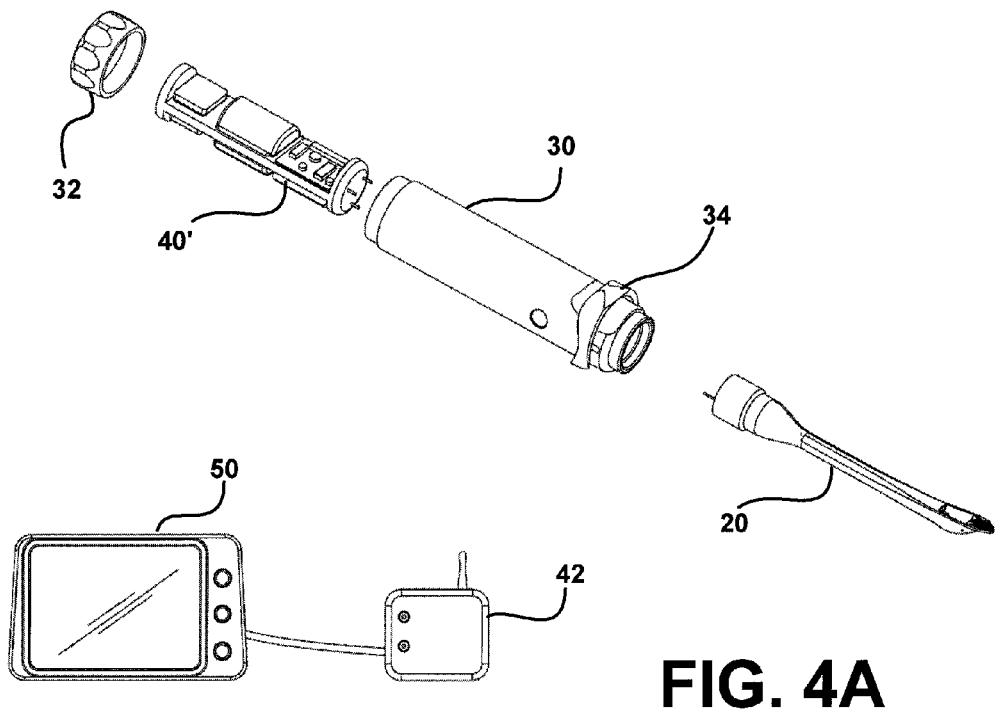
FIG. 4A is a perspective view of another embodiment of an endo-surgical system in accordance with the present invention, including an exploded view of an endo-surgical device useful in that system.
Figure 4B:
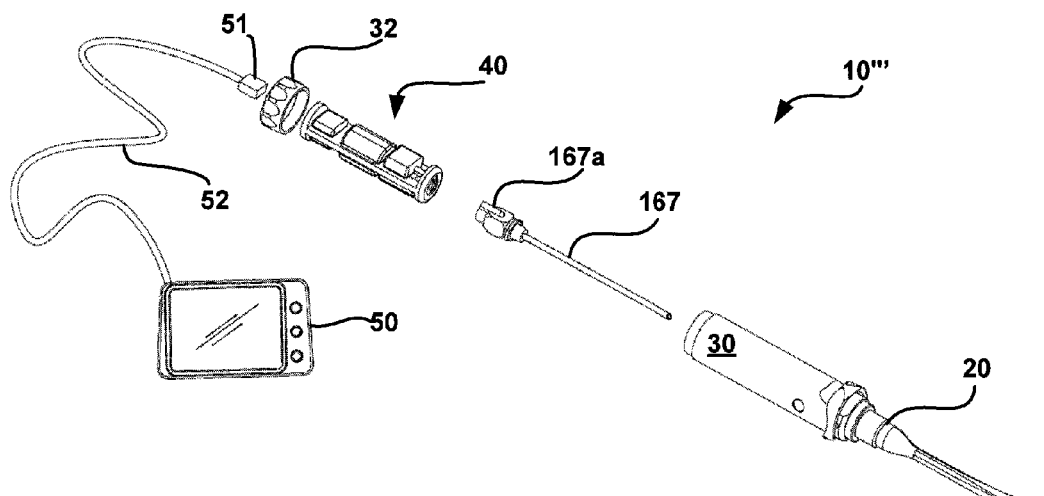
FIG. 4B is a perspective view of an endo-surgical system in accordance with another particular embodiment of the instant invention.
Figure 4C:
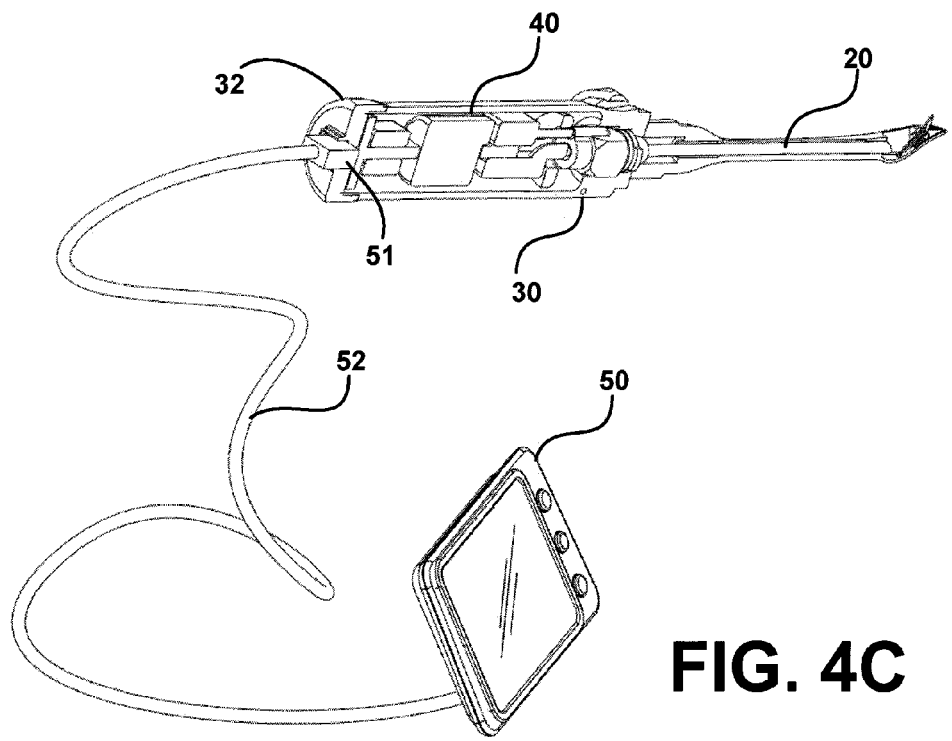
FIG. 4C is a perspective cross-sectional view of an endo-surgical system in accordance with another particular embodiment of the instant invention.
Figure 4D:
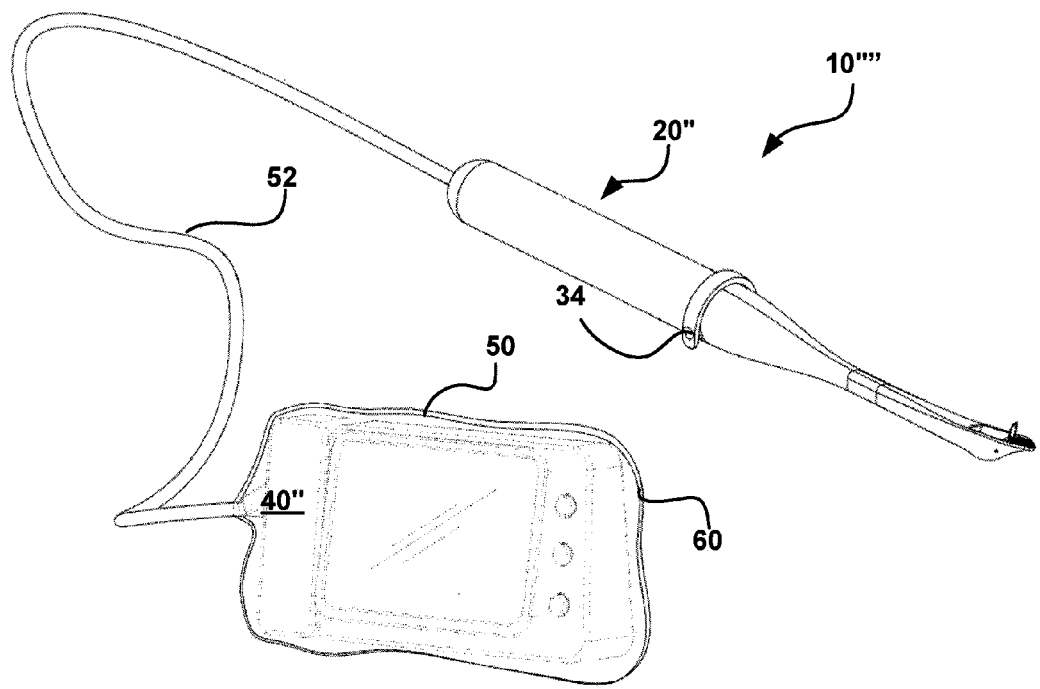
FIG. 4D is a perspective view of an endo-surgical system in accordance with another particular embodiment of the instant invention.

As an alternative to making the device in two parts (as shown in FIGS. 23A and 23B), the spreader device, imaging device, surgical tool, the handle, and the cable could be incorporated into a single sterile disposable unit that would connect to a separate electronics module and display unit enclosed in a sterile disposable enclosure and placed within the sterile surgical field as shown in FIG. 4D.

Figure 23C:
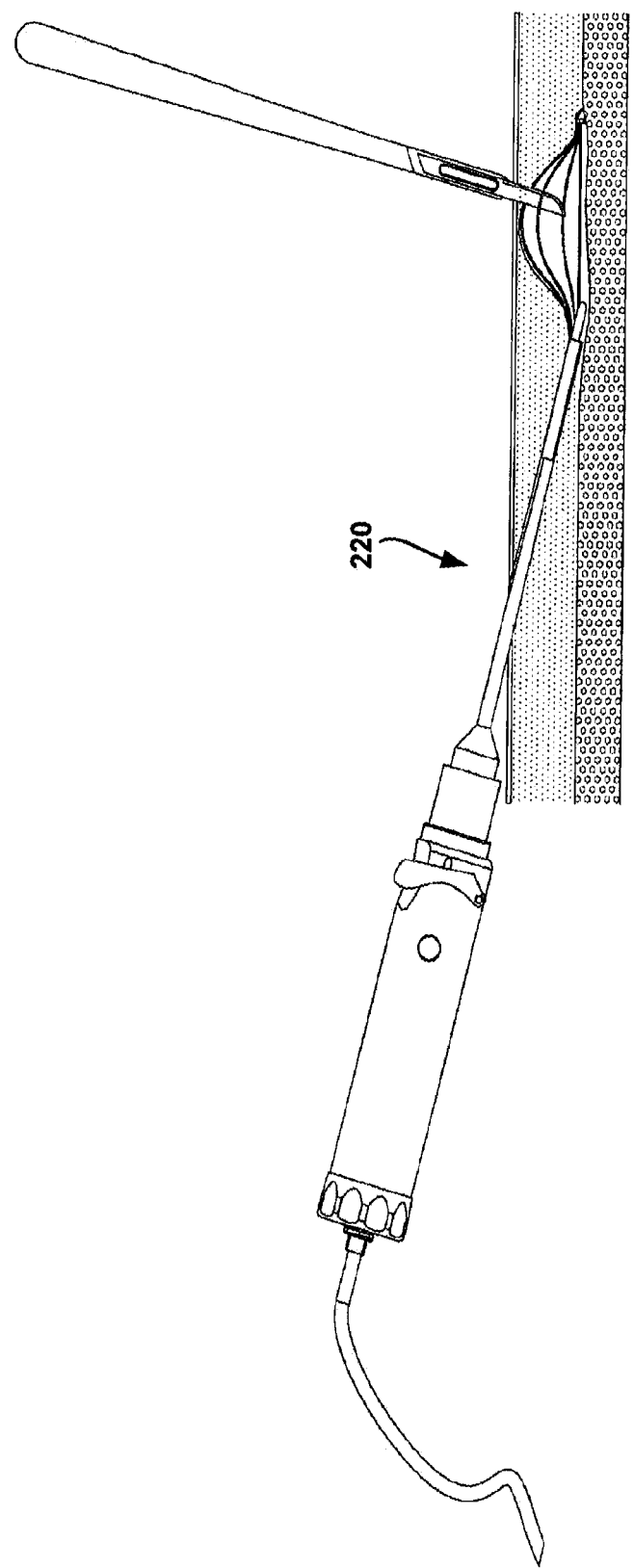
FIG. 23C shows one particular use of the tool of FIGS. 23A and 23B.
Figure 25:
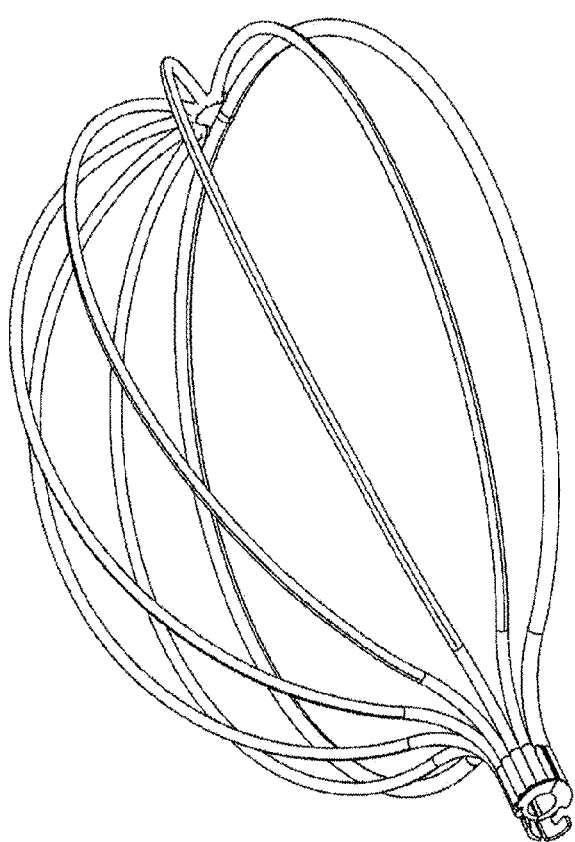
Figure 26:
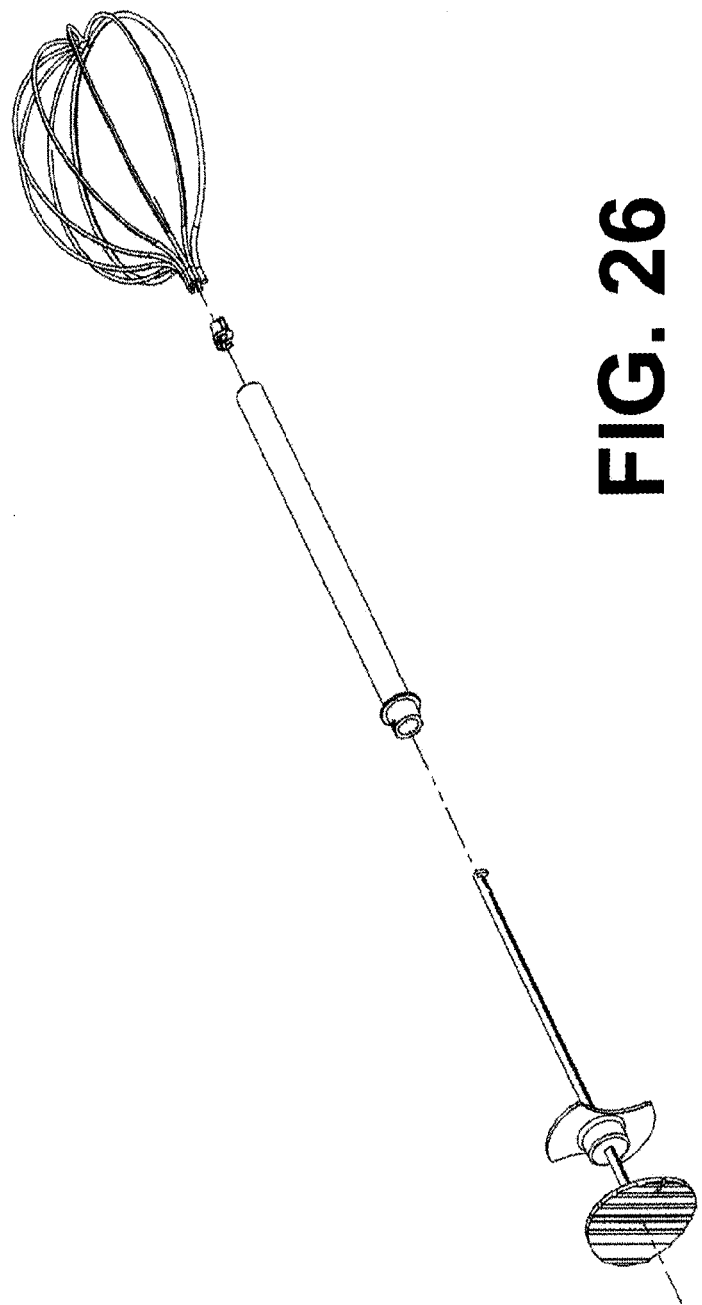
Figure 27:
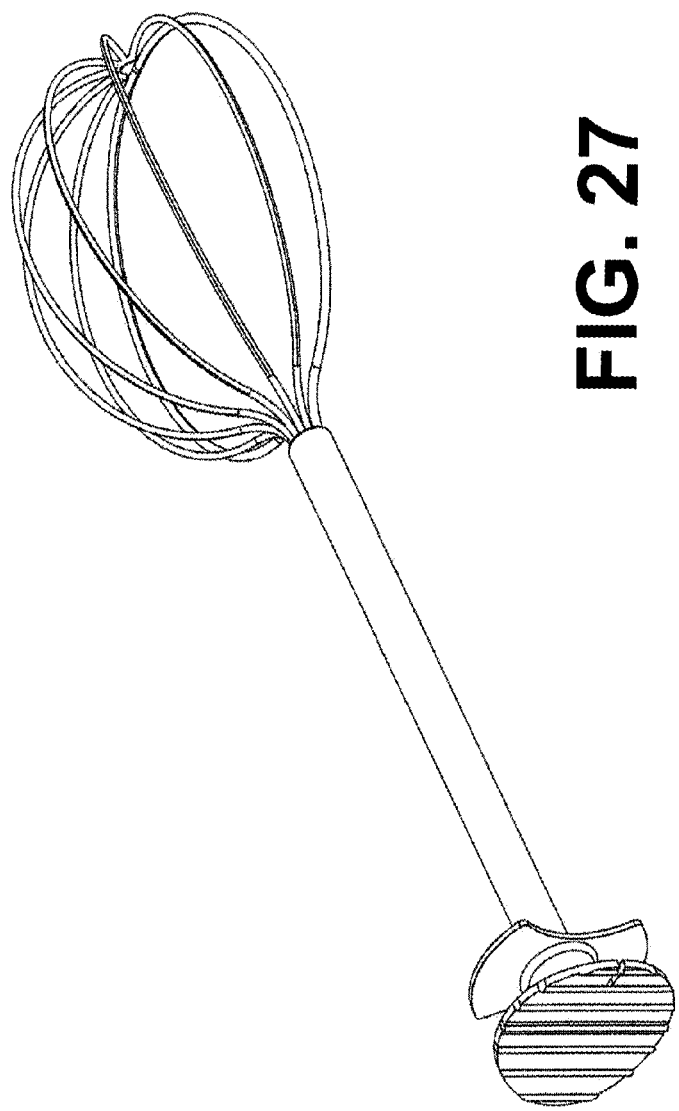
Figure 28:
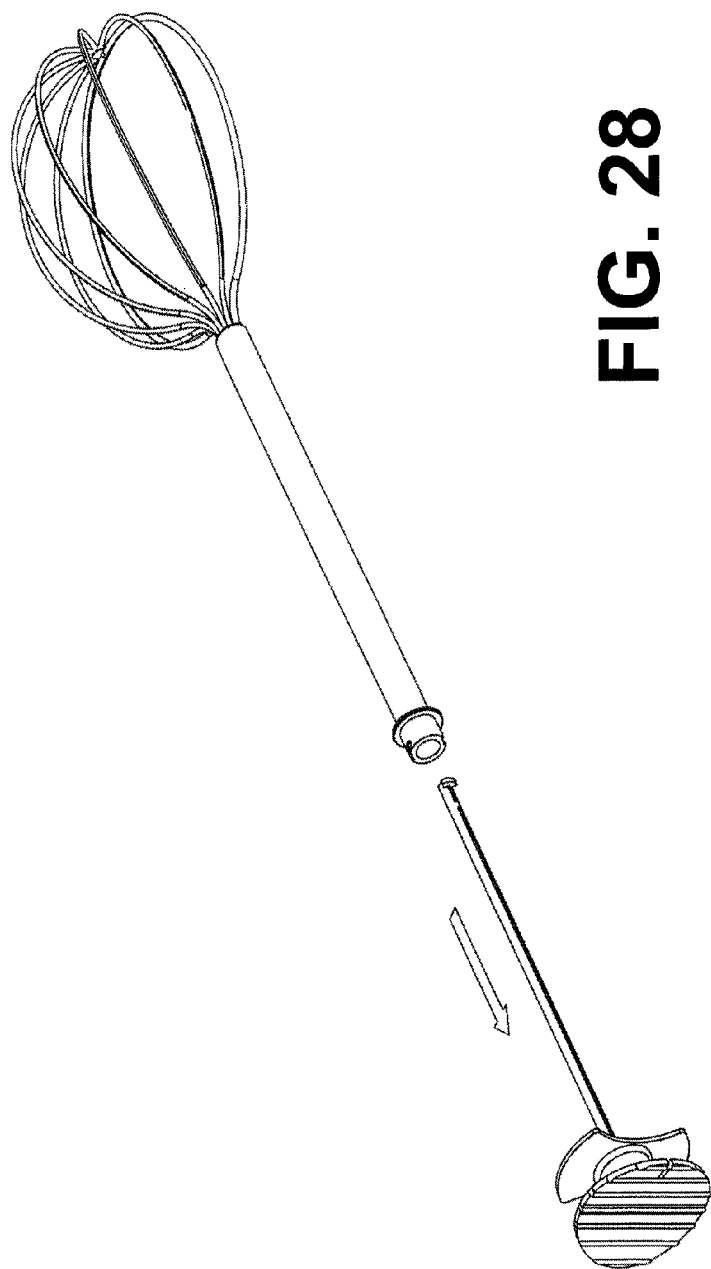
Figure 30:
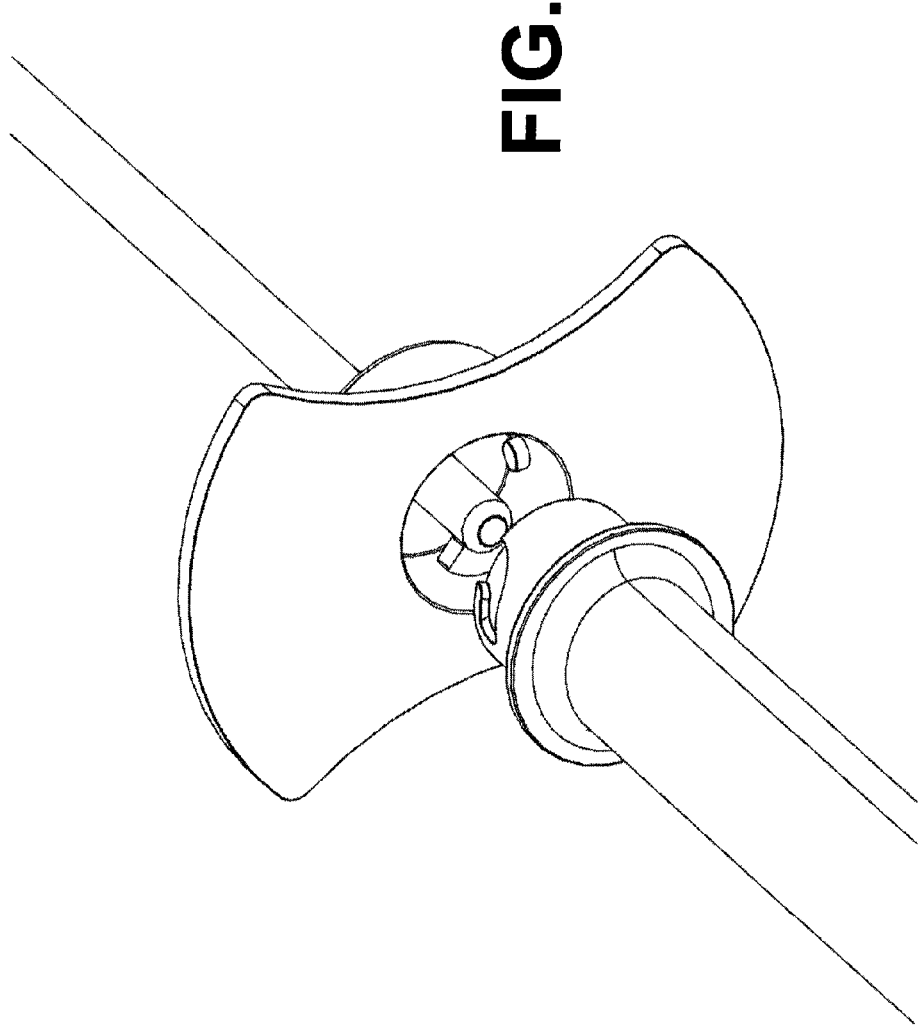
Figure 31:
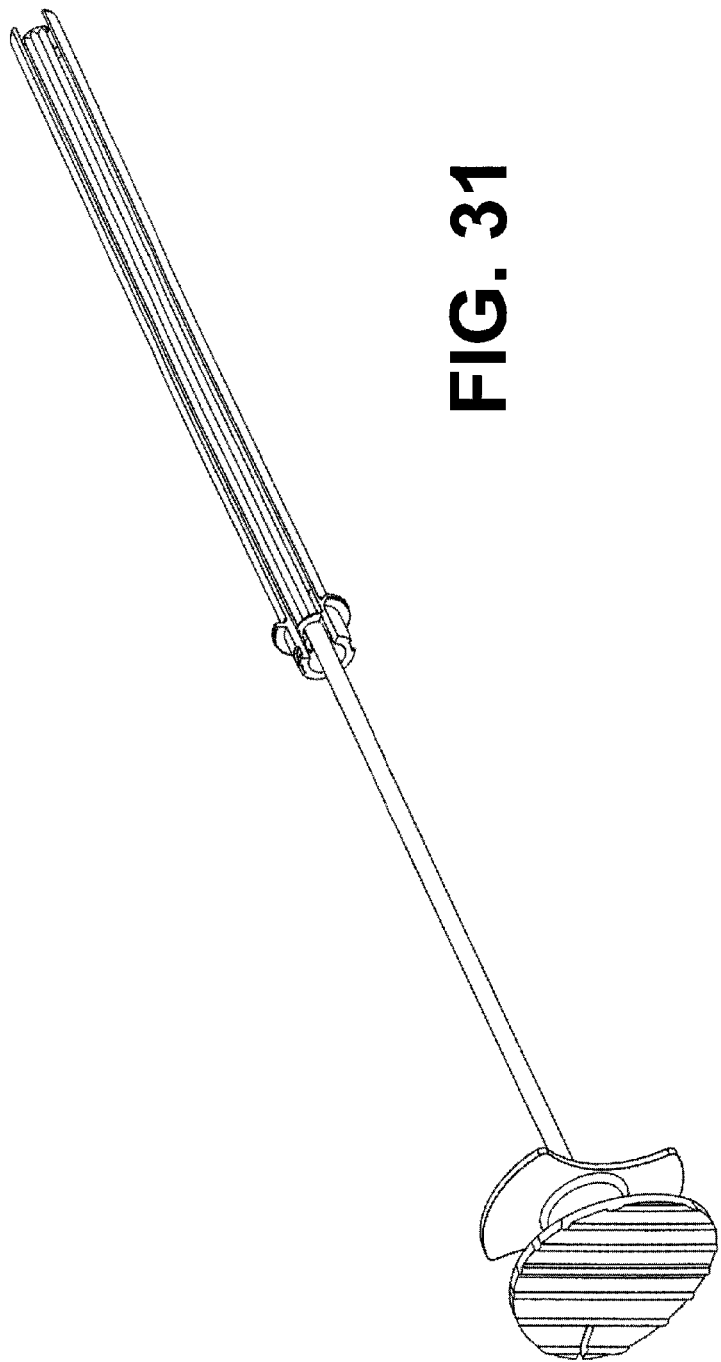
Figure 32:
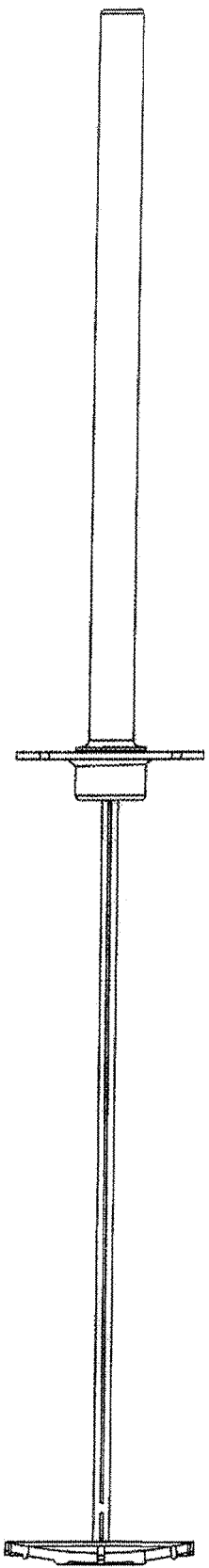
Figure 33:
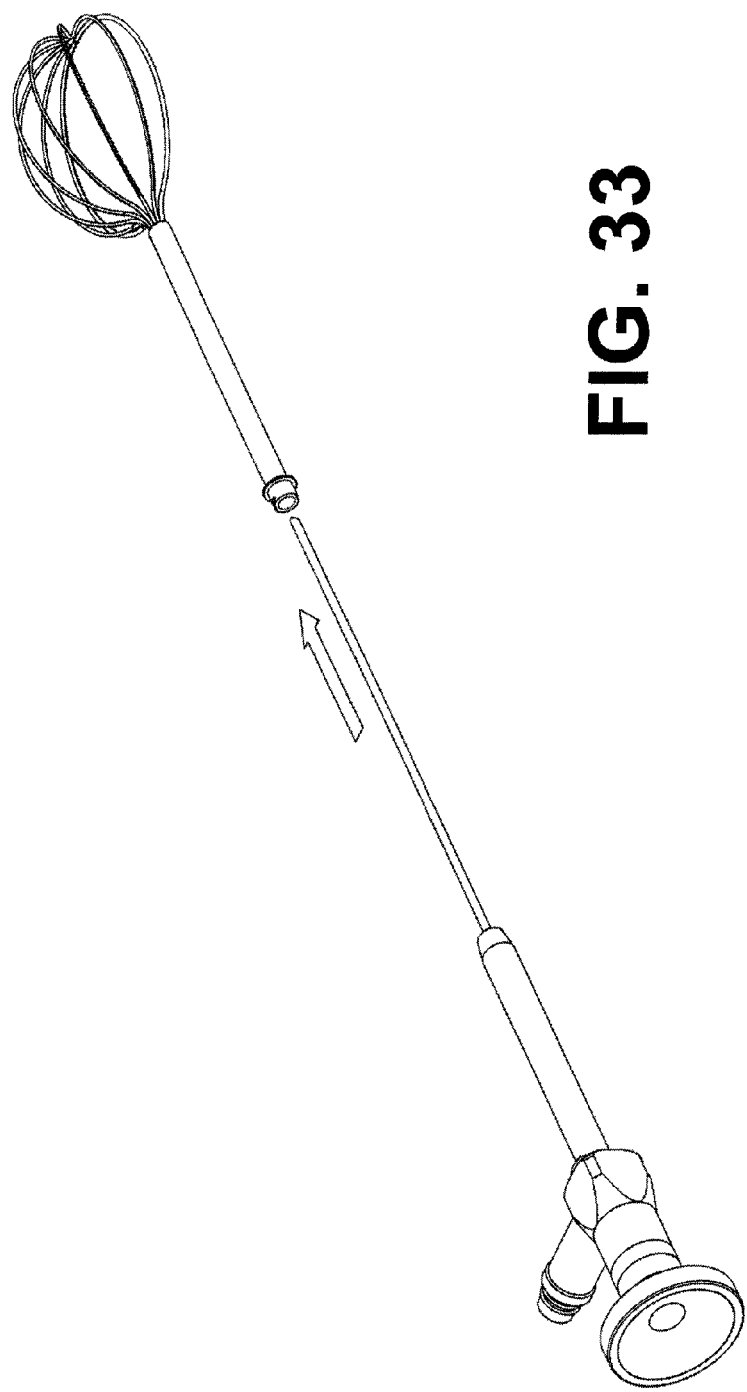
Figure 34:
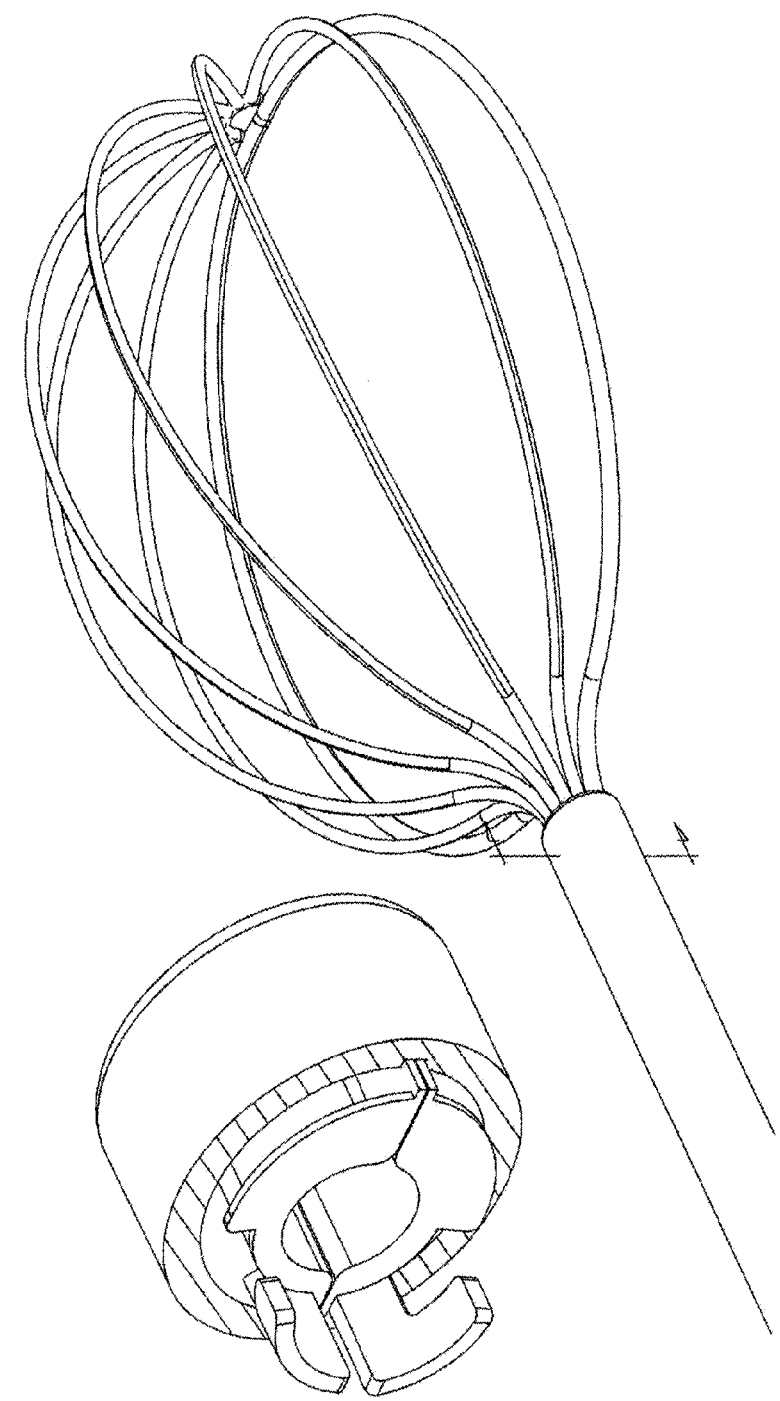

In another embodiment of the present invention, the endo-surgical instrument could include the imaging device for visualization, together with the spreader device shown in FIG. 21, but may omit any type of surgical device. As shown in FIG. 23C, using an endo-surgical device in accordance with this embodiment, a separate surgical tool 222 can be introduced into the surgical cavity through another small incision and between the mesh elements. This would give the surgeon the ability to manipulate the surgical tool with one hand while stabilizing the imaging instrument with the other hand and therefore avoiding distortion.

In another embodiment shown in FIG. 24, the endo-surgical device 224 includes the imaging device and a surgical tool, but not a spreader device. In this embodiment, the spreader device 226 alone is first inserted through its own cannula to create and/or maintain the desired surgical cavity. After the spreader has been positioned and actuated, an endo-surgical device in accordance with one embodiment of the invention is inserted separately through another small incision and between the mesh elements into the surgical cavity to perform the procedure. The device of FIG. 24, and the method described herewith, takes the function of maintaining the surgical cavity away from the endo-surgical instrument, consequently removing resistance to motion and facilitating delicate surgical maneuvers. If desired, as additionally shown in FIG. 24, a separate knife 228 or other instrument can be introduced into the surgical cavity through a third small incision. In this manner the function of maintaining a surgical cavity, the imaging function and the surgical tool function can be separated. If a separate surgical tool, such as a knife or other instrument, is used, the surgical instrument at the tip of the endo-surgical device of FIG. 24 may be omitted or, alternately, not used, or only minimally used, in a particular procedure. This may be a good alternative for difficult procedures where precise control and stability is needed.

The cannula and spreader device of FIGS. 21-24, upon insertion and deployment, may be used to create the surgical cavity. Alternatively, the actual space to be maintained by the spreader may be created prior to insertion of the cannula and spreader by the surgeon using a different instrument, such as a hemostat, which is a commonly available generic surgical instrument.

FIGS. 25-34 show particular embodiments of an inventive spreader device and assembly that can be used as described herein.

Referring now to FIGS. 35A-36C, there is shown another surgical tool that can be implemented in connection with the instant invention. Referring to FIG. 35A, an embodiment of the present invention can include interchangeable cannulas with different tips for different purposes. A reusable or disposable handle 300 can be used with an interchangeable cannula 302. An endoscope 301 or, alternately, an electronic imaging device, can be included in the handle 300. FIG. 35B illustrates a retracted position of a tool, and FIG. 35C illustrates an exposed position of a tool. In an embodiment, the cannula can include two actuators. The first actuator can be an engagement mechanism 304. The engagement mechanism 304 can be used to retract an angled distal end 303 of the cannula to expose a tool. The second actuator can be a trigger 305 that can be used to control movement of a tool. In one embodiment, the tool can be a scissor-type. The scissor-type tool 308 can include a static blade 306 and a rotating blade 307.

Figure 36A:
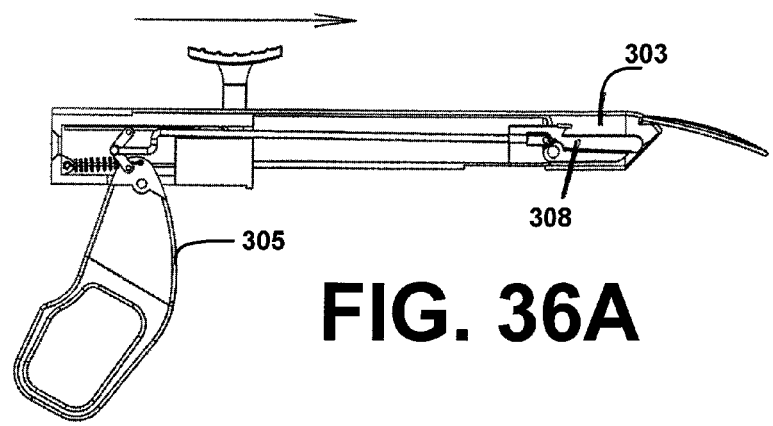
FIGS. 36A-36C show another particular embodiment of an endo-surgical device including a tool for use in accordance with the present invention.
Figure 36B:
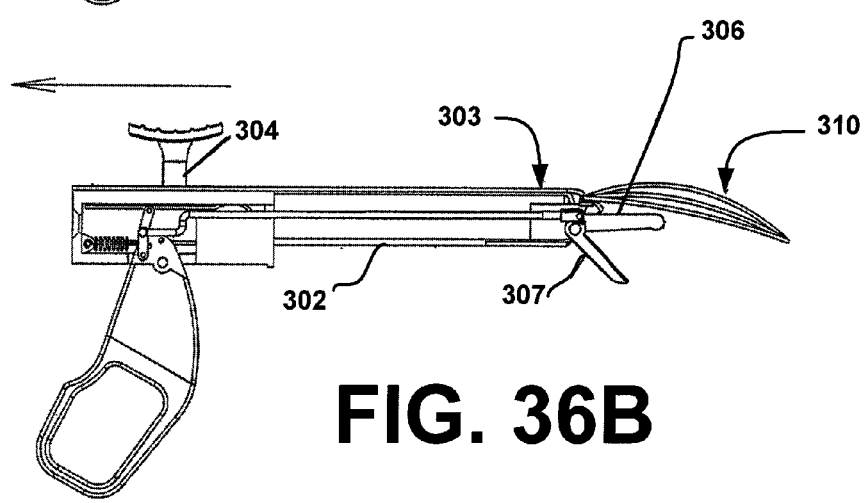
Figure 36C:
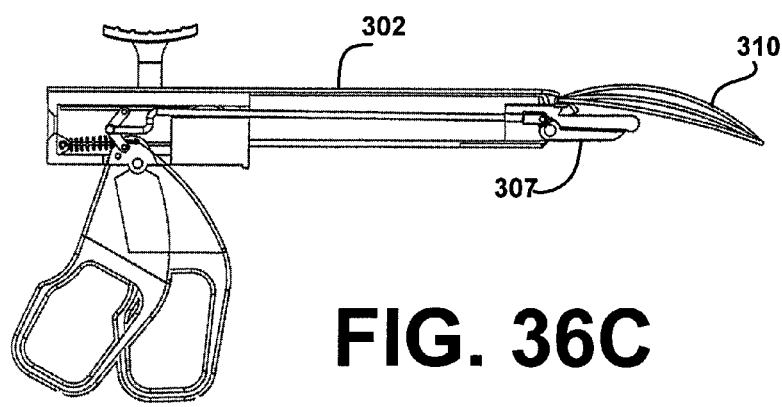
Figure 37:
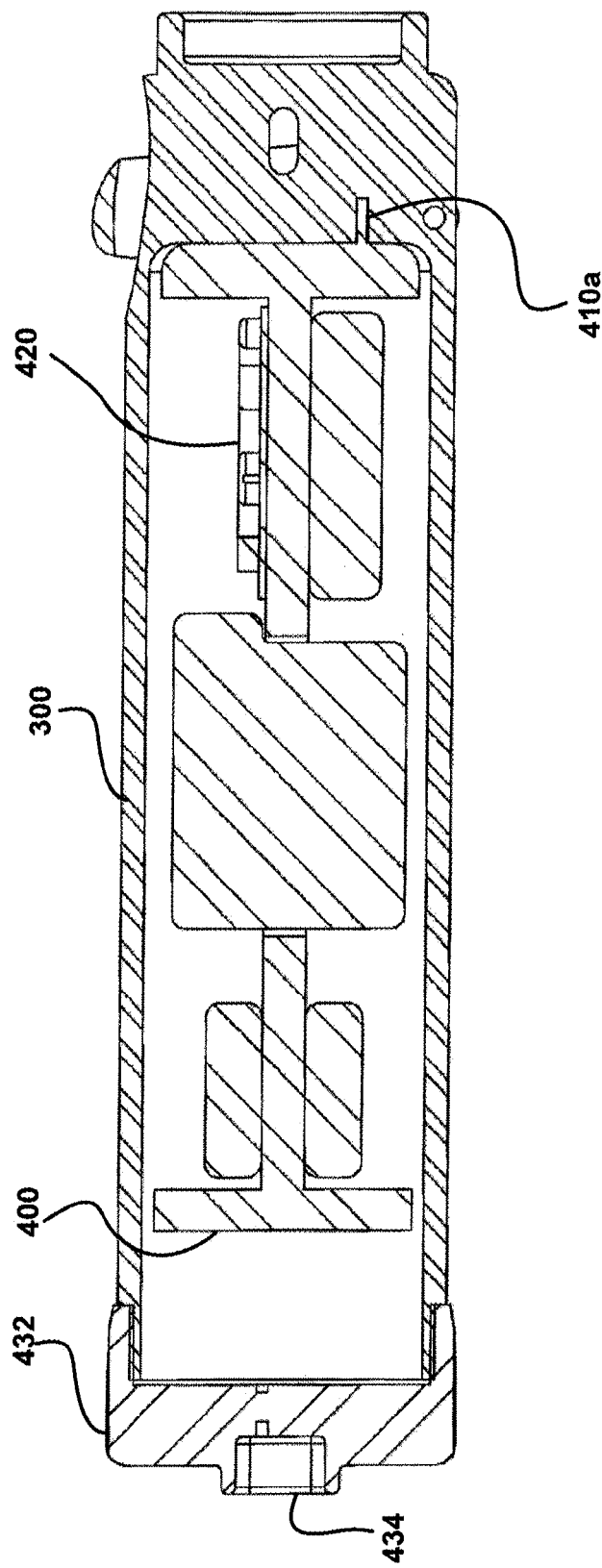
FIG. 37 is a cross-sectional view of a handle including an electronics module, in accordance with one particular embodiment of the present invention.
Figure 38:
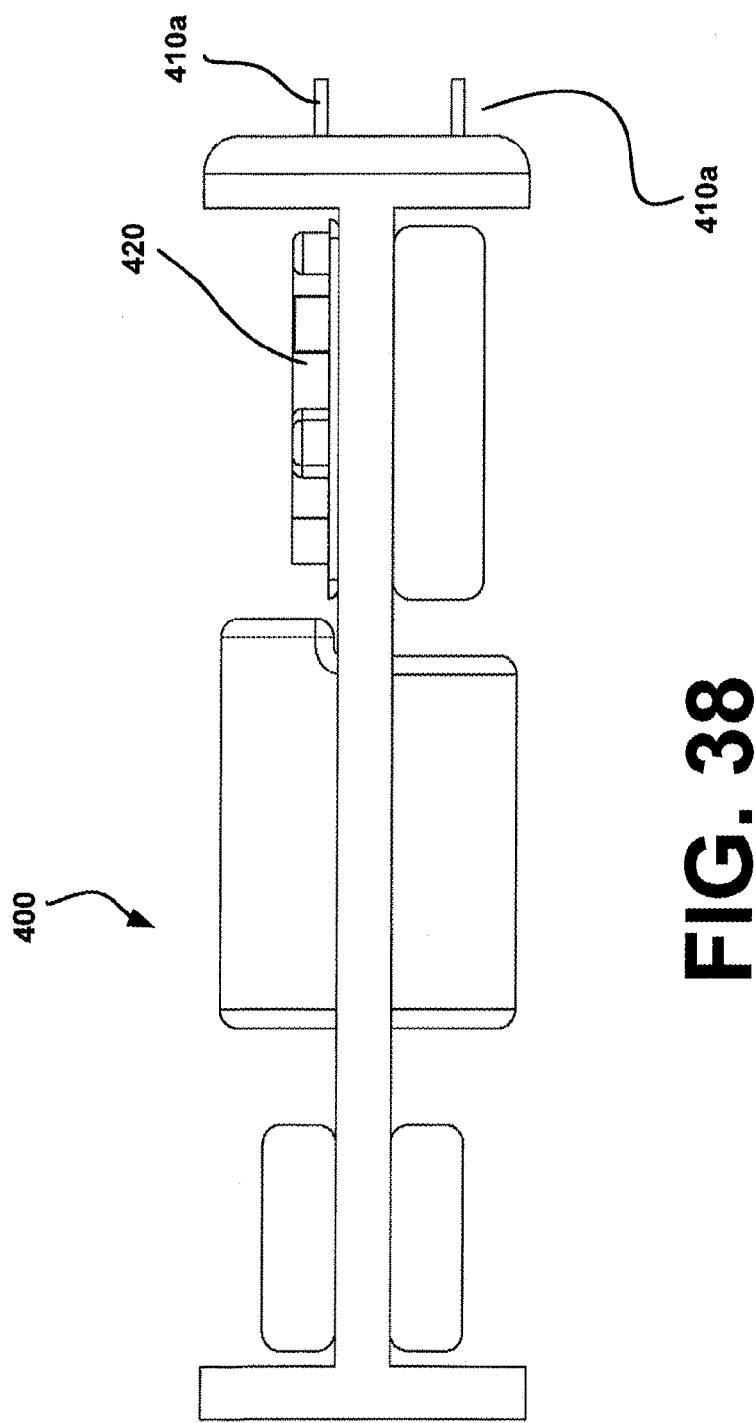
FIG. 38 is a side view of an electronics module, in accordance with one particular embodiment of the present invention.

It is further possible to include a plurality of actuatable tools in the cannula, as shown in FIGS. 36A-36C. More particularly, these figures show the operation of a cannula attached to a handle including a plurality of actuators, wherein the cannula includes both a spreader device to spread a fat pad or other interfering element away from a site and a scissor-type tool, for cutting. The spreader 310 can be used, for example, to isolate a region for imaging, cutting or performing other surgical, diagnostic or therapeutic procedures. In one embodiment, the spreader 310 can be controlled using the engagement mechanism 304 to retract the distal end 303 of the cannula 302.

Other tools can be used in addition to and/or instead of, the tools shown in the present figures.

The Handle:

The system of the present invention additionally includes a light weight sterile handle connected to the cannula, a non-sterile reusable electronics module (EM) and a receiver-monitor unit. In another embodiment the EM can be disposable. In one particular embodiment of the invention, the non-sterile EM is inserted into a chamber in the handle and sealed closed. After closing this handle, it is sterile on the outside and can therefore be used as a surgical instrument in the sterile field. For example, such an endo-surgical device in accordance with the instant invention is shown in FIG. 1, wherein a disposable cannula including at least a portion of the imaging device and having a tip adapted for a particular surgical procedure is connected to the handle using a connector, for example, the feed-through connector 35 of FIG. 4A. Said connector connects the electronics of the cannula to the EM that has been inserted into the endo-surgical device handle. Once inserted into the handle, the EM becomes sealed in, for example, by the sterile cap 32 of FIGS. 1, 2, 3, 4A-4C which additionally may include a seal, so that, after closing it, the handle and cap assembly is sterile on the outside and can be used as a surgical instrument in the surgical sterile field.

As also shown in FIG. 4A, the EM 40 inside the handle 30 of the endo-surgical tool can communicate data, including processed image data, to a receiver 42 which captures the data and relays it to a display 50. Although shown in FIG. 4A as wirelessly communicating with the receiver, further embodiments include a wired connection between the handle and the receiver.

The handle 30 (FIGS. 1 and 2) fits in the surgeon's hand and is either sterilizable or, in another embodiment (FIG. 4D) comes incorporated with the cannula and cable connector as a unit in a sterile pack. It may include part of the surgical instrument activating mechanism such as the trigger or lever 168. The unsterile EM 40 (FIG. 2) is housed within the handle. The EM includes components that because of heat intolerance and chemical sensitivity may be difficult to sterilize. The handle section creates a barrier between the sterile field and the EM. In one particular embodiment (FIG. 2), before surgery, the reusable electronics module 40 is dropped into an opening in the handle and sealed with a cap 32. Electrical connections to the imaging device in the cannula are established through a feed through connector 35. In the case of fiberoptic lighting, fiberoptic cables will connect to the reusable electronic module which will include a light source. The handle section is then closed in a sealed fashion by the cap 32. The seal can be provided by means such as a sealing ring, threaded engagement or tightly fitting surfaces. Actuators, such as actuator 34, buttons and/or other means of controlling the functions can be present on the handle, with sealed feed-throughs to the EM. As mentioned previously, in one embodiment the cannula is disposable and the handle would be reused after sterilization, such as, in an autoclave. In another embodiment, the handle, the cannula and the connector cable are integrated and come as one single sterile packed unit which can be discarded after use.

Additionally, in one particular embodiment (FIG. 3A), the handle 30 may include an arm 36 to which a display 54 can be attached. The attachment port 38 provides for connection of the display to the EM. The arm provides a mechanism for rotation of the display in any or all of three axes to accommodate the visualization needs of the surgeon.

Electronics Module

Figure 2:
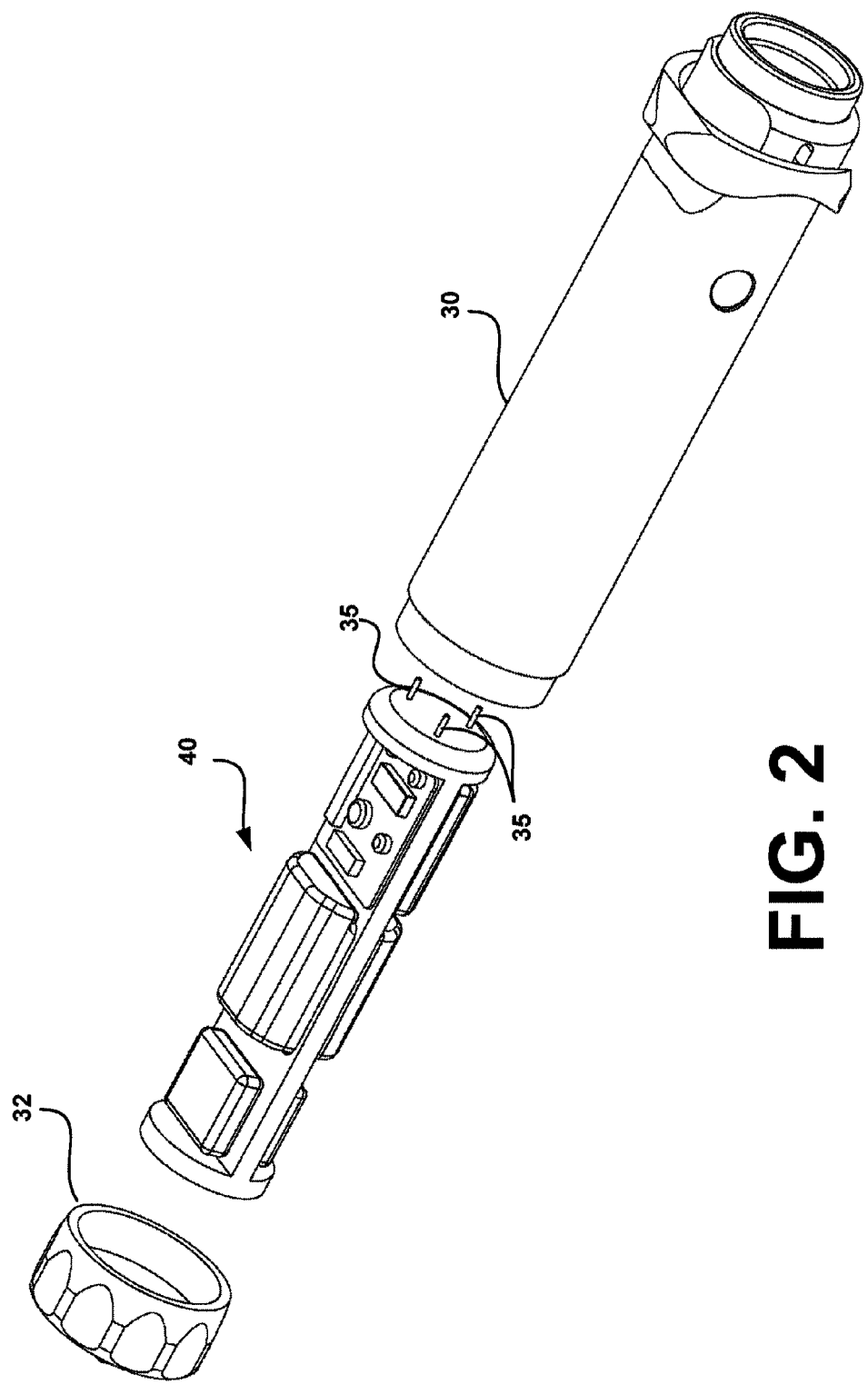
FIG. 2 is an exploded view of a portion of the endo-surgical system of FIG. 1.

Referring now to FIGS. 37-39B, there is shown an integrated electronics module (EM) 400, which may be of the same as, or similar to, the EM 40 of FIG. 2. The EM 400 is sized to be received within the handle 300 and designed to perform one or more of the following functions:

(1) provide power to the imaging device, part of which is located within the cannula;
(2) provide control signals to the cannula electronics, if necessary;
(3) provide power to one or more LEDs located within the imaging device or the prow of the cannula or, alternatively, provide light to be transmitted to the distal end of the cannula via the light channel of an endoscope, optical fibers or light tunnel;
(4) electronically process the image captured by the image sensor within the cannula or, alternatively, video capture and process an optical image from an endoscope inserted into the cannula;
(5) transmit the processed image wirelessly to a receiver coupled to a display or, alternatively, transmit the image via wire (USB or other) to a tethered monitor or display;
(6) record processed images for future downloading;
(7) provide power to the image processor, video camera, wireless transmitter and recorder within the EM and/or the display outside the EM; and.
(8) transmit raw data for processing outside the handle.

The EM 400 (FIG. 37) may include one, all or any combination of the following components: an image sensor, a video camera, an image processor, a light source, a power supply, a battery (rechargeable or not), a wireless transmitter, a recorder, a memory module (memory stick or chip), a connector, such as a USB type connector (see, for example, FIG. 4B). Note that, in one preferred embodiment, at least the image sensor and LED light source are located in the cannula, and not on the integrated electronics module 400. However, in such an embodiment, the EM would be in electrical communication with the electronics in the cannula through an electrical connector of which prongs 410a may be part.

The EM 400 is an integrated removable module that includes, among other components, the circuitry necessary for providing the functionality to the handle and/or cannula. For example, in an embodiment wherein the image sensor is located remotely from the EM 400, i.e., towards the distal end of the cannula, the EM 400 of that embodiment can include the electronic circuitry 420 needed to process and/or forward the information from the image sensor in the cannula. Additionally, in one preferred embodiment, the EM 400 includes a power supply 430 to power the instrument. If an image sensor, video camera, light source, etc., are included in the EM 400, then the power supply 430 will additionally power those devices. In one particular embodiment, the power supply 430 is a rechargeable battery.

Additionally, in one particular embodiment wherein the signals from the image sensor and/or image processor are relayed wirelessly to a display, the electronic circuitry on the circuit board 420 of the EM 400 will additionally include a wireless transmitter to transmit the data to a remote receiver and/or display. The EM 400 can also include, if desired, a device for recording data, a light source, and/or a cable connector for connecting the handle 300, and thus the EM 400, to a tethered display for displaying images captured at the distal end of the cannula. A connector 434, (such as a USB connector, RCA jack, coaxial connector, FIREWIRE connector, or similar other) can also be included in the handle 300 in communication with the EM 400, to provide an external connection to the EM 400, through which images collected by the device can be output. Additionally, in one particular embodiment wherein the power supply 430 is rechargeable, the connector 434 can be of a type (such as USB) that, when connected to a source of power will recharge the power supply 430. A memory card or chip (not shown) can be incorporated into the EM and/or could interface with the EM, via a connector on the handle, to record image data sourced from the imaging device. Note that, if desired, the power supply 430 and/or other items making up the EM 400 can be provided in a separate stand-alone unit connected to the EM 400 through the connector 434.

The EM 400 may be non-sterile and reusable. For example, the EM 400 can be inserted into the handle for use in a procedure, and then removed after the procedure, so that the handle can be re-sterilized or disposed of. The EM 400 can then be replaced into the sterilized handle, or into a new handle, for immediate reuse in another procedure. Once the EM 400 is inserted into the handle and sealed with a sterile cap 432 (or 32 of FIGS. 1-4B), it is isolated in such a way that the outside surface of the completed assembly remains sterile and can be used within a sterile surgical field.

In another embodiment (FIG. 4D) all or portions of the EM 40 are located outside the handle and connected to the handle via a cable 52, which carries the raw image data from the imaging device at the tip of cannula 20.

Monitor or Display

Referring back to FIGS. 1, 3A-3B and 4, it can be seen that the system 10, 10', 10'', 10''' and 10'''' of the present invention includes a display 50, 54 that is, desirably, located within the surgical field. The purpose of the display 50, 54 is to provide the surgeon with a real-time image without shifting their gaze from the sterile surgical site, as captured by the imaging device located in the cannula 20.

As shown more particularly in FIG. 3A, a display 54 can be attached to the handle 30' through an arm 36 with a direct connection 38 to the EM (40' of FIG. 4A). The arm 36 permits rotation of the display 54 in any and all of three axes. Alternately, or in addition, as shown in FIGS. 1 and 4D, a display 50 may be detached from the handle 30 and placed in any location that accommodates the visualization needs of the surgeon. When detached from the handle, the display 50 can receive image data from the EM wirelessly (as shown in FIG. 3B) via a receiver 56, and/or through a wired connection (as shown in FIG. 1) or by direct connection to the EM (FIG. 4D). The wired connection 52 of FIG. 1 can be accomplished using any type of suitable cable or connector, such as a coaxial cable, a USB cable, a FIREWIRE connection, or equivalent.

Additionally, the display 50, 54 can be of a known type of display, including, but not limited to, an LCD flat panel display or a TV monitor. Alternatively or in addition, images may be transmitted from the EM to one or more monitors or projectors that can display or project images to alternate locations inside or outside of the sterile surgical field.

In one particular preferred embodiment, the display 50, 54 receives processed images from the EM 40' located in the handle of the device. However, it should be understood that, if desired, the display 50, 54 can be attached to a processing device that receives raw image data from the electronics module and processes the image data, externally from the handle, for display on the display 50, 54.

Referring to FIGS. 40A-40D, there are shown some alternate paths that could be used by the instant invention to carry image data to the display. For example, referring now to FIG. 40A, the image sensor 510 and the image processor 520 are located in the cannula and/or handle 500, wherein processed images are provided to a display module 530, which includes a display 540, via the wired connection 550. Note that, although the cannula/handle assembly 500 is shown as a unitary group, for purposes of illustration, it is understood that the cannula can be detachably removable from the handle, or formed integrally with the handle, as described herein. Additionally, the image sensor 510 and image processor 520 can be located in the handle, in the cannula and/or distributed with some portion in each of the cannula and handle.

Figure 40A:
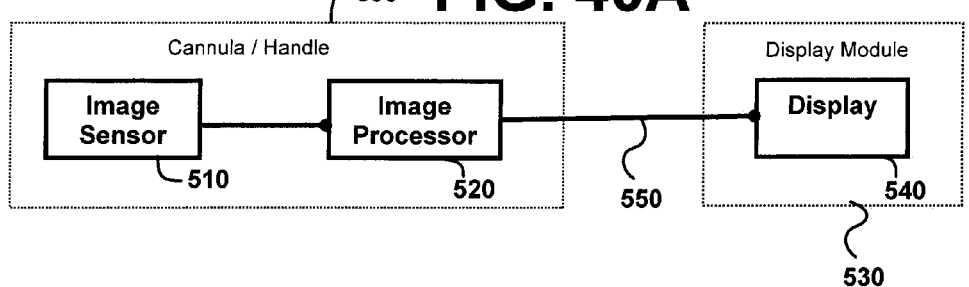
FIGS. 40A-40D are block diagrams showing various embodiments of systems useful with the present invention for providing image data between the end of a cannula and a display.
Figure 40B:
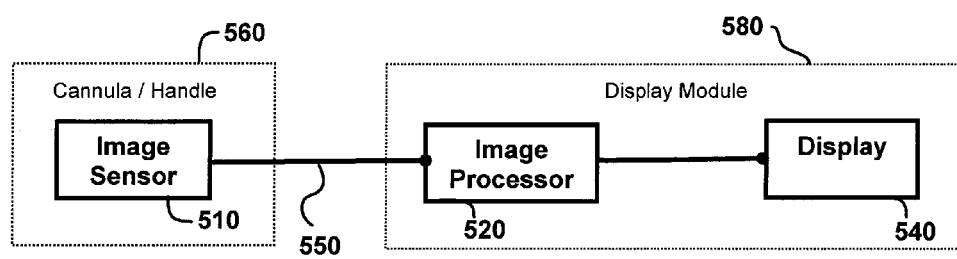

Referring now to FIG. 40B, there is shown an embodiment wherein the image sensor 510 is located in the cannula and/or in the handle of the assembly 560, while at least a portion of the image processor 520 is located in the display module 580. As such, the cannula/handle assembly 560 sends raw image data from the image sensor 510 to the display module 580, via the wired connection 550.

Figure 40C:
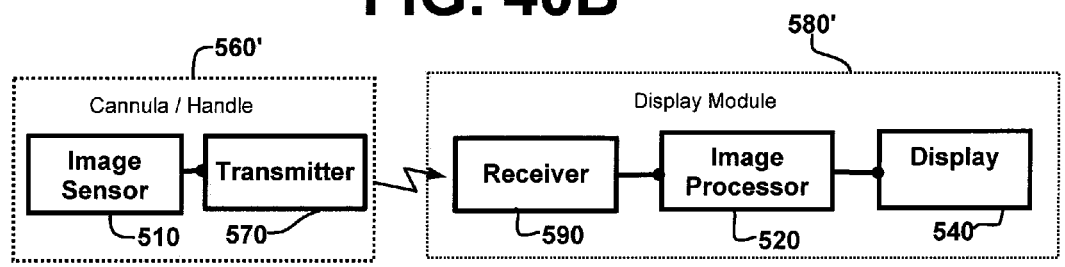
Figure 40D:
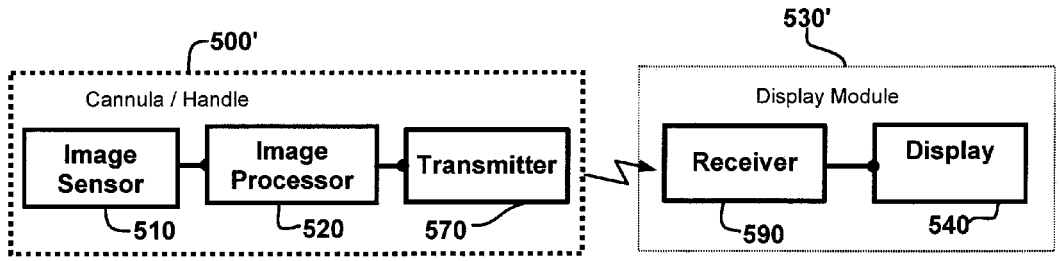

The system of FIG. 40C is substantially similar to that of FIG. 40B, except that the cannula/handle assembly 560' includes a wireless transmitter 570, and the display module 580' includes a wireless receiver 590, and the raw image data from the image sensor 510 is transmitted to the image processor 520, wirelessly. Similarly, the system of FIG. 40D is substantially similar to that of FIG. 40A, except that the cannula/handle assembly 500' includes a wireless transmitter 570, and the display module 530' includes a wireless receiver 590, and the image data processed by the image processor 520 is transmitted from the assembly 500' to the display module 530', wirelessly.

Referring more particularly to FIG. 3A, there is shown one particular embodiment of an inline endo-surgical carpel tunnel release cannula 20 that is connected to a handle 30' including a display 54. The cannula 20 can be straight, angled or curved as described elsewhere herein. Additionally, as shown in FIG. 3A, the handle 30' can incorporate a connector 38, through which the monitor arm 36 can connect the display 54 to the EM 40' handle 30'. Additionally, cables, wires, and/or other connectors (not shown) can be wired through the arm 36 to connect with or contact components within the handle 30'. For example, in one particular embodiment, a cable (not shown) extending between the display 54 and an EM in the handle 30' can run within a lumen in the display arm 36. Alternately, the display 54 can receive images wirelessly from the EM in the handle.

In one embodiment, the monitor can rotate about an axis perpendicular to the longitudinal plane of the handle. Additionally, the display 54 can be positioned for ease of viewing without moving the cannula 20. Although shown in FIG. 3A as being inline with the cannula 20, if desired, the handle can be offset from the display, instead of inline. Further, if desired, the display can be detached from the handle 30' and used wirelessly or through a wired connection (i.e., set on table while performing surgery).

Figure 39A:
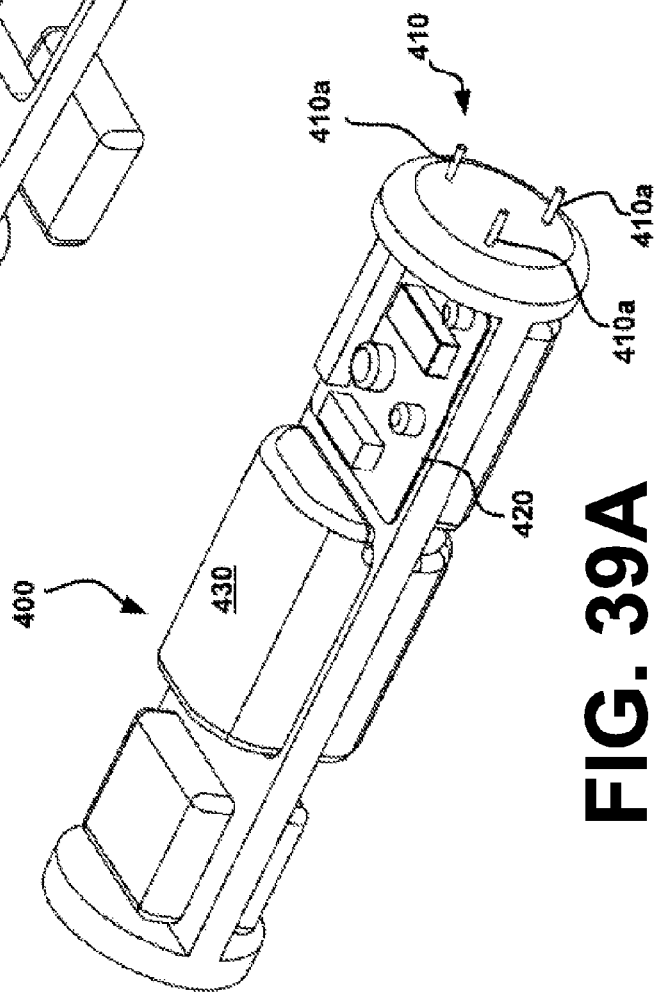
FIG. 39A is a perspective view of an electronics module, in accordance with a particular embodiment of the present invention.

As discussed above in connection with the EM, the device 10, 10', 10'', 10''' and 10'''' can include, a power supply (430 of FIG. 39A). If desired, the power supply (430 of FIG. 39A) can also provide power for the display 50, 54.

Additionally, to ensure that the system including the display 50, 54 is sterile, the display 50, 54 can be encased within a sterile plastic bag or case (60 of FIG. 4D) that includes a pass-through connector, whenever it is within the surgical field. Such a pass-through connector can be of any known connection mechanism such as, for example, female connectors, coaxial, RCA, etc., that can provide electrical contact between the display 50, 54 and/or EM 40 inside the bag and components within the handle 30 or cannula 20 while maintaining sterility. Additionally, the plastic bag can include a zip-lock closure mechanism or other air-tight closure mechanism. In one particular embodiment of the present invention, the plastic bag can include a flat or rigid section for maintaining a clear view of the monitor screen through the bag wall. In a further embodiment, the bag can include VELCRO™ or other adhesive to prevent bunching of the bag in front of the screen and/or to keep the flat or rigid section in place in front of the screen.

If desired, the plastic bag can be omitted and the casing of the display 50, 54 and EM 40 can be made to be watertight. In such an embodiment, the waterproof display 50, 54 is capable of being disinfected by a disinfectant solution such as, for example, CIDEX™, in order to render it sterile. Additionally, the joints, display, and handle of all of the present embodiments can be made waterproof for disinfection in a liquid disinfectant solution, to be rendered sterile.

Alternately, or in a addition thereto, a conventional non-sterile monitor can be provided, which is of the type commonly found in surgical suites, on endoscopic towers, to which a non sterile receiver has been connected and to which a recording or printing device can be attached.

Although some of the above-embodiments describe the use of the display 50, 54 with an EM located in the handle, this is not meant to be limiting as can be readily seen in the embodiment illustrated in FIG. 4D. Rather, it can be seen how the cannulas and handles of the instant invention could provide images to a display connected to a video camera at the proximal end of an endoscope in communication with the EM. Such an embodiment is described in connection with FIG. 4B.

FIGS. 42-44 show representative top, front and cross-sectional views of certain prior art devices, and illustrate that the cross-sectional dimensions of those devices either do not change over their lengths or taper proximally to distally. Referring now to FIG. 45, it can be seen in the top, front and cross-sectional views of one embodiment of the present invention that the cannula's geometry changes to achieved the before mentioned advantages.

Among other advantages, by providing a display within the surgical field and, in particular, "inline" with the cannula, a surgeon can see the display while performing the surgical procedure, without turning to view an image to the side or far away from the operating site. The display of the instant invention eliminates the need for attaching the surgical device to an external monitor via a heavy video cable, and additionally eliminates the need for another heavy fiber optic cable to connect to a light source. The instant invention can shorten the labor required of nurses and technicians to set-up the system, thereby cutting set-up time.

While the invention has been described with reference to certain embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiments disclosed as the best or preferred modes contemplated for carrying out this invention, but that the invention will include all embodiments falling within the scope of the appended claims.

We claim:

1. An endo-surgical device, comprising:
   a cannula, including a shaft portion and a prow, said prow being located at the distal end of said shaft portion, the walls and bottom of said prow defining a cavity that is open at top of the prow;
   said bottom of said prow being lower than the lower surface of said shaft portion and said walls of said prow being wider than side surfaces of said shaft portion and at least a portion of said top of said prow being higher than an upper surface of said shaft portion;
   said prow further including a pivot pin;
   a cutting blade contained in, and deployable from said prow, at least a portion of said cutting blade being retained by said pivot pin in said prow, said cutting blade in a first position, being shielded by closely spaced ribs in the cavity of said prow;
   said cutting blade including a blade slot slideably engaged with said pivot pin;
   an actuation mechanism connected to said blade such that actuation of said actuation mechanism causes said blade slot to slide relative to said pivot pin; and
   said blade slot and pivot pin configured to deploy a distal tip of said blade along an arcuate path that is an arc of a circle that projects above and towards the distal end of the prow upon actuation by said actuation mechanism.

2. The endo-surgical device of claim 1, wherein said cannula includes at least a portion of an imaging device therein.

3. The endo-surgical device of claim 1, wherein the upper surface at the distal edge of the prow has a flat contact surface.

4. The endo-surgical device of claim 3, wherein the flat contact area is formed by said closely spaced ribs said closely spaced ribs being aligned parallel to the longitudinal axis of said cannula.

5. The endo-surgical device of claim 1, wherein the greatest width of said prow exceeds the height of said prow at the section of the prow having the greatest width.

6. The endo-surgical device of claim 1, wherein the cross section of the prow is shaped as an inverted bell.

7. The endo-surgical device of claim 1, further including a handle, wherein the cannula and the handle form a single unit.

8. The endo-surgical device of claim 1, wherein the upper edges of said prow are flared, such that the upper edges of said prow gradually diverges distally from the shaft, until a maximum separation is reached, after which, the upper edges converge towards the distal end of said prow.

9. The endo-surgical device of claim 8, wherein said cannula includes at least a portion of an imaging device therein.

10. The endo-surgical device of claim 9, wherein said imaging device includes an image sensor.

11. The endo-surgical device of claim 9, wherein the imaging device includes an optical endoscope.

12. The endo-surgical device of claim 9, wherein the proximal end of said cannula shaft includes a connector for connecting the cannula to a handle.

13. The endo-surgical device of claim 12, wherein said connector connects said imaging device to an electronics module in the handle.

14. The endo-surgical device of claim 12, wherein said connector mechanically links an actuator on the handle to a mechanism that moves at least one of said prow and said cutting blade.

15. The endo-surgical device of claim 14, wherein said mechanism drops a portion of the prow to expose said cutting blade.

16. The endo-surgical device of claim 14, wherein said mechanism raises at least a portion of said cutting blade above the upper surface of the prow.

17. The endo-surgical device of claim 14, wherein said mechanism raises at least a portion of the surgical implement above the upper surface of the prow and drops a portion of the prow to further expose said cutting blade.

18. A system for performing an endo-surgical procedure, comprising:
   a cannula, including a shaft portion and a prow, said prow being located at the distal end of said shaft portion, the walls and bottom of said prow defining a cavity that is open at top of the prow;
   said bottom of said prow being lower than the lower surface of said shaft portion and said walls of said prow being wider than side surfaces of said shaft portion and at least a portion of said top of said prow being higher than an upper surface of said shaft portion;
   said prow further including a pivot pin;
   a cutting blade contained in, and deployable from said prow, at least a portion of said cutting blade being retained by said pivot pin in said prow, said cutting blade in a first position, being shielded by closely spaced ribs in the cavity of said prow;

said cutting blade including a blade slot slideably engaged with said pivot pin;

an actuation mechanism connected to said cutting blade such that actuation of said actuation mechanism causes said blade slot to slide relative to said pivot pin;

said blade slot and pivot pin configured to deploy a distal tip of said blade along an arcuate path that is an arc of a circle that projects above and towards the distal end of the prow upon actuation by said actuation mechanism;

an imaging device, at least a portion of which is in optical communication with said cavity; and a display for displaying images obtained from said imaging device.

19. The endo-surgical system of claim 18, wherein said prow is curved such that the distal end of said prow is above the upper surface of said shaft portion.

20. The endo-surgical system of claim 18, wherein the upper edges of said prow are flared, such that the upper edges of said prow gradually diverges distally from the shaft, until a maximum separation is reached, after which, the upper edges converge towards the distal end of said prow.

21. The endo-surgical system of claim 18, wherein said imaging device includes an optical endoscope.

22. The endo-surgical system of claim 18, wherein said imaging device includes an image sensor located in said cannula.

23. The endo-surgical system of claim 22, wherein said imaging device is in communication with an electronics module located outside the handle.

24. The endo-surgical system of claim 22, wherein said system includes a handle and said imaging device is in communication with electronics contained in said handle.

25. The endo-surgical system of claim 24, wherein said electronics contained in said handle are part of an electronics module contained in said handle.

26. The endo-surgical system of claim 23, wherein said cannula is removably connected to said handle through a connector, said connector connecting at least an imaging device in said cannula to said electronics module.

27. A surgical device for performing ECTR, comprising:
a cannula, including a shaft portion and a prow, said prow being located at the distal end of said shaft portion, the walls and bottom of said prow defining a cavity that is open at top of the prow;
at least a portion of said prow being at least one of wider than said shaft portion or higher than the upper surface of said shaft portion;
said prow further including a pivot pin;
a cutting blade contained in, and deployable from said prow, at least a portion of said cutting blade being retained by said pivot pin in said prow, said cutting blade in a first position, being shielded by closely spaced ribs in the cavity of said prow;
said cutting blade including a blade slot slideably engaged with said pivot pin;
an actuation mechanism connected to said cutting blade such that actuation of said actuation mechanism causes said blade slot to slide relative to said pivot pin; and
said blade slot and pivot pin configured to deploy a distal tip of said blade along an arcuate path that is an arc of a circle that projects above and towards the distal end of the prow upon actuation by said actuation mechanism.

28. The surgical device of claim 27, wherein said prow is curved such that the distal end of said prow is above the upper surface of said shaft portion proximal to said prow.

29. The surgical device of claim 27, wherein said cannula includes at least a portion of an imaging device therein.

30. The surgical device of claim 27, wherein the upper surface at the distal edge of the prow has a flat contact surface.

31. The surgical device of claim 30, wherein the flat contact area is formed by said closely spaced ribs, said closely spaced ribs being aligned parallel to the longitudinal axis of said cannula.

32. The surgical device of claim 27, wherein the greatest width of said prow exceeds the height of said prow at the section of the prow having the greatest width.

33. The surgical device of claim 27, wherein the width of said prow is greater than the width of said cannula shaft.

34. The surgical device of claim 27, wherein the cross section of the prow is shaped as an inverted bell.

35. The surgical device of claim 27, further including a handle, wherein the cannula and the handle form a single unit.

36. The surgical device of claim 27, wherein the upper edges of said prow are flared, such that the upper edges of said prow gradually diverges distally from the shaft, until a maximum separation is reached, after which, the upper edges converge towards the distal end of said prow.

37. The surgical device of claim 36, wherein said cannula includes at least a portion of an imaging device therein.

38. The surgical device of claim 37, wherein said imaging device includes an image sensor.

39. The surgical device of claim 37, wherein the imaging device includes an optical endoscope.

40. The surgical device of claim 37, wherein the proximal end of said cannula shaft includes a connector for connecting the cannula to a handle.

41. The surgical device of claim 40, wherein said connector connects said imaging device to an electronics module in the handle.

42. The surgical device of claim 40, wherein said connector mechanically links an actuator on the handle to a mechanism that moves at least one of said prow and said cutting blade.

43. The surgical device of claim 42, wherein said mechanism drops a portion of the prow to expose said cutting blade.

44. The surgical device of claim 42, wherein said mechanism raises at least a portion of the said cutting blade above the upper surface of the prow.

45. The surgical device of claim 42, wherein said mechanism raises said cutting blade along an arcuate path defined on a plane that is parallel to the longitudinal axis of said cannula.

46. The surgical device of claim 42, wherein said mechanism raises at least a portion of the cutting blade above the upper surface of the prow and drops a portion of the prow to further expose said cutting blade.

47. The surgical device of claim 27, wherein, said cutting blade is, in a first position, below the upper edges of the prow during insertion.

* * * * *

UNITED STATES PATENT AND TRADEMARK OFFICE
CERTIFICATE OF CORRECTION

PATENT NO. : 8,992,424 B2
APPLICATION NO. : 12/029232
DATED : March 31, 2015
INVENTOR(S) : Orbay et al.

Page 1 of 1

It is certified that error appears in the above-identified patent and that said Letters Patent is hereby corrected as shown below:

On the title page

Item (75) Inventors: Jorge L. Orbay, Miami, FL (US); Jorge A. Machado, Miami, FL (US); Thomas H. Norman, Miami, FL (US); Alejandro Espinosa, Miami, FL (US); Randall Chinock, Southbridge, MA (US); Ronald G. Litke, Jr., Shelton, CT (US); Carlos Valencia, Miami, FL (US)

Delete the phrase "Randall Chinock" and insert -- Randal Chinnock --

Signed and Sealed this
Tenth Day of May, 2016

Michelle K. Lee
*Director of the United States Patent and Trademark Office*